US006824993B2

(12) United States Patent
Soppet et al.

(10) Patent No.: US 6,824,993 B2
(45) Date of Patent: Nov. 30, 2004

(54) ANTIBODIES THAT BIND HUMAN PROSTATE SPECIFIC G-PROTEIN RECEPTOR HPRAJ70

(75) Inventors: Daniel R. Soppet, Centreville, VA (US); Yi Li, Sunnyvale, CA (US); Craig A. Rosen, Laytonville, MD (US); Steven M. Ruben, Olney, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 151 days.

(21) Appl. No.: 09/968,033

(22) Filed: Oct. 2, 2001

(65) Prior Publication Data

US 2002/0168717 A1 Nov. 14, 2002

Related U.S. Application Data

(60) Continuation-in-part of application No. 09/339,115, filed on Jul. 24, 1999, now Pat. No. 6,372,891, which is a division of application No. 09/053,303, filed on Apr. 1, 1998, now Pat. No. 5,948,890, which is a division of application No. 08/465,980, filed on Jun. 6, 1995, now Pat. No. 5,756,309.
(60) Provisional application No. 60/237,275, filed on Oct. 3, 2000.

(51) Int. Cl.$^7$ .................. C07K 16/18; C07K 16/28; C07K 16/30; G01N 33/53
(52) U.S. Cl. .................. 435/7.2; 435/7.1; 435/7.25; 435/7.92; 424/130.1; 424/141.1; 424/142.1; 424/133.1; 424/143.1; 424/138.1; 424/139.1; 530/387.1; 530/387.3; 530/387.7; 530/387.9; 530/388.1; 530/388.15; 530/388.22; 530/389.1; 530/389.7; 530/391.1; 530/391.3
(58) Field of Search .................. 435/7.1, 7.2, 7.25, 435/7.92; 424/130.1, 141.1, 142.1, 133.1, 143.1, 138.1, 139.1; 530/387.1, 387.3, 387.7, 387.9, 388.1, 388.15, 388.22, 389.1, 389.7, 391.1, 391.3

(56) References Cited

U.S. PATENT DOCUMENTS 5,948,890 A     9/1999  Soppet et al.
6,372,891 B1 *  4/2002  Soppet et al. ............ 530/387.9

FOREIGN PATENT DOCUMENTS

WO      WO 92/17585      10/1992

OTHER PUBLICATIONS

Parmentier et al., "Expression of members of the putative olfactory receptor gene family in mammalian germ cells," Nature 355:453–455 (1992).

Raitano et al., Genbank AAB85003 (2001).
Bowie, et al., "Deciphering the Message in Protein Sequences: Tolerance to Amino Acid Substitutions," *Science*, 247:1306–1310 (1990).
Skolnick, et al., "From genes to protein structure and function: novel applications of computational approaches in the genomic era," *TIBTECH*, 18(1):34–39 (2000).
Lee, et al., "Molecular Biology of G–Protein–Coupled Receptors," *DN&P*(??), 6(7):488–497 (1991).
Oliveira, et al., "A common motif in G–protein–coupled seven transmembrane helix receptors," *J. Computer–Aided Molecular Design*, 7(6):649–658 (1993).
Ross, et al., "RTA, a candidate G protein–coupled receptor: Cloning, sequencing, and tissue distribution," *PNAS USA*, 87:3052–3056 (1990).
Libert, et al., "Selective amplification and cloning of our new members of the G protein–coupled receptor family," *Science*, 244(4904):568–572 (1989).
Eva, et al., "Molecular cloning of a novel G protein–coupled receptor that may belong to the neuropeptide receptor family," *FEBS Letter*, 271:81–84 (1990).
Buck, et al., A Novel Multigene Family May Encode Odorant Receptors: A Molecular Basis for.
Zhong et al., "Molecular Cloning of the Rat Vascular Smooth Muscle Thrombin Receptor," *J. Biol. Chem.*, 267(24):16975–16979 (Aug. 25, 1992).

* cited by examiner

*Primary Examiner*—Elizabeth Kemmerer
(74) *Attorney, Agent, or Firm*—Human Genome Sciences, Inc.

(57) ABSTRACT

The present invention relates to PSGR, a novel prostate specific gene with homology to a G-protein coupled receptor overexpressed in prostate cancer. More specifically, the invention relates to PSGR polynucleotides and the polypeptides encoded by these polynucleotides, and the use of PSGR polynucleotides and polypeptides for detecting disorders of the reproductive system, including disorders of the prostate, particularly the presence of cancer. This invention relates to PSGR polynucleotides and polypeptides as well as vectors, host cells, antibodies directed to PSGR polynucleotides and polypeptides and recombinant and synthetic methods for producing the same. Also provided are methods for diagnosing, treating, preventing, and/or prognosing disorders related to the prostate, including cancer. The invention further relates to screening methods for identifying agonists and antagonists of PSGR polynucleotides and polypeptides of the invention and methods and/or compositions for inhibiting or enhancing the production and/or function of the PSGR polypeptides of the present invention.

16 Claims, 6 Drawing Sheets

Figure 1A

```
1   ATG AGT TCC TGC AAC TTC ACA CAT GCC ACC TGT GTG CTT ATT GGT ATC CCA GGA TTA GAG   60
1    M   S   S   C   N   F   T   H   A   T   C   V   L   I   G   I   P   G   L   E    20

61  AAA GCC CAT TTC TGG GTT GGC TTC CCC CTC CTT TCC ATG TAT GTA GTG GCA ATG TGT GGA   120
21   K   A   H   F   W   V   G   F   P   L   L   S   M   Y   V   V   A   M   C   G    40

121 AAC TGC ATC GTG GTC TTC ATC GTA AGG ACG GAA CGC AGC CTG CAC GCT CCG ATG TAC CTC   180
41   N   C   I   V   V   F   I   V   R   T   E   R   S   L   H   A   P   M   Y   L    60

181 TTT CTC TGC ATG CTT GCA GCC ATT GAC CTG GCC TTA TCC ACA TCC ACC ATG CCT AAG ATC   240
61   F   L   C   M   L   A   A   I   D   L   A   L   S   T   S   T   M   P   K   I    80

241 CTT GCC CTT TTC TGG TTT GAT TCC CGA GAG ATT AGC ATT GAG GCC TGT CTT ACC CAG ATG   300
81   L   A   L   F   W   F   D   S   R   E   I   S   I   E   A   C   L   T   Q   M    100

301 TTC TTT ATT CAT GCC CTC TCA GCC ATT GAA TCC ACC ATC CTG CTG GCC ATG GCC TTT GAC   360
101  F   F   I   H   A   L   S   A   I   E   S   T   I   L   L   A   M   A   F   D    120

361 CGT TAT GTG GCC ATC TGC CAC CCA CTG CGC CAT GCT GCA GTG CTC AAC GTG CTC TTT TTC CCA CTG CCT CTG   420
121  R   Y   V   A   I   C   H   P   L   R   H   A   A   V   L   N   N   T   V   T    140

421 GCC CAG ATT GGC ATC GTG GCT GTG GTC CGC GGA TCC CTC TTT TTT TTC CCA CTG CCT CTG   480
141  A   Q   I   G   I   V   A   V   V   R   G   S   L   F   F   F   P   L   P   L    160

481 CTG ATC AAG CGG CTG GCC TTC TGC CAC TCC AAT GTC CTC TCG CAC TCC TAT TGT GTC CAC   540
161  L   I   K   R   L   A   F   C   H   S   N   V   L   S   H   S   Y   C   V   H    180
```

Figure 1B

```
541 CAG GAT GTA ATG AAG TTG GCC TAT GCA GAC ACT TTG CCC AAT GTG GTA TAT GGT CTT ACT 600
181  Q   D   V   M   K   L   A   Y   A   D   T   L   P   N   V   V   Y   G   L   T  200

601 GCC ATT CTG GTC ATG GGC GTG GAC GTA ATG TTC ATC TCC TTG TCC TAT TTT CTG ATA 660
201  A   I   L   V   M   G   V   D   V   M   F   I   S   L   S   Y   F   L   I  220

661 ATA CGA ACG GTT CTG CAA CTG CCT TCC AAG TCA GAG CGG GCC AAG GCC TTT GGA ACC TGT 720
221  I   R   T   V   L   Q   L   P   S   K   S   E   R   A   K   A   F   G   T   C  240

721 GTG TCA CAC ATT GGT GTG CTA CTC GCC TTC TAT GTG CCA CTT ATT GGC CTC TCA GTT GTA 780
241  V   S   H   I   G   V   L   L   A   F   Y   V   P   L   I   G   L   S   V   V  260

781 CAC CGC TTT GGA AAC AGC CTT CAT CCC ATT GTG CGT GTT ATG GGT GAC ATC TAC CTG 840
261  H   R   F   G   N   S   L   H   P   I   V   R   V   M   G   D   I   Y   L  280

841 CTG CCT CCT GTC ATC ATC AAT CCC ATC ATC TAT GGT GCC AAA ACC AAA ATC AGA ACA 900
281  L   P   P   V   I   I   N   P   I   I   Y   G   A   K   T   K   Q   I   R   T  300

901 CGG GTG CTG GCT ATG TTC AAG ATC AGC TGT GAC AAG GAC TTG CAG GCT GTG GGA GGC AAG 960
301  R   V   L   A   M   F   K   I   S   C   D   K   D   L   Q   A   V   G   G   K  320

961 TGA 963
```

Figure 2A

```
  1 ATG AGT TCC TGC AAC TTC ACA CAT GCC ACC TTT GTG CTT ATT GGT ATC CCA GGA TTA GAG   60
  1  M   S   S   C   N   F   T   H   A   T   F   V   L   I   G   I   P   G   L   E    20

61 AAA GCC CAT TTC TGG GTT GGC TTC CCC CTC CTT TCC ATG TAT GTA GTG GCA ATG TTT GGA  120
 21  K   A   H   F   W   V   G   F   P   L   L   S   M   Y   V   V   A   M   F   G    40

121 AAC TGC ATC GTG GTC TTC ATC GTA AGG ACG GAA CGC AGC CTG CAC GCT CCG ATG TAC CTC  180
 41  N   C   I   V   V   F   I   V   R   T   E   R   S   L   H   A   P   M   Y   L    60

181 TTT CTC TGC ATG CTT GCA GCC ATT GAC CTG GCC TTA TCC ACA TCC ACC ATG CCT AAG ATC  240
 61  F   L   C   M   L   A   A   I   D   L   A   L   S   T   S   T   M   P   K   I    80

241 CTT GCC CTT TTC TGG TTT GAT TCC CGA GAG ATT AGC TTT GAG GCC TGT CTT ACC CAG ATG  300
 81  L   A   L   F   W   F   D   S   R   E   I   S   F   E   A   C   L   T   Q   M   100

301 TTC TTT ATT CAT GCC CTC TCA GCC ATT GAA TCC ACC ATC CTG CTG GCC ATG GCC TTT GAC  360
101  F   F   I   H   A   L   S   A   I   E   S   T   I   L   L   A   M   A   F   D   120

361 CGT TAT GTG GCC ATT GGC GCT GTG GTC CGC CAT CGC CGC CAT GCA GCA CTC AAC AAT ACA GTA ACA  420
121  R   Y   V   A   I   G   A   V   V   R   H   R   H   A   A   V   L   N   N   T   V   T   140

421 GCC CAG ATT GGC ATT GCT GTG GTC CGC GGA TCC GGA TCC CTC TTT TTT TTC CCA CTG CCT CTG  480
141  A   Q   I   G   I   A   V   V   R   G   S   L   F   F   F   P   L   P   L   160

481 CTG AAG CGG CTG GCC TTC TGC CAC TCC AAT GTC CTC TCG CAC TCC TAT TGT GTC CAC  540
161  L   K   R   L   A   F   C   H   S   N   V   L   S   H   S   Y   C   V   H   180
```

Figure 2B

```
541 CAG GAT GTA ATG AAG TTG GCC TAT GCA GAC ACT TTG CCC AAT GTG TAT GGT CTT ACT 600
181  Q   D   V   M   K   L   A   Y   A   D   T   L   P   N   V   Y   G   L   T  200

601 GCC ATT CTG CTG GTC ATG GGC GTG GAC GTA ATG TTC ATC TCC TTG TCC TAT TTT CTG ATA 660
201  A   I   L   L   V   M   G   V   D   V   M   F   I   S   L   S   Y   F   L   I  220

661 ATA CGA ACG GTT CTG CAA CTG CCT TCC AAG TCA GAG CGG GCC AAG GCC TTT GGA ACC TGT 720
221  I   R   T   V   L   Q   L   P   S   K   S   E   R   A   K   A   F   G   T   C  240

721 GTG TCA CAC ATT GGT GTG GTA CTC GCC TTC TAT GTG CCA CTT ATT GTC ATG GGT GAC CTC TCA GTT GTA 780
241  V   S   H   I   G   V   V   L   A   F   Y   V   P   L   I   V   M   G   D   L   S   V   V  260

781 CAC CGC TTT GGA AAC AGC CTT CAT CCC ATT AAT CCC ATC ATC TAT GGT GCC AAA ACC AAA CAG ATC TAC CTG 840
261  H   R   F   G   N   S   L   H   P   I   N   P   I   I   Y   G   A   K   T   K   Q   I   Y   L  280

841 CTG CCT CCT GTC ATC AAG ATG TTC AAG ATC AGC TGT GAC AAG GAC TTG CAG GCT GTG GGA ATC AGA ACA 900
281  L   P   P   V   I   K   M   F   K   I   S   C   D   K   D   L   Q   A   V   G   I   R   T  300

901 CGG GTG CTG GCT ATG TTC AAG ATC AGC TGT GAC AAG GAC TTG CAG GCT GTG GGA GGC AAG 960
301  R   V   L   A   M                                                           K  320

961 TGA 963
```

Figure 3

```
         1                                                             60
HPRAJ70  MSSCNFTH.ATCVLIGIPGLEKAHFWVGFPL.LSMYVVAMCGNCIVVFIVRTERSLHAPM
HGM071   MMGQNQTSISDFLLLGLP.IQPEQQNLCYALFLAMYLTTLLGNLLIVLIRLDSHLHTPM 61                                                            120
HPRAJ70  YLFLCMLAAIDLALSTSTMPKILALFWFDSREISIEACLTQMFFIHALSAIESTILLAMA
HGM071   YLFLSNLSFSDLCFSSVTIPKLLQNMQNQDPSIPYADCLTQMYFFLLFGDLESFLLVAMA 121                                                           180
HPRAJ70  FDRYVAICHPLRHAAVLNNTVTAQIGIVAVVRGSLFFFPL..PLLIKRLAFCHSNVLSHS
HGM071   YDRYVAICFPLHYTAIMSPMLC..LALVALSWVLTTFHAMLHTLLMARLCFCADNVIPHF 181                                                           240
HPRAJ70  YCVHQDVMKLAYADTLPN..VVYGLTAILLVMGVDVMFISLSYFLIIRTVLQLPSKSERA
HGM071   FCDMSALLKLAFSDTRVNEWVIFIMGGLLIV..IPFLLILGSYARIVSSILKVPSSKGIC 241                                                           300
HPRAJ70  KAFGTCVSHIGVVLAFYVPLIGLSVVHREGNSLHPIVRVVMGDIYLLLPPVINPIIYGAK
HGM071   KAFSTCGSHLSVVSLFYGTVIGLYLCSSANSS..TLKDTVMAMMYTVVTPMLNPFIYSLR 301                  326
HPRAJ70  TKQIRTRVLAMFKISCDKDLQAVGGK
HGM071   NRDMKG...ALSRVIHQK..KTFFSL
```

ANTIBODIES THAT BIND HUMAN PROSTATE SPECIFIC G-PROTEIN RECEPTOR HPRAJ70

This application claims benefit under 35 U.S.C. §119(e) of U.S. Provisional Application Ser. No. 60/237,275, filed Oct. 3, 2000, now abandoned, and is a Continuation-in-Part of U.S. application Ser. No. 09/339,115, filed Jun. 24, 1999, now U.S. Pat. No. 6,372,891 which is a divisional of and claims priority under 35 U.S.C. §120 to U.S. application Ser. No. 09/053,303, filed Apr. 1, 1998, now U.S. Pat. No. 5,948,890, issued Sep. 7, 1999, which is a divisional of and claims priority under 35 U.S.C. §120 to U.S. application Ser. No. 08/465,980, filed Jun. 6, 1995, now U.S. Pat. No. 5,756,309, issued May 26, 1998, each of which is hereby incorporated by reference in its entirety.

BACKGROUND OF THE INVENTION

1. Field of the Invention

The present invention relates to PSGR, a novel prostate specific gene with homology to a G-protein coupled receptor overexpressed in prostate cancer. More specifically, the invention relates to PSGR polynucleotides and the polypeptides encoded by these polynucleotides, and the use of PSGR polynucleotides and polypeptides for detecting disorders of the reproductive system, including disorders of the prostate, particularly the presence of cancer. This invention relates to PSGR polynucleotides and polypeptides as well as vectors, host cells, antibodies directed to PSGR polynucleotides and polypeptides and recombinant and synthetic methods for producing the same. Also provided are diagnostic methods for diagnosing and treating, preventing and/or prognosing disorders related to the prostate, including cancer, and therapeutic methods for treating such disorders. The invention further relates to screening methods for identifying agonists and antagonists of PSGR polynucleotides and polypeptides of the invention. The present invention further relates to methods and/or compositions for inhibiting or enhancing the production and/or function of the PSGR polypeptides of the present invention.

2. Related Art

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

In spite of considerable research into therapies for the disease, prostate cancer remains difficult to treat. Commonly, treatment is based on surgery and/or radiation therapy, but these methods are ineffective in a significant percentage of cases. Two previously identified prostate specific proteins—prostate specific antigen (PSA) and prostatic acid phosphatase (PAP)—have limited therapeutic and diagnostic potential. For example, PSA levels do not always correlate well with the presence of prostate cancer, being positive in a percentage of non-prostate cancer cases, including benign prostatic hyperplasia (BPH). Furthermore, PSA measurements correlate with prostate volume, and do not indicate the level of metastasis.

In spite of considerable research into therapies for these and other cancers, prostate cancer remains difficult to diagnose and treat effectively. Accordingly, there is a need in the art for improved methods for detecting and treating such cancers.

G-protein coupled receptors (GPCRs) constitute a major class of proteins responsible for transducing a signal within a cell. GPCRs have three structural domains: an amino terminal extracellular domain; a transmembrane domain containing seven transmembrane segments, three extracellular loops, and three intracellular loops; and a carboxy terminal intracellular domain. Upon binding of a ligand to an extracellular portion of a GPCR, a signal is transduced within the cell that results in a change in a biological or physiological property of the cell. GPCRs, along with G-proteins and effectors (intracellular enzymes and channels modulated by G-proteins), are the components of a modular signalling system that connects the state of intracellular second messengers to extracellular inputs.

GPCRs are a major target for drug action and development. Accordingly, it is valuable to the field of pharmaceutical development to identify and characterize previously unknown GPCRs. The present invention advances the state of the art by providing a previously unidentified prostate specific seven transmembrane GPCR.

SUMMARY OF THE INVENTION

The present invention provides isolated nucleic acid molecules comprising, or alternatively, consisting of, a polynucleotide encoding at least a portion of PSGR. Thus, the present invention provides isolated nucleic acid molecules comprising, or alternatively, consisting of, a polynucleotide encoding PSGR having the amino acid sequence shown in FIGS. 1A–B (SEQ ID NO:2); or the amino acid sequence encoded by the cDNA clone (HPRAJ70) deposited as American Type Culture Collection ("ATCC") Deposit No. 97131 on Apr. 18, 1995. The ATCC is located at 10801 University Boulevard, Manassas, Va. 20110–2209.

The present invention further provides isolated nucleic acid molecules comprising, or alternatively consisting of, a polynucleotide encoding PSGR having the amino acid sequence shown in FIGS. 2A–B (SEQ ID NO:4).

The present invention also relates to recombinant vectors, which include the isolated nucleic acid molecules of the present invention, and to host cells containing the recombinant vectors, as well as to methods of making such vectors and host cells and for using them for production of PSGR polypeptides or peptides by recombinant techniques.

The invention further provides an isolated PSGR polypeptide having an amino acid sequence encoded by a polynucleotide described herein.

The present invention also provides diagnostic assays such as quantitative and diagnostic assays for detecting levels of PSGR protein. Thus, for instance, a diagnostic assay in accordance with the invention for detecting overexpression of PSGR, or soluble form thereof, compared to normal control tissue samples may be used to detect the presence of tumors.

GPCR genes and gene products are potential causative agents of disease (Spiegel et al., J. Clin. Invest. 92:1119–1125 (1993); McKusick et al., J. Med. Genet. 30:1–26 (1993)). Specific defects in the rhodopsin gene and the V2 vasopressin receptor gene have been shown to cause various forms of retinitis pigmentosum (Nathans et al., Ann. Rev. Genet. 26:403–424 (1992)), nephrogenic diabetes insipidus (Holtzman et al., Hum. Mol. Genet. 2:1201–1204 (1993)). These receptors are of critical importance to both the central nervous system and peripheral physiological processes. Evolutionary analyses suggests that the ancestor of these proteins originally developed in concert with complex body plans and nervous systems.

Thus, the invention further provides cells which express the PSGR polypeptide with a candidate compound and its ligand, assaying for inhibiting PSGR mediated signalling induced by said ligand which involves administering to a cell which expresses the PSGR polypeptide an effective amount of a PSGR agonist capable of decreasing PSGR mediated signalling.

In a further aspect, the present invention is directed to a method for enhancing PSGR mediated signalling induced by its ligand which involves administering to a cell which expresses the PSGR polypeptide an effective amount of a PSGR agonist or antagonist capable of increasing PSGR mediated signalling.

Whether any candidate "agonist" or "antagonist" of the present invention can enhance or inhibit PSGR mediated signalling can be determined using art-known G-protein coupled ligand/receptor cellular response assays, including those well known in the art. Thus, in a further aspect, a screening method is provided for determining whether a candidate agonist or antagonist is capable of enhancing or inhibiting a PSGR mediated cellular response to a ligand. The method involves contacting cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By the invention, a cell expressing the PSGR polypeptide can be contacted with either an endogenous or exogenously administered ligand.

BRIEF DESCRIPTION OF THE FIGURES

FIGS. 1A–B shows the nucleotide (SEQ ID NO: 1) and deduced amino acid sequence (SEQ ID NO:2) of the PSGR protein. It is predicted that amino acids 1 to 21 constitute the amino terminal extracellular domain and amino acids 294 to 320 constitute the carboxy terminal intracellular domain. The region spanning the entire transmembrane domain is from about amino acids 22 to about amino acid 293. Specifically, the seven transmembrane segments are as follows: from about amino acid 22 to about amino acid 42, from about amino acid 56 to about amino acid 76, from about amino acid 99 to about amino acid 119, from about amino acid 142 to about amino acid 162, from about amino acid 198 to about amino acid 218, from about amino acid 241 to about amino acid 261, and from about amino acid 273 to about amino acid 293. The amino acids corresponding to the three extracellular loops are as follows: from about amino acid 77 to about 98, from about amino acid 163 to about amino acid 197, and from about amino acid 262 to about amino acid 272. The amino acids corresponding to the three intracellular loops are as follows: from about amino acid 43 to about amino acid 55, from about amino acid 120 to about amino acid 141, and from about amino acid 219 to about amino acid 240. The conserved intracellular G protein signature sequence, "DRY" is found at amino acids 120 to 122. This sequence is implicated in signal transduction.

FIGS. 2A–B shows the nucleotide (SEQ ID NO:3) and deduced amino acid sequence (SEQ ID NO:4) of a variant PSGR protein. It is predicted that amino acids 1 to 21 constitute the amino terminal extracellular domain and amino acids 294 to 320 constitute the carboxy terminal intracellular domain. The region spanning the entire transmembrane domain is from about amino acids 22 to about amino acid 293. Specifically, the seven transmembrane segments are as follows: from about amino acid 22 to about amino acid 42, from about amino acid 56 to about amino acid 76, from about amino acid 99 to about amino acid 119, from about amino acid 142 to about amino acid 162, from about amino acid 198 to about amino acid 218, from about amino acid 241 to about amino acid 261, and from about amino acid 273 to about amino acid 293. The amino acids corresponding to the three extracellular loops are as follows: from about amino acid 77 to about 98, from about amino acid 163 to about amino acid 197, and from about amino acid 262 to about amino acid 272. The amino acids corresponding to the three intracellular loops are as follows: from about amino acid 43 to about amino acid 55, from about amino acid 120 to about amino acid 141, and from about amino acid 219 to about amino acid 240. The conserved intracellular G protein signature sequence, "DRY" is found at amino acids 120 to 122. This sequence is implicated in signal transduction.

FIG. 3 shows the regions of similarity between the amino acid sequences of the PSGR (SEQ ID NO:2), and the human HGMP071 olfactory receptor (SEQ ID NO:5). Regions of identity are shaded.

Figure 4:
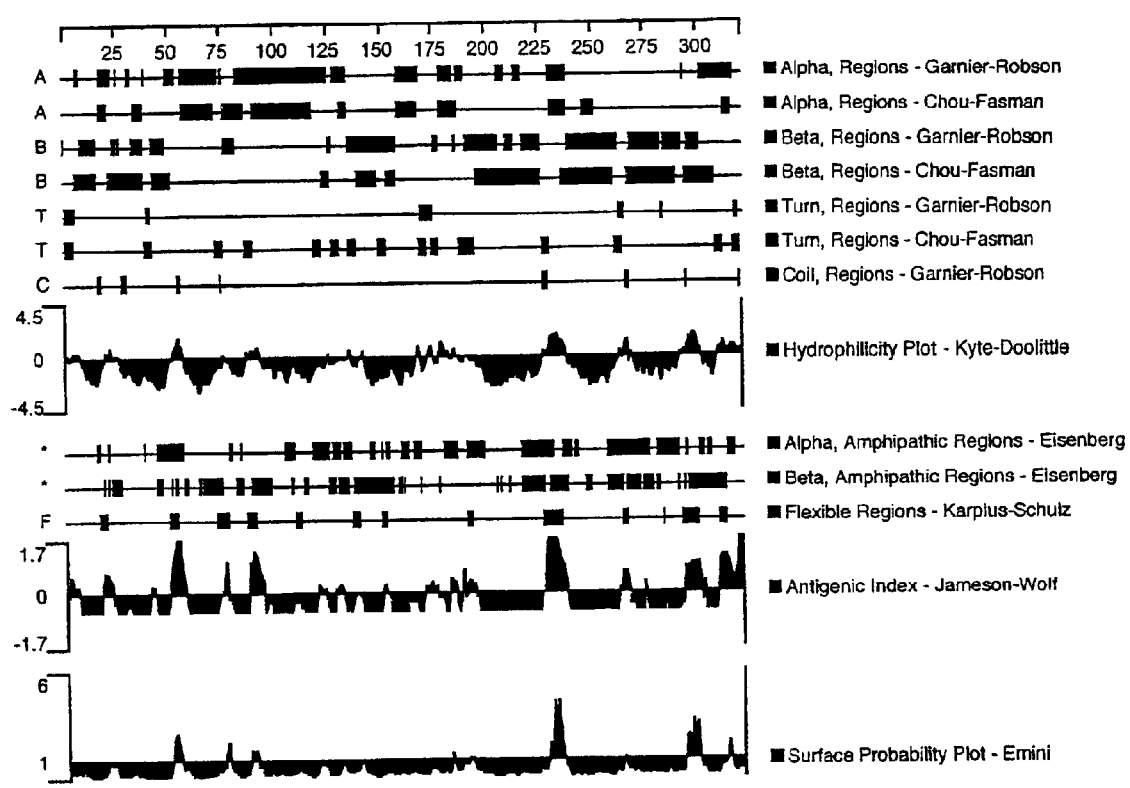
FIG. 4 shows an analysis of the PSGR amino acid sequence. Alpha, beta, turn and coil regions; hydrophilicity and hydrophobicity; amphipathic regions; flexible regions; antigenic index and surface probability are shown, and all were generated using the default settings. In the "Antigenic Index or Jameson-Wolf" graph, the positive peaks indicate locations of the highly antigenic regions of the PSGR protein, i.e., regions from which epitope-bearing peptides of the invention can be obtained. The domains defined by these graphs are contemplated by the present invention. In the "Antigenic Index-Jameson-Wolf" graph, amino acid residues T-50 to H-55, D-87 to E-90, L-227 to R-234, and S-309 to D-313 in FIGS. 1A–B (SEQ ID NO:2) correspond to the shown highly antigenic regions of the PSGR protein.

The data presented in FIG. 4 are also represented in tabular form in Table I. The columns are labeled with the headings "Res", "Position", and Roman Numerals I–XIII. The column headings refer to the following features of the amino acid sequence presented in FIG. 4, and Table I: "Res": amino acid residue of SEQ ID NO:2 and FIGS. 1A–B; "Position": position of the corresponding residue within SEQ ID NO:2 and FIGS. 1A–B; I: Alpha, Regions—Gamier-Robson; II: Alpha, Regions—Chou-Fasman; III: Beta, Regions-Garnier—Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Alpha, Amphipathic Regions—Eisenberg; X: Beta, Amphipathic Regions—Eisenberg; XI: Flexible Regions—Karplus-Schulz; XII: Antigenic Index—Jameson-Wolf; and XIII: Surface Probability Plot—Emini.

DETAILED DESCRIPTION OF THE PREFERRED EMBODIMENTS

The present invention provides isolated nucleic acid molecules comprising, or alternatively consisting of, a polynucleotide encoding a PSGR polypeptide having the amino acid sequence shown in FIGS. 1A–B (SEQ ID NO:2). The PSGR polypeptides of the present invention share sequence homology with G protein coupled odorant receptor family members (FIG. 3). Specifically, PSGR shows the closest similarity to a human OR gene, HPFH1OR. The nucleotide sequence shown in FIGS. 1A–B (SEQ ID NO:1) was obtained by sequencing the cDNA clone HPRAJ70, which was deposited at the American Type Culture Collection, and given Accession Number 97131. The deposited HPRAJ70 clone is inserted in the UniZAP XR plasmid (Stratagene Cloning Systems, Inc.) using the EcoRI and XhoI restriction endonuclease cleavage sites.

The present invention further provides nucleic acid molecules comprising, or alternatively consisting of, a polynucleotide encoding a PSGR polypeptide having the amino acid sequence shown in FIGS. 2A–B (SEQ ID NO:4).

Nucleic Acid Molecules

The determined nucleotide sequence of the PSGR cDNA of (FIGS. 1A–B) SEQ ID NO: 1 contains an open reading frame of 963 nucleotide base pairs encoding a protein of about 320 amino acid residues, and a deduced molecular weight of about 35.4 kDa. The PSGR polypeptides of the invention share the greatest degree of homology with human G protein coupled odorant family. Specifically, PSGR showed the closest similarity to a human OR gene, HPFH1OR (SEQ ID NO:5) (see, FIG. 3), which was mapped to the beta-globin gene cluster on chromosome 11p15.5. The PSGR protein contains seven trans-membrane domains between amino acid residues 24 to 293 in SEQ ID NO:2 that are characteristic of G-protein coupled receptors.

The determined nucleotide sequence of the PSGR genomic clone of FIGS. 2A–B (SEQ ID NO:3) is identical to the PSGR cDNA sequence of FIGS. 1A–B (SEQ ID NO: 1) with the following substitutions: at nucleotide 33 a 'T' residue in SEQ ID NO:3 replaces a 'G' residue in SEQ ID NO:1, at nucleotide 116 a 'T' residue in SEQ ID NO:3 replaces a 'G' residue in SEQ ID NO:1, and at nucleotide 277 a 'T' residue in SEQ ID NO:3 replaces an 'A' residue in SEQ ID NO:1.

The term "PSGR polynucleotides" as used herein is meant to encompass both of the above described PSGR polynucleotide variants and fragments thereof. The term "PSGR polypeptides" as used herein is meant to encompass polypeptides encoded by the above described variants, and fragments thereof.

To examine the tissue distribution of PSGR, Northern blot analysis was performed. Of 23 different human tissue mRNA analyzed, a 2.7 kb mRNA transcript specifically hybridizing to the PSGR cDNA was detected only in prostate tissue. In situ RNA hybridization analysis of PSGR expression in prostate tissues revealed the expression of PSGR predominantly localized to epithelial cells of gland (data not shown).

It will further be appreciated that, the domains described herein have been predicted by computer analysis, and accordingly, that depending on the analytical criteria used for identifying various functional domains, the exact "address" of, for example, the extracellular domain, intracellular domain, and transmembrane domain of PSGR may differ slightly. For example, the exact location of the PSGR transmembrane domains in FIGS. 1A–B (SEQ ID NO:2) or FIGS. 2A–B (SEQ ID NO:4) (e.g., the address may "shift" by about 1 to about 20 residues, more likely about 1 to about 5 residues) depending on the criteria used to define the domain. In any event, as discussed further below, the invention further provides polypeptides having various residues deleted from the N-terminus and/or C-terminus of the complete PSGR, including polypeptides lacking one or more amino acids from the N-termini of the PSGR extracellular domains described herein, which constitute soluble forms of the extracellular domain of the PSGR polypeptides respectively.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically. However, a nucleic acid molecule contained in a clone that is a member of a mixed clone library (e.g., a genomic or cDNA library) and that has not been isolated from other clones of the library (e.g., in the form of a homogeneous solution containing the clone without other members of the library) or a chromosome isolated or removed from a cell or a cell lysate (e.g., a "chromosome spread", as in a karyotype), is not "isolated" for the purposes of this invention.

Isolated nucleic acid molecules of the present invention include DNA molecules comprising an open reading frame (ORF) shown in FIGS. 1A–B (SEQ ID NO:1); DNA molecules comprising the coding sequence for the complete (full-length) PSGR protein shown in FIGS. 1A–B (SEQ ID NO:2); DNA molecules comprising an open reading frame (ORF) shown in FIGS. 2A–B (SEQ ID NO:3); DNA molecules comprising the coding sequence for the complete (full-length) PSGR protein shown in FIGS. 2A–B (SEQ ID NO:4); and DNA molecules which comprise a sequence substantially different from those described above, but which, due to the degeneracy of the genetic code, still encode the PSGR protein. Of course, the genetic code is well known in the art. Thus, it would be routine for one skilled in the art to generate such degenerate variants.

In another aspect, the invention provides isolated nucleic acid molecules having a polynucleotide sequence encoding the PSGR polypeptide having an amino acid sequence as encoded by a cDNA clone contained in the plasmid deposited as ATCC Deposit No. 97131. The invention further provides an isolated nucleic acid molecule having the nucleotide sequence shown in FIGS. 1A–B (SEQ ID NO: 1), an isolated nucleic acid molecule having the nucleotide sequence shown in FIGS. 2A–B (SEQ ID NO:3), or a nucleic acid molecule having a sequence complementary to one of the above sequences. Such isolated molecules, particularly DNA molecules, are useful, for example, as probes for gene mapping by in situ hybridization with chromosomes, and for detecting expression of the PSGR gene in human tissue (e.g., in prostate tissue or prostate cancer tissue), for instance, by hybridization (e.g., Northern blot analysis) or histochemistry.

The present invention is further directed to fragments of the isolated nucleic acid molecules described herein. By a fragment of an isolated DNA molecule having the nucleotide sequence of the deposited cDNA or the nucleotide sequence shown in FIGS. 1A–B (SEQ ID NO:1) or the nucleotide sequence shown in FIGS. 2A–B (SEQ ID NO:3) is intended DNA fragments at least about 15nt, and more preferably at least about 20 nt, at least about 24 nt, still more preferably at least about 30 nt, and even more preferably, at least about 40 nt, at least about 50 nt, at least about 100 nt, at least about 150 nt, at least about 200 nt, at least about 250 nt, at least about 300 nt in length which are useful, for example, as diagnostic probes and primers as discussed herein. Of course, larger fragments 350–1500 nt in length are also useful according to the present invention, as are fragments corresponding to most, if not all, of the nucleotide sequence of the deposited cDNA plasmids, or as shown in FIGS. 1A–B (SEQ ID NO:1), or as shown in FIGS. 2A–B (SEQ ID NO:3), or the complementary strand thereto. By a fragment at least 20 nt in length, for example, is intended fragments which include 20 or more contiguous bases from the nucleotide sequence of the deposited cDNA or the nucleotide sequence as shown in FIGS. 1A–B (SEQ ID NO:1) or the nucleotide sequence as shown in FIGS. 2A–B (SEQ ID NO:3). In this context "about" includes the particularly recited size, larger or smaller by several (5, 4, 3, 2, or 1) nucleotides, at either terminus or at both termini.

Representative examples of PSGR polynucleotide fragments of the invention include, for example, fragments that comprise, or alternatively, consist of, a sequence from about nucleotide 274 to 336, 337 to 399, 400 to 438, 439 to 501, 502 to 567, 568 to 630, 631 to 696, 697 to 759, 760 to 864, 865 to 927, 928 to 993, 994 to 1056, 1057 to 1089, 1090 to 1152, 1153 to 1233 of FIGS. 1A–B (SEQ ID NO:1), or FIGS. 2A–B (SEQ ID NO:3) or the complementary strand thereto, or the cDNA contained in one of the deposited cDNA clones. In this context "about" includes the particularly recited ranges, larger or smaller by several (5, 4, 3, 2, or 1) nucleotides, at either terminus or at both termini.

Preferably, the polynucleotide fragments of the invention encode a polypeptide which demonstrates a PSGR functional activity. By a polypeptide demonstrating a PSGR "functional activity" is meant, a polypeptide capable of displaying one or more known functional activities associated with a full-length (complete) PSGR protein. Such functional activities include, but are not limited to, biological activity, antigenicity (ability to bind (or compete with a PSGR polypeptide for binding) to an anti-PSGR antibody), immunogenicity (ability to generate antibody which binds to a PSGR polypeptide), ability to form multimers with PSGR polypeptides of the invention, and ability to bind to a receptor or ligand for a PSGR polypeptide.

The functional activity of PSGR polypeptides, and fragments, variants derivatives, and analogs thereof, can be assayed by various methods.

For example, in one embodiment where one is assaying for the ability to bind or compete with full-length PSGR polypeptides for binding to anti-PSGR antibody various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a PSGR ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., *Microbiol. Rev.* 59:94–123 (1995). In another embodiment, physiological correlates of PSGR binding to its substrates (signal transduction) can be assayed.

In addition, assays described herein (and otherwise known in the art may routinely be applied to measure the ability of PSGR polypeptides and fragments, variants derivatives and analogs thereof to elicit PSGR related biological activity. For example, techniques described herein and otherwise known in the art may be applied or routinely modified to assay for the ability of the compositions of the invention to bind to the PSGR ligand or couple to G protein. Other methods will be known to the skilled artisan and are within the scope of the invention.

Preferred nucleic acid fragments of the present invention include nucleic acid molecules encoding a member selected from the group: a polypeptide comprising or alternatively, consisting of, the PSGR transmembrane domain I (amino acid residues from about 22 to about 42 in FIGS. 1A–B (SEQ ID NO:2) or FIGS. 2A–B (SEQ ID NO:4); a polypeptide comprising, or alternatively consisting of, the PSGR transmembrane domain II (amino acid residues from about 56 to about 76 in FIGS. 1A–B (SEQ ID NO:2) or FIGS. 2A–B (SEQ ID NO:4); a polypeptide comprising, or alternatively consisting of the PSGR transmembrane domain III (amino acid residues from about 99 to about 119 in FIGS. 1A–B (SEQ ID NO:2) or FIGS. 2A–B (SEQ ID NO:4); a polypeptide comprising, or alternatively consisting of, the PSGR transmembrane domain IV (amino acid residues from about 142 to about 162 in FIGS. 1A–B (SEQ ID NO:2) or FIGS. 2A–B (SEQ ID NO:4); a polypeptide comprising, or alternatively consisting of, the PSGR transmembrane domain V (amino acid residues from about 198 to about 218 in FIGS. 1A–B (SEQ ID NO:2) or FIGS. 2A–B (SEQ ID NO:4); a polypeptide comprising, or alternatively consisting of, the PSGR transmembrane domain VI (amino acid residues from about 241 to about 261 in FIGS. 1A–B (SEQ ID NO:2) or FIGS. 2A–B (SEQ ID NO:4); a polypeptide comprising, or alternatively consisting of, a polypeptide comprising, or alternatively consisting of, the PSGR transmembrane domain VII (amino acid residues from about 273 to about 293 in FIGS. 1A–B (SEQ ID NO:2) or FIGS. 2A–B (SEQ ID NO:4); a polypeptide comprising, or alternatively consisting of, the PSGR extracellular loop I (amino acid residues from about 77 to about 98 in FIGS. 1A–B (SEQ ID NO:2) or FIGS. 2A–B (SEQ ID NO:4); a polypeptide comprising, or alternatively consisting of, the PSGR extracellular loop II (amino acid residues from about 163 to about 197 in FIGS. 1A–B (SEQ ID NO:2) or FIGS. 2A–B (SEQ ID NO:4); a polypeptide comprising, or alternatively consisting of, the PSGR extracellular loop III (amino acid residues from about 262 to about 272 in FIGS. 1A–B (SEQ ID NO:2) or FIGS. 2A–B (SEQ ID NO:4); a polypeptide comprising, or alternatively consisting of, the PSGR intracellular loop I (amino acid residues from about 43 to about 55 in FIGS. 1A–B (SEQ ID NO:2) or FIGS. 2A–B (SEQ ID NO:4); a polypeptide comprising, or alternatively consisting of, the PSGR intracellular loop II (amino acid residues from about 120 to about 141 in FIGS. 1A–B (SEQ ID NO:2) or FIGS. 2A–B (SEQ ID NO:4); and/or a polypeptide comprising, or alternatively consisting of, the PSGR intracellular loop II (amino acid residues from about 219 to about 240 in FIGS. 1A–B (SEQ ID NO:2) or FIGS. 2A–B (SEQ ID NO:4). Since the location of these domains have been predicted by computer analysis, one of ordinary skill would appreciate that the amino acid residues constituting these domains may vary slightly (e.g., by about 1 to 15 amino acid residues) depending on the criteria used to define each domain.

Preferred nucleic acid fragments of the invention encode a full-length PSGR polypeptide lacking the nucleotides encoding the amino terminal methionine in FIGS. 1A–B (SEQ ID NO:2) or FIGS. 2A–B (SEQ ID NO:4), as it is known that the methionine is cleaved naturally and such sequences may be useful in genetically engineering PSGR expression vectors. Polypeptides encoded by such polynucleotides are also contemplated by the invention.

Preferred nucleic acid fragments of the present invention further include nucleic acid molecules encoding epitope-bearing portions of the PSGR receptor proteins. In particular, such nucleic acid fragments of the present invention include nucleic acid molecules encoding: a polypeptide comprising amino acid residues from about 50 to about 55 in FIGS. 1A–B (SEQ ID NO:2) or FIGS. 2A–B (SEQ ID NO:4); a polypeptide comprising amino acid residues from about 87 to about 90 in FIGS. 1A–B (SEQ ID NO:2) or FIGS. 2A–B (SEQ ID NO:4); a polypeptide comprising amino acid residues from about 227 to about 234 in FIGS. 1A–B (SEQ ID NO:2) or FIGS. 2A–B (SEQ ID NO:4); and a polypeptide comprising amino acid residues from about 309 to about 313 in FIGS. 1A–B (SEQ ID NO:2) or FIGS. 2A–B (SEQ ID NO:4). In this context the inventors have determined that the above polypeptide fragments are antigenic regions of the PSGR proteins. Methods for determining other such epitope-bearing portions of the PSGR proteins are described in detail below.

In additional embodiments, the polynucleotides of the invention encode functional attributes of PSGR. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of PSGR.

The data representing the structural or functional attributes of PSGR set forth in FIG. 4 and/or Table I, as described above, was generated using the various modules and algorithms of the DNA*STAR set on default parameters. In a preferred embodiment, the data presented in columns VIII, XII, and XIII of Table I can be used to determine regions of PSGR which exhibit a high degree of potential for antigenicity. Regions of high antigenicity are determined from the data presented in columns VIII, XII, and/or XIII by choosing values which represent regions of the polypeptide which are likely to be exposed on the surface of the polypeptide in an environment in which antigen recognition may occur in the process of initiation of an immune response.

Certain preferred regions in these regards are set out in FIG. 4, but may, as shown in Table I, be represented or identified by using tabular representations of the data presented in FIG. 4. The DNA*STAR computer algorithm used to generate FIG. 4 (set on the original default parameters) was used to present the data in FIG. 4 in a tabular format (See Table I). The tabular format of the data in FIGS. 4 may be used to easily determine specific boundaries of a preferred region.

The above-mentioned preferred regions set out in FIG. 4 and in Table I include, but are not limited to, regions of the aforementioned types identified by analysis of the amino acid sequences set out in FIGS. 1A–B. As set out in FIG. 4 and in Table I, such preferred regions include Garnier-Robson alpha-regions, beta-regions, turn-regions, and coil-regions, Chou-Fasman alpha-regions, beta-regions, and turn-regions, Kyte-Doolittle hydrophilic regions, Eisenberg alpha- and beta-amphipathic regions, Karplus-Schulz flexible regions, Jameson-Wolf regions of high antigenic index and Emini surface-forming regions.

TABLE I

| Res | Position | I | II | III | IV | V | VI | VII | VIII | IX | X | XI | XII | XIII |
|---|---|---|---|---|---|---|---|---|---|---|---|---|---|---|
| Met | 1 | . | . | B | . | . | . | . | 0.08 | . | . | . | −0.10 | 0.36 |
| Ser | 2 | . | . | . | . | T | T | . | −0.23 | . | . | . | 0.50 | 0.45 |
| Ser | 3 | . | . | . | . | T | T | . | −0.16 | . | . | . | 0.20 | 0.30 |
| Cys | 4 | . | . | . | . | T | T | . | 0.20 | . | . | . | 0.20 | 0.44 |
| Asn | 5 | . | . | . | . | T | T | . | 0.00 | . | . | . | 0.20 | 0.45 |
| Phe | 6 | . | . | . | B | T | . | . | 0.29 | . | . | . | −0.20 | 0.34 |
| Thr | 7 | A | . | . | B | . | . | . | −0.08 | . | . | . | −0.60 | 0.91 |
| His | 8 | A | . | . | B | . | . | . | −0.63 | . | . | . | −0.60 | 0.30 |
| Ala | 9 | . | . | B | B | . | . | . | −0.78 | . | . | . | −0.60 | 0.26 |
| Thr | 10 | . | . | B | B | . | . | . | −1.67 | . | . | . | −0.60 | 0.15 |
| Cys | 11 | . | . | B | B | . | . | . | −1.31 | . | . | . | −0.60 | 0.08 |
| Val | 12 | . | . | B | B | . | . | . | −1.89 | . | . | . | −0.60 | 0.08 |
| Leu | 13 | . | . | B | B | . | . | . | −2.07 | . | . | . | −0.60 | 0.04 |
| Ile | 14 | . | . | B | B | . | . | . | −1.82 | . | . | . | −0.60 | 0.11 |
| Gly | 15 | . | . | B | B | . | . | . | −2.32 | . | . | . | −0.60 | 0.14 |
| Ile | 16 | . | . | B | B | . | . | . | −1.66 | * | . | . | −0.60 | 0.14 |
| Pro | 17 | . | . | . | . | . | . | C | −0.76 | * | . | F | 0.25 | 0.35 |
| Gly | 18 | A | A | . | . | . | . | C | −0.53 | . | . | F | 0.65 | 0.70 |
| Leu | 19 | A | A | . | . | . | . | . | 0.32 | . | . | F | 0.60 | 1.01 |
| Glu | 20 | A | A | . | . | . | . | . | −0.03 | . | . | F | 0.45 | 0.89 |
| Lys | 21 | A | A | . | . | . | . | . | 0.57 | * | * | . | 0.30 | 0.78 |
| Ala | 22 | A | . | . | B | . | . | . | −0.08 | . | . | . | −0.30 | 0.99 |

TABLE I-continued

| Res | Position | I | II | III | IV | V | VI | VII | VIII | IX | X | XI | XII | XIII |
|---|---|---|---|---|---|---|---|---|---|---|---|---|---|---|
| His | 23 | A | . | . | B | . | . | . | −0.08 | . | * | . | −0.30 | 0.43 |
| Phe | 24 | . | . | B | B | . | . | . | 0.03 | . | * | . | −0.60 | 0.21 |
| Trp | 25 | . | . | B | B | . | . | . | −0.18 | . | * | . | −0.60 | 0.18 |
| Val | 26 | A | . | . | B | . | . | . | −1.03 | . | * | . | −0.60 | 0.21 |
| Gly | 27 | . | . | B | B | . | . | . | −1.26 | . | * | . | −0.60 | 0.20 |
| Phe | 28 | . | . | . | B | . | . | C | −1.52 | . | . | . | −0.40 | 0.15 |
| Pro | 29 | . | . | . | B | . | . | C | −1.42 | . | . | . | −0.40 | 0.28 |
| Leu | 30 | . | . | . | B | . | . | C | −1.38 | . | . | . | −0.40 | 0.28 |
| Leu | 31 | A | . | . | B | . | . | . | −1.38 | . | . | . | −0.60 | 0.50 |
| Ser | 32 | A | . | . | B | . | . | . | −1.89 | . | . | . | −0.60 | 0.24 |
| Met | 33 | . | . | B | B | . | . | . | −1.78 | . | . | . | −0.60 | 0.22 |
| Tyr | 34 | . | A | B | B | . | . | . | −2.17 | . | . | . | −0.60 | 0.27 |
| Val | 35 | . | A | B | B | . | . | . | −2.02 | . | . | . | −0.60 | 0.20 |
| Val | 36 | . | A | B | B | . | . | . | −1.56 | . | . | . | −0.60 | 0.11 |
| Ala | 37 | . | A | B | B | . | . | . | −1.26 | . | . | . | −0.60 | 0.07 |
| Met | 38 | . | A | B | B | . | . | . | −1.32 | * | . | . | −0.60 | 0.15 |
| Cys | 39 | A | . | . | . | . | . | T | −1.97 | . | . | . | −0.20 | 0.10 |
| Gly | 40 | . | . | . | . | . | T | T | −1.97 | . | . | . | 0.20 | 0.07 |
| Asn | 41 | . | . | . | . | . | T | T | −1.97 | . | . | . | 0.20 | 0.05 |
| Cys | 42 | . | . | B | . | . | . | T | −2.08 | . | . | . | −0.20 | 0.08 |
| Ile | 43 | . | . | B | B | B | . | . | −2.37 | . | . | . | −0.60 | 0.07 |
| Val | 44 | . | . | B | B | B | . | . | −2.56 | * | * | . | −0.60 | 0.03 |
| Val | 45 | . | . | B | B | B | . | . | −2.10 | * | * | . | −0.60 | 0.04 |
| Phe | 46 | . | . | B | B | B | . | . | −2.41 | * | * | . | −0.60 | 0.11 |
| Ile | 47 | . | . | B | B | B | . | . | −1.74 | * | . | . | −0.60 | 0.22 |
| Val | 48 | . | . | B | B | B | . | . | −0.74 | * | . | . | −0.30 | 0.51 |
| Arg | 49 | A | . | . | B | . | . | . | −0.19 | * | . | . | 0.45 | 1.14 |
| Thr | 50 | A | . | . | B | . | . | . | −0.14 | * | . | F | 1.13 | 2.19 |
| Glu | 51 | A | . | . | B | . | . | . | 0.52 | * | * | F | 1.36 | 2.43 |
| Arg | 52 | A | . | . | . | . | . | . | 0.82 | * | . | F | 1.79 | 1.69 |
| Ser | 53 | A | . | . | . | . | . | . | 1.47 | * | * | F | 1.72 | 1.18 |
| Leu | 54 | . | . | . | . | . | . | C | 0.76 | * | . | . | 2.30 | 1.05 |
| His | 55 | . | . | . | . | . | . | C | 0.82 | * | . | . | 1.02 | 0.53 |
| Ala | 56 | . | . | . | . | . | . | C | 0.01 | * | . | . | 0.49 | 0.62 |
| Pro | 57 | A | . | . | . | . | . | . | −0.80 | * | . | . | 0.06 | 0.62 |
| Met | 58 | A | A | . | . | . | . | . | −1.31 | . | * | . | −0.37 | 0.40 |
| Tyr | 59 | A | A | . | . | . | . | . | −1.17 | . | * | . | −0.60 | 0.32 |
| Leu | 60 | A | A | . | . | . | . | . | −1.73 | . | . | . | −0.60 | 0.11 |
| Leu | 62 | A | A | . | . | . | . | . | −2.33 | . | . | . | −0.60 | 0.06 |
| Cys | 63 | A | A | . | . | . | . | . | −2.32 | . | . | . | −0.60 | 0.07 |
| Met | 64 | A | A | . | . | . | . | . | −2.97 | . | . | . | −0.60 | 0.08 |
| Leu | 65 | A | A | . | . | . | . | . | −2.16 | . | * | . | −0.60 | 0.07 |
| Ala | 66 | A | A | . | . | . | . | . | −2.27 | . | . | . | −0.60 | 0.22 |
| Ala | 67 | A | A | . | . | . | . | . | −2.04 | . | * | . | −0.60 | 0.19 |
| Ile | 68 | A | A | . | . | . | . | . | −2.19 | . | * | . | −0.60 | 0.23 |
| Asp | 69 | A | A | . | . | . | . | . | −1.89 | . | * | . | −0.60 | 0.19 |
| Leu | 70 | A | A | . | . | . | . | . | −1.39 | . | * | . | −0.60 | 0.25 |
| Ala | 71 | A | A | . | . | . | . | . | −1.10 | . | * | . | −0.60 | 0.51 |
| Leu | 72 | A | A | . | . | . | . | . | −0.82 | . | * | . | −0.30 | 0.41 |
| Ser | 73 | A | . | . | . | . | T | . | −0.53 | . | * | F | −0.05 | 0.71 |
| Thr | 74 | A | . | . | . | . | T | . | −0.74 | . | * | F | −0.05 | 0.70 |
| Ser | 75 | . | . | . | . | . | T | C | 0.11 | . | * | F | 0.30 | 1.31 |
| Thr | 76 | A | . | . | . | . | T | . | −0.19 | . | . | F | 1.00 | 1.96 |
| Met | 77 | . | A | B | . | . | . | . | −0.19 | . | . | F | −0.15 | 0.95 |
| Pro | 78 | . | A | B | . | . | . | . | −0.48 | . | . | F | −0.15 | 0.59 |
| Lys | 79 | . | A | B | . | . | . | . | −0.98 | * | . | . | −0.30 | 0.41 |
| Ile | 80 | . | A | B | . | . | . | . | −1.38 | * | . | . | −0.60 | 0.34 |
| Leu | 81 | . | A | B | . | . | . | . | −1.36 | . | . | . | −0.60 | 0.19 |
| Ada | 82 | . | A | B | . | . | . | . | −1.46 | . | * | . | −0.60 | 0.10 |
| Leu | 83 | A | A | . | . | . | . | . | −1.24 | . | . | . | −0.60 | 0.12 |
| Phe | 84 | A | A | . | . | . | . | . | −1.59 | * | * | . | −0.60 | 0.25 |
| Trp | 85 | A | A | . | . | . | . | . | −0.59 | . | * | . | −0.60 | 0.33 |
| Phe | 86 | A | A | . | . | . | . | . | 0.22 | . | . | . | −0.60 | 0.79 |
| Asp | 87 | A | . | . | . | . | T | . | −0.08 | . | . | F | 1.00 | 1.58 |
| Ser | 88 | A | . | . | . | . | T | . | 0.43 | . | . | F | 1.00 | 1.06 |
| Arg | 89 | A | . | . | . | . | T | . | 0.24 | . | * | F | 1.30 | 1.63 |
| Glu | 90 | A | . | . | . | . | T | . | 0.53 | . | . | F | 1.15 | 0.69 |
| Ile | 91 | A | A | . | . | . | . | . | 0.64 | . | * | F | 0.75 | 0.89 |
| Ser | 92 | A | A | . | . | . | . | . | −0.02 | . | * | . | 0.60 | 0.46 |
| Ile | 93 | A | A | . | . | . | . | . | −0.53 | . | * | . | 0.30 | 0.14 |
| Glu | 94 | A | A | . | . | . | . | . | −0.96 | . | * | . | −0.60 | 0.17 |
| Ala | 95 | A | A | . | . | . | . | . | −0.96 | . | * | . | −0.30 | 0.18 |
| Cys | 96 | A | A | . | . | . | . | . | −0.67 | . | * | . | −0.30 | 0.44 |
| Leu | 97 | A | A | . | . | . | . | . | −1.07 | . | * | . | −0.30 | 0.25 |
| Thr | 98 | A | A | . | . | . | . | . | −0.88 | . | * | . | −0.60 | 0.22 |
| Gln | 99 | A | A | . | . | . | . | . | −1.77 | . | . | . | −0.60 | 0.35 |
| Met | 100 | A | A | . | . | . | . | . | −1.21 | . | . | . | −0.60 | 0.30 |

TABLE I-continued

| Res | Position | I | II | III | IV | V | VI | VII | VIII | IX | X | XI | XII | XIII |
|---|---|---|---|---|---|---|---|---|---|---|---|---|---|---|
| Phe | 101 | A | A | . | . | . | . | . | −1.13 | . | . | . | −0.60 | 0.28 |
| Phe | 102 | A | A | . | . | . | . | . | −1.13 | . | . | . | −0.60 | 0.16 |
| Ile | 103 | A | A | . | . | . | . | . | −1.12 | . | . | . | −0.60 | 0.14 |
| His | 104 | A | A | . | . | . | . | . | −1.71 | . | . | . | −0.60 | 0.21 |
| Ala | 105 | A | A | . | . | . | . | . | −2.00 | * | . | . | −0.60 | 0.25 |
| Leu | 106 | A | A | . | . | . | . | . | −1.30 | * | . | . | −0.60 | 0.25 |
| Ser | 107 | A | A | . | . | . | . | . | −0.90 | * | . | . | −0.30 | 0.31 |
| Ala | 108 | A | A | . | . | . | . | . | −0.32 | * | * | . | −0.30 | 0.42 |
| Ile | 109 | A | A | . | . | . | . | . | −1.18 | * | . | . | −0.30 | 0.73 |
| Glu | 110 | A | A | . | . | . | . | . | −1.40 | . | . | F | −0.15 | 0.38 |
| Ser | 111 | A | A | . | . | . | . | . | −1.40 | . | . | F | −0.45 | 0.31 |
| Thr | 112 | A | A | . | . | . | . | . | −1.69 | . | . | F | −0.45 | 0.37 |
| Ile | 113 | A | A | . | . | . | . | . | −1.70 | . | . | . | −0.60 | 0.21 |
| Leu | 114 | A | A | . | . | . | . | . | −1.40 | . | * | . | −0.60 | 0.16 |
| Leu | 115 | A | A | . | . | . | . | . | −2.10 | . | * | . | −0.60 | 0.11 |
| Ala | 116 | A | A | . | . | . | . | . | −1.80 | . | . | . | −0.60 | 0.14 |
| Met | 117 | A | A | . | . | . | . | . | −1.38 | . | . | . | −0.60 | 0.28 |
| Ala | 118 | A | A | . | . | . | . | . | −0.73 | * | . | . | −0.30 | 0.66 |
| Phe | 119 | A | . | . | . | . | T | . | −0.78 | * | . | . | 0.25 | 1.02 |
| Asp | 120 | A | . | . | . | . | T | . | −0.56 | * | . | . | 0.10 | 0.76 |
| Arg | 121 | A | . | . | . | . | T | . | −0.86 | * | . | . | 0.10 | 0.76 |
| Tyr | 122 | A | . | . | . | . | T | . | −0.92 | * | . | . | 0.10 | 0.62 |
| Val | 123 | A | . | . | B | . | . | . | −0.37 | * | . | . | −0.30 | 0.20 |
| Ala | 124 | A | . | . | B | . | . | . | 0.12 | * | . | . | −0.60 | 0.14 |
| Ile | 125 | A | . | . | B | . | . | . | −0.69 | * | * | . | −0.60 | 0.14 |
| Cys | 126 | . | . | B | B | . | . | . | −0.69 | . | * | . | −0.60 | 0.15 |
| His | 127 | . | . | B | . | . | T | . | −0.48 | * | * | . | 0.10 | 0.29 |
| Pro | 128 | A | . | . | . | . | T | . | −0.21 | * | * | . | 0.10 | 0.57 |
| Leu | 129 | A | . | . | . | . | T | . | −0.21 | * | . | . | 0.25 | 1.07 |
| Arg | 130 | A | . | . | . | . | T | . | −0.18 | * | * | . | 0.10 | 0.80 |
| His | 131 | A | A | . | . | . | . | . | −0.32 | . | * | . | −0.30 | 0.38 |
| Ala | 132 | A | A | . | . | . | . | . | −0.29 | * | * | . | −0.60 | 0.38 |
| Ala | 133 | A | A | . | . | . | . | . | −0.08 | * | * | . | −0.30 | 0.31 |
| Val | 134 | A | A | . | . | . | . | . | 0.42 | * | * | . | −0.60 | 0.37 |
| Leu | 135 | . | . | B | . | . | T | . | −0.54 | * | . | . | −0.20 | 0.53 |
| Asn | 136 | . | . | B | . | . | T | . | −0.82 | . | . | F | −0.05 | 0.39 |
| Asn | 137 | . | . | B | . | . | T | . | −0.82 | . | * | F | −0.05 | 0.76 |
| Thr | 138 | . | . | B | . | . | T | . | −0.23 | . | * | F | −0.05 | 0.93 |
| Val | 139 | . | . | B | B | . | . | . | −0.27 | . | * | F | −0.15 | 1.00 |
| Thr | 140 | . | . | B | B | . | . | . | 0.20 | . | * | . | −0.60 | 0.43 |
| Ala | 141 | . | . | B | B | . | . | . | −0.69 | . | * | . | −0.60 | 0.30 |
| Gln | 142 | . | . | B | B | . | . | . | −1.54 | . | * | . | −0.60 | 0.28 |
| Ile | 143 | . | . | B | B | . | . | . | −1.82 | . | * | . | −0.60 | 0.14 |
| Gly | 144 | . | . | B | B | . | . | . | −1.82 | . | * | . | −0.60 | 0.14 |
| Ile | 145 | . | . | B | B | . | . | . | −2.37 | * | * | . | −0.60 | 0.06 |
| Val | 146 | . | . | B | B | . | . | . | −1.67 | * | * | . | −0.60 | 0.07 |
| Ala | 147 | . | . | B | B | . | . | . | −2.01 | . | * | . | −0.60 | 0.13 |
| Val | 148 | . | . | B | B | . | . | . | −1.42 | . | * | . | −0.60 | 0.18 |
| Val | 149 | . | . | B | . | . | T | . | −1.89 | . | * | . | 0.10 | 0.33 |
| Arg | 150 | . | . | B | . | . | T | . | −1.70 | * | * | F | 0.25 | 0.27 |
| Gly | 151 | . | . | B | . | . | T | . | −1.54 | . | * | F | −0.05 | 0.32 |
| Ser | 152 | . | . | B | . | . | T | . | −1.66 | . | * | F | −0.05 | 0.37 |
| Leu | 153 | . | . | B | B | . | . | . | −1.01 | * | * | . | −0.60 | 0.16 |
| Phe | 154 | . | . | B | B | . | . | . | −0.97 | . | * | . | −0.60 | 0.25 |
| Phe | 155 | . | . | B | B | . | . | . | −1.29 | . | * | . | −0.60 | 0.16 |
| Phe | 156 | . | . | B | B | . | . | . | −1.76 | . | . | . | −0.60 | 0.29 |
| Pro | 157 | . | . | B | B | . | . | . | −2.27 | . | . | . | −0.60 | 0.28 |
| Leu | 158 | A | A | . | . | . | . | . | −2.34 | . | * | . | −0.60 | 0.27 |
| Pro | 159 | A | A | . | . | . | . | . | −1.60 | * | * | . | −0.60 | 0.22 |
| Leu | 160 | A | A | . | . | . | . | . | −0.79 | . | * | . | −0.60 | 0.28 |
| Leu | 161 | A | A | . | . | . | . | . | −0.90 | * | * | . | −0.30 | 0.66 |
| Ile | 162 | A | A | . | . | . | . | . | −1.28 | * | . | . | −0.30 | 0.35 |
| Lys | 163 | A | A | . | . | . | . | . | −1.17 | * | . | . | −0.30 | 0.43 |
| Arg | 164 | A | A | . | . | . | . | . | −1.62 | . | . | . | −0.30 | 0.45 |
| Leu | 165 | A | A | . | . | . | . | . | −0.84 | . | . | . | −0.30 | 0.35 |
| Ala | 166 | A | A | . | . | . | . | . | −0.33 | * | . | . | −0.30 | 0.24 |
| Phe | 167 | A | A | . | . | . | . | . | 0.56 | * | . | . | −0.60 | 0.16 |
| Cys | 168 | A | A | . | . | . | . | . | −0.34 | * | . | . | −0.60 | 0.32 |
| His | 169 | A | . | . | . | . | T | . | −1.27 | * | * | . | −0.20 | 0.23 |
| Ser | 170 | . | . | . | . | T | T | . | −0.76 | . | . | . | 0.20 | 0.22 |
| Asn | 171 | . | . | . | . | T | T | . | −0.20 | . | . | . | 0.20 | 0.55 |
| Val | 172 | . | . | . | . | T | T | . | 0.20 | . | . | . | 0.20 | 0.55 |
| Leu | 173 | . | . | . | . | T | . | . | 0.62 | . | . | . | 0.30 | 0.55 |
| Ser | 174 | . | . | . | . | T | . | . | −0.01 | . | . | . | 0.00 | 0.54 |
| His | 175 | . | . | . | . | T | T | . | −0.57 | . | . | . | 0.20 | 0.39 |
| Ser | 176 | . | . | B | . | . | T | . | −0.60 | . | . | . | −0.20 | 0.35 |
| Tyr | 177 | . | . | B | . | . | T | . | 0.26 | . | . | . | −0.20 | 0.35 |

TABLE I-continued

| Res | Position | I | II | III | IV | V | VI | VII | VIII | IX | X | XI | XII | XIII |
|---|---|---|---|---|---|---|---|---|---|---|---|---|---|---|
| Cys | 178 | . | . | B | . | . | T | . | 1.07 | . | * | . | −0.20 | 0.45 |
| Val | 179 | A | A | . | . | . | . | . | 0.51 | . | . | . | −0.30 | 0.56 |
| His | 180 | A | A | . | . | . | . | . | −0.06 | * | . | . | −0.60 | 0.27 |
| Gln | 181 | A | A | . | . | . | . | . | 0.29 | * | . | . | −0.30 | 0.49 |
| Asp | 182 | A | A | . | . | . | . | . | −0.28 | * | . | . | 0.45 | 1.33 |
| Val | 183 | A | A | . | . | . | . | . | −0.20 | * | . | . | 0.30 | 0.80 |
| Met | 184 | A | A | . | . | . | . | . | 0.41 | * | . | . | 0.30 | 0.47 |
| Lys | 185 | A | A | . | . | . | . | . | −0.14 | * | . | . | −0.30 | 0.44 |
| Leu | 186 | . | A | B | . | . | . | . | −0.14 | * | . | . | −0.60 | 0.60 |
| Ala | 187 | A | A | . | . | . | . | . | −0.46 | . | . | . | −0.15 | 1.01 |
| Tyr | 188 | A | . | . | . | . | T | . | −0.41 | . | . | . | 0.70 | 0.73 |
| Ala | 189 | A | . | . | . | . | T | . | −0.02 | . | . | . | −0.20 | 0.73 |
| Asp | 190 | A | . | . | . | . | T | . | −0.07 | . | . | . | 0.25 | 1.12 |
| Thr | 191 | . | . | B | . | . | T | . | −0.11 | * | . | F | 0.40 | 1.14 |
| Leu | 192 | . | . | B | . | . | T | . | −0.38 | * | . | F | 0.25 | 0.84 |
| Pro | 193 | . | . | B | . | . | T | . | −0.38 | * | . | F | 0.25 | 0.37 |
| Asn | 194 | . | . | B | . | . | T | . | −0.13 | * | . | . | −0.20 | 0.41 |
| Val | 195 | . | . | B | . | . | T | . | −0.94 | * | . | . | −0.20 | 0.49 |
| Val | 196 | . | . | B | B | . | . | . | −0.94 | * | . | . | −0.60 | 0.26 |
| Tyr | 197 | . | . | B | B | . | . | . | −0.72 | * | . | . | −0.60 | 0.23 |
| Gly | 198 | . | . | B | B | . | . | . | −1.40 | * | . | . | −0.60 | 0.32 |
| Leu | 199 | . | . | B | B | . | . | . | −2.21 | * | . | . | −0.60 | 0.30 |
| Thr | 200 | . | . | B | B | . | . | . | −2.17 | . | . | . | −0.60 | 0.16 |
| Ala | 201 | . | . | B | B | . | . | . | −2.17 | . | . | . | −0.60 | 0.13 |
| Ile | 202 | . | . | B | B | . | . | . | −2.52 | . | . | . | −0.60 | 0.12 |
| Leu | 203 | . | . | B | B | . | . | . | −2.52 | . | . | . | −0.60 | 0.08 |
| Leu | 204 | . | . | B | B | . | . | . | −2.57 | . | . | . | −0.60 | 0.08 |
| Val | 205 | . | . | B | B | . | . | . | −2.26 | . | * | . | −0.60 | 0.08 |
| Met | 206 | A | . | B | B | . | . | . | −2.52 | . | . | . | −0.60 | 0.17 |
| Gly | 207 | A | . | . | B | . | . | . | −2.23 | . | * | . | −0.60 | 0.15 |
| Val | 208 | A | . | . | B | . | . | . | −2.12 | . | . | . | −0.60 | 0.20 |
| Asp | 209 | A | . | . | B | . | . | . | −2.20 | . | . | . | −0.60 | 0.18 |
| Val | 210 | . | . | B | B | . | . | . | −1.64 | . | . | . | −0.60 | 0.13 |
| Met | 211 | . | . | B | B | . | . | . | −1.86 | . | * | . | −0.60 | 0.23 |
| Phe | 212 | . | . | B | B | . | . | . | −1.81 | . | . | . | −0.60 | 0.11 |
| Ile | 213 | . | . | B | B | . | . | . | −1.20 | . | . | . | −0.60 | 0.20 |
| Ser | 214 | A | . | . | B | . | . | . | −1.90 | . | . | . | −0.60 | 0.32 |
| Leu | 215 | A | . | . | B | . | . | . | −1.86 | . | . | . | −0.60 | 0.32 |
| Ser | 216 | A | . | . | B | . | . | . | −2.14 | . | . | . | −0.60 | 0.38 |
| Tyr | 217 | A | . | . | B | . | . | . | −2.33 | * | * | . | −0.60 | 0.20 |
| Phe | 218 | . | . | B | B | . | . | . | −1.33 | * | * | . | −0.60 | 0.17 |
| Leu | 219 | . | . | B | B | . | . | . | −1.34 | * | * | . | −0.60 | 0.25 |
| Ile | 220 | . | . | B | B | . | . | . | −1.39 | * | * | . | −0.60 | 0.23 |
| Ile | 221 | . | . | B | B | . | . | . | −1.90 | * | * | . | −0.60 | 0.19 |
| Arg | 222 | . | . | B | B | . | . | . | −1.66 | * | * | . | −0.60 | 0.19 |
| Thr | 223 | . | . | B | B | . | . | . | −1.77 | * | * | . | −0.60 | 0.48 |
| Val | 224 | . | . | B | B | . | . | . | −1.17 | * | * | . | −0.60 | 0.57 |
| Leu | 225 | . | . | B | B | . | . | . | −0.58 | * | * | . | 0.00 | 0.45 |
| Gln | 226 | . | . | B | B | . | . | . | 0.36 | * | * | . | 0.00 | 0.42 |
| Leu | 227 | . | . | . | . | T | C | . | −0.06 | * | * | F | 1.50 | 1.12 |
| Pro | 228 | . | . | . | . | . | T | C | 0.26 | * | . | F | 2.40 | 1.82 |
| Ser | 229 | . | . | . | . | . | T | C | 1.22 | * | . | F | 3.00 | 1.82 |
| Lys | 230 | A | . | . | . | . | T | . | 1.44 | * | * | F | 2.50 | 4.32 |
| Ser | 231 | A | A | . | . | . | . | . | 1.49 | * | * | F | 1.80 | 2.82 |
| Glu | 232 | A | A | . | . | . | . | . | 1.71 | . | * | F | 1.50 | 4.21 |
| Arg | 233 | A | A | . | . | . | . | . | 1.22 | . | * | F | 1.20 | 2.13 |
| Ala | 234 | A | A | . | . | . | . | . | 1.18 | . | * | F | 0.90 | 1.37 |
| Lys | 235 | A | A | . | . | . | . | . | 0.82 | . | * | F | 0.75 | 0.79 |
| Ala | 236 | A | A | . | B | . | . | . | 0.46 | * | * | . | 0.30 | 0.58 |
| Phe | 237 | A | A | . | B | . | . | . | −0.40 | * | * | . | −0.30 | 0.31 |
| Gly | 238 | A | A | . | B | . | . | . | −0.81 | * | * | . | −0.60 | 0.11 |
| Thr | 239 | . | . | B | B | . | . | . | −0.26 | * | . | . | −0.60 | 0.15 |
| Cys | 240 | . | . | B | B | . | . | . | −1.19 | * | . | . | −0.60 | 0.24 |
| Val | 241 | . | . | B | B | . | . | . | −0.94 | . | . | . | −0.60 | 0.17 |
| Ser | 242 | . | . | B | B | . | . | . | −1.10 | * | . | . | −0.60 | 0.12 |
| His | 243 | . | . | B | B | . | . | . | −1.61 | * | . | . | −0.60 | 0.16 |
| Ile | 244 | . | . | B | B | . | . | . | −2.11 | . | . | . | −0.60 | 0.16 |
| Gly | 245 | . | . | B | B | . | . | . | −2.03 | . | . | . | −0.60 | 0.10 |
| Val | 246 | . | A | B | B | . | . | . | −1.88 | . | . | . | −0.60 | 0.07 |
| Val | 247 | . | A | B | B | . | . | . | −1.82 | . | * | . | −0.60 | 0.09 |
| Leu | 248 | . | A | B | B | . | . | . | −2.64 | . | * | . | −0.60 | 0.14 |
| Ala | 249 | . | A | B | B | . | . | . | −1.97 | . | * | . | −0.60 | 0.14 |
| Phe | 250 | . | A | B | B | . | . | . | −2.43 | . | . | . | −0.60 | 0.30 |
| Tyr | 251 | . | A | B | B | . | . | . | −2.47 | . | . | . | −0.60 | 0.30 |
| Val | 252 | . | . | B | B | . | . | . | −1.96 | . | . | . | −0.60 | 0.21 |
| Pro | 253 | . | . | B | B | . | . | . | −1.96 | . | . | . | −0.60 | 0.24 |
| Leu | 254 | . | . | B | B | . | . | . | −1.67 | . | . | . | −0.60 | 0.12 |

TABLE I-continued

| Res | Position | I | II | III | IV | V | VI | VII | VIII | IX | X | XI | XII | XIII |
|---|---|---|---|---|---|---|---|---|---|---|---|---|---|---|
| Ile | 255 | . | . | B | B | . | . | . | -1.82 | . | . | . | -0.60 | 0.22 |
| Gly | 256 | . | . | B | B | . | . | . | -2.43 | . | . | . | -0.60 | 0.11 |
| Leu | 257 | . | . | B | B | . | . | . | -1.61 | * | . | . | -0.60 | 0.10 |
| Ser | 258 | . | . | B | B | . | . | . | -1.29 | * | * | . | -0.60 | 0.19 |
| Vat | 259 | . | . | B | B | . | . | . | -1.18 | * | * | . | -0.30 | 0.37 |
| Val | 260 | . | . | B | B | . | . | . | -0.63 | * | * | . | -0.60 | 0.39 |
| His | 261 | . | . | B | . | . | T | . | -0.29 | * | * | . | 0.10 | 0.29 |
| Arg | 262 | . | . | B | . | . | T | . | 0.22 | * | * | . | 0.10 | 0.62 |
| Phe | 263 | . | . | . | . | T | T | . | -0.29 | * | * | . | 0.65 | 1.13 |
| Gly | 264 | . | . | . | . | T | T | . | 0.53 | * | * | F | 0.65 | 0.68 |
| Asn | 265 | . | . | . | . | T | . | . | 1.18 | * | . | F | 0.45 | 0.48 |
| Ser | 266 | . | . | . | . | . | . | C | 0.32 | * | * | F | -0.05 | 0.85 |
| Leu | 267 | . | . | . | B | . | . | C | -0.64 | * | * | . | -0.40 | 0.60 |
| His | 268 | . | . | . | B | . | . | C | 0.17 | * | * | . | -0.40 | 0.28 |
| Pro | 269 | . | . | B | B | . | . | . | -0.34 | * | * | . | -0.30 | 0.41 |
| Ile | 270 | . | . | B | B | . | . | . | -1.20 | * | * | . | -0.60 | 0.36 |
| Vat | 271 | . | . | B | B | . | . | . | -1.50 | * | * | . | -0.60 | 0.20 |
| Arg | 272 | . | . | B | B | . | . | . | -1.03 | * | * | . | -0.60 | 0.13 |
| Vat | 273 | . | . | B | B | . | . | . | -1.00 | * | * | . | -0.60 | 0.18 |
| Vat | 274 | . | . | B | B | . | . | . | -1.68 | * | . | . | 0.30 | 0.40 |
| Met | 275 | . | . | B | B | . | . | . | -1.03 | * | * | . | -0.30 | 0.14 |
| Gly | 276 | . | . | B | B | . | . | . | -0.99 | * | * | . | -0.60 | 0.31 |
| Asp | 277 | . | . | B | B | . | . | . | -1.91 | * | . | . | -0.60 | 0.34 |
| Ile | 278 | . | . | B | B | . | . | . | -1.87 | . | * | . | -0.60 | 0.28 |
| Tyr | 279 | . | . | B | B | . | . | . | -1.22 | . | * | . | -0.60 | 0.24 |
| Leu | 280 | . | . | B | B | . | . | . | -0.83 | . | . | . | -0.60 | 0.22 |
| Leu | 281 | . | . | B | B | . | . | . | -1.34 | * | * | . | -0.60 | 0.48 |
| Leu | 282 | . | . | B | B | . | . | . | -2.23 | * | * | . | -0.60 | 0.23 |
| Pro | 283 | . | . | B | B | . | . | . | -1.34 | * | . | . | -0.60 | 0.19 |
| Pro | 284 | . | . | . | B | T | . | . | -1.31 | * | . | F | -0.05 | 0.38 |
| Vat | 285 | . | . | B | B | . | . | . | -1.39 | * | . | . | -0.60 | 0.71 |
| Ile | 286 | . | . | B | B | . | . | . | -1.47 | * | . | . | -0.60 | 0.32 |
| Asn | 287 | . | . | B | B | . | . | . | -0.90 | * | . | . | -0.60 | 0.15 |
| Pro | 288 | . | . | B | B | . | . | . | -1.03 | * | . | . | -0.60 | 0.31 |
| Ile | 289 | . | . | B | B | . | . | . | -1.41 | * | . | . | -0.60 | 0.43 |
| Ile | 290 | . | . | B | B | . | . | . | -0.51 | * | . | . | -0.60 | 0.27 |
| Tyr | 291 | . | . | B | . | . | . | . | 0.07 | * | * | . | -0.40 | 0.35 |
| Gly | 292 | . | . | B | . | . | . | . | 0.11 | . | . | . | -0.40 | 0.73 |
| Ala | 293 | . | . | B | . | . | . | . | 0.32 | . | . | F | 0.80 | 2.07 |
| Lys | 294 | A | . | . | . | . | . | . | 0.32 | . | * | F | 0.80 | 2.29 |
| Thr | 295 | . | . | . | B | . | . | C | 1.32 | * | . | F | 0.80 | 1.62 |
| Lys | 296 | . | . | B | B | . | . | . | 1.26 | . | * | F | 0.90 | 3.15 |
| Gln | 297 | . | . | B | B | . | . | . | 1.71 | . | * | F | 0.90 | 2.27 |
| Ile | 298 | . | . | B | B | . | . | . | 1.44 | . | * | F | 0.90 | 3.08 |
| Arg | 299 | . | . | B | B | . | . | . | 0.59 | . | * | F | 0.90 | 1.14 |
| Thr | 300 | . | . | B | B | . | . | . | 0.31 | . | * | F | 0.45 | 0.54 |
| Arg | 301 | . | . | B | B | . | . | . | -0.33 | * | * | . | -0.30 | 0.78 |
| Val | 302 | A | . | . | B | . | . | . | -1.03 | * | * | . | 0.30 | 0.40 |
| Leu | 303 | A | . | . | B | . | . | . | -0.10 | * | * | . | -0.60 | 0.24 |
| Ala | 304 | A | . | . | B | . | . | . | -1.10 | . | * | . | -0.30 | 0.24 |
| Met | 305 | A | . | . | B | . | . | . | -1.09 | * | * | . | -0.60 | 0.23 |
| Phe | 306 | A | . | . | B | . | . | . | -1.87 | * | * | . | -0.60 | 0.37 |
| Lys | 307 | A | . | . | B | . | . | . | -1.01 | . | * | . | -0.60 | 0.20 |
| Ile | 308 | A | . | . | B | . | . | . | -0.16 | . | * | . | -0.30 | 0.33 |
| Ser | 309 | A | . | . | . | . | T | . | 0.43 | . | * | . | 1.00 | 0.77 |
| Cys | 310 | A | . | . | . | . | T | . | 0.22 | . | * | F | 1.15 | 0.64 |
| Asp | 311 | A | . | . | . | . | T | . | 0.92 | . | * | F | 1.15 | 0.76 |
| Lys | 312 | A | . | . | . | . | T | . | 0.29 | . | * | F | 1.15 | 0.98 |
| Asp | 313 | A | A | . | . | . | . | . | 0.32 | . | * | F | 0.90 | 1.84 |
| Leu | 314 | A | A | . | . | . | . | . | 0.28 | * | . | . | 0.60 | 0.82 |
| Gln | 315 | A | A | . | . | . | . | . | 0.60 | * | . | . | 0.52 | 0.41 |
| Ala | 316 | A | A | . | . | . | . | . | 0.64 | * | . | . | 0.14 | 0.24 |
| Val | 317 | A | . | . | . | . | T | . | 0.21 | * | . | . | 0.76 | 0.58 |
| Gly | 318 | . | . | . | . | T | T | . | -0.18 | . | . | . | 1.98 | 0.43 |
| Gly | 319 | . | . | . | . | T | T | . | 0.24 | . | . | . | 2.20 | 0.54 |
| Lys | 320 | . | . | . | . | . | T | C | -0.14 | . | . | . | 1.78 | 0.94 |

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit No. 97131, or the complementary strand of nucleotides of SEQ ID NO:1, or the complementary strand of nucleotides of SEQ ID NO:3. By "stringent hybridization conditions" is intended overnight incubation at 42° C. in a solution comprising: 50% formamide, 5×SSC (750 mM NaCl, 75mM trisodium citrate), 50 mM sodium phosphate (pH 7.6), 5× Denhardt's solution, 10% dextran sulfate, and 20 g/ml denatured, sheared salmon sperm DNA, followed by washing the filters in 0.1×SSC at about 65° C. Polypeptides encoded by these nucleic acids are also encompassed by the invention.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful, for example, as diagnostic probes and primers as discussed above and in more detail below. In this context "about" includes the particularly recited size, larger or smaller by several (5, 4, 3, 2, or 1) nucleotides, at either terminus or at both termini.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A–B (SEQ ID NO:1).

Of course, a polynucleotide which hybridizes only to a poly A sequence (such as the 3' terminal poly(A) tract of the PSGR cDNA shown in FIGS. 1A–B (SEQ ID NO:1) or FIGS. 2A–B (SEQ ID NO:3), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone generated using oligo dT as a primer).

In specific embodiments, the polynucleotides of the invention are less than 110000 kb, 50000 kb, 10000 kb, 1000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

In further embodiments, polynucleotides of the invention comprise at least 15, at least 30, at least 50, at least 100, or at least 250, at least 500, or at least 1000 contiguous nucleotides of PSGR coding sequence, but consist of less than or equal to 107 kb, 75 kb, 50 kb, 30 kb, 25 kb, 20 kb, 15 kb, 10 kb, or 5 kb of genomic DNA that flanks the 5' or 3' coding nucleotide set forth in FIGS. 1A–B (SEQ ID NO: 1) or FIGS. 2A–B (SEQ ID NO:3). In further embodiments, polynucleotides of the invention comprise at least 15, at least 30, at least 50, at least 100, or at least 250, at least 500, or at least 1000 contiguous nucleotides of PSGR and/or coding sequence, but do not comprise all or a portion of any PSGR intron. In another embodiment, the nucleic acid comprising PSGR coding sequence does not contain coding sequences of a genomic flanking gene (i.e., 5' or 3' to the PSGR gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As indicated, nucleic acid molecules of the present invention which encode a PSGR polypeptide may include, but are not limited to, the coding sequence for the mature polypeptide, by itself; the coding sequence for the mature polypeptide and additional sequences, such as those encoding a leader or secretory sequence, such as a pre-, or pro- or prepro- protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, MRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86: 821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767–778 (1984). As discussed below, other such fusion proteins include the PSGR receptor fused to Fc at the N- or C-terminus.

The present invention further relates to variants of the nucleic acid molecules of the present invention, which encode portions, analogs, or derivatives of the PSGR receptor. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions which may involve one or more nucleotides. The variants may be altered in coding or non-coding regions or both. Alterations in the coding regions may produce conservative or non-conservative amino acid substitutions, deletions, or additions. Especially preferred among these are silent substitutions, additions, and deletions, which do not alter the properties and activities of the PSGR receptor or portions thereof. Also especially preferred in this regard are conservative substitutions.

Further embodiments of the invention include isolated nucleic acid molecules comprising, or alternatively consisting of, a polynucleotide having a nucleotide sequence at least 90% identical, and more preferably at least 95%, 96%, 97%, 98%, or 99% identical to: (a) a nucleotide sequence encoding the polypeptide having the amino acid sequence shown in FIGS. 1A–B (SEQ ID NO:2) or FIGS. 2A–B (SEQ ID NO:4); (b) a nucleotide sequence encoding the polypeptide having the amino acid sequence in FIGS. 1A–B (SEQ ID NO:2) or FIGS. 2A–B (SEQ ID NO:4), but lacking the amino terminal methionine; (c) a nucleotide sequence encoding the polypeptide having the amino acid sequence encoded by a cDNA clone contained in ATCC Deposit No. 97131; (d) a nucleotide sequence encoding the PSGR transmembrane domain I; (e) a nucleotide sequence encoding the PSGR transmembrane domain II; (f) a nucleotide sequence encoding the PSGR transmembrane domain II; (g) a nucleotide sequence encoding the PSGR transmembrane domain IV; (h) a nucleotide sequence encoding the PSGR transmembrane domain V; (i) a nucleotide sequence encoding the PSGR transmembrane domain VI; (j) a nucleotide sequence encoding the PSGR transmembrane domain VII; (k) a nucleotide sequence encoding one, two, three, four, five, six, or all seven of the PSGR transmembrane domains; (l) a nucleotide sequence encoding PSGR with one, two, three, four, five, six, or all seven of the transmembrane domains deleted; (m) a nucleotide sequence encoding PSGR extracellular loop I; (n) a nucleotide sequence encoding PSGR extracellular loop II; (o) a nucleotide sequence encoding PSGR extracellular loop III; (p) a nucleotide sequence encoding one, two, or all three of the PSGR extracellular loops; (q) a nucleotide sequence encoding PSGR intracellular loop I; (r) a nucleotide sequence encoding PSGR intracellular loop II; (s) a nucleotide sequence encoding PSGR intracellular loop III; and (t) a nucleotide sequence encoding any combination of thenucleotide sequences in (a), (b), (c), (d), (e), (f), (g), (h), (i), (j), (k), (l), (m), (n), (o), (p), (q), (r), (s) or (t) above. Polypeptides encoded by these polynucleotides are also encompassed by the invention.

In a specific embodiment, the invention also encompasses a nucleotide sequence complementary to any of the nucleotide sequences in (a), (b), (c), (d), (e), (f), (g), (h), (i), (j), (k), (l), (m), (n), (o), (p), (q), (r), (s) or (t) above.

By a polynucleotide having a nucleotide sequence at least, for example, 95% "identical" to a reference nucleotide sequence encoding a PSGR polypeptide is intended that the nucleotide sequence of the polynucleotide is identical to the reference sequence except that the polynucleotide sequence may include up to five mismatches per each 100 nucleotides of the reference nucleotide sequence encoding the PSGR polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mismatches of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire PSGR encoding nucleotide sequence shown in FIGS. 1A–B (SEQ ID NO:2) or FIGS. 2A–B (SEQ ID NO:4), or any PSGR polynucleotide fragment (e.g., a polynucleotide encoding the amino acid sequence of any of the PSGR N- and/or C- terminal deletions described herein), variant, derivative or analog, as described herein.

As a practical matter, whether any particular nucleic acid molecule is at least 90%, 95%, 96%, 97%, 98% or 99% identical to, for instance, the nucleotide sequence shown in FIGS. 1A–B (SEQ ID NO:2) or FIGS. 2A–B (SEQ ID NO:4) or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules comprising, or alternatively consisting of a nucleotide sequence at least 90%, 95%, 96%, 97%, 98%, or 99% identical to the nucleic acid sequence for example, shown in FIGS. 1A–B (SEQ ID NO:2) or FIGS. 2A–B (SEQ ID NO:4), or to the nucleic acid sequence of a deposited cDNA, irrespective of whether they encode a polypeptide having PSGR receptor activity. This is because even where a particular nucleic acid molecule does not encode a polypeptide having PSGR functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having PSGR activity include, inter alia: (1) isolating the PSGR gene or allelic variants thereof in a cDNA library; (2) in situ hybridization (e.g., "FISH") to metaphase chromosomal spreads to provide precise chromosomal location of the PSGR gene, as described in Verma et al., *Human Chromosomes: A Manual of Basic Techniques*, Pergamon Press, New York (1988); (3) Northern Blot analysis for detecting PSGR MRNA expression in specific tissues (e.g., normal prostate or prostate cancer tissues); and (4) in situ hybridization (e.g., histochemistry) for detecting PSGR MRNA expression in specific tissues (e.g., normal prostate or prostate cancer tissues).

Preferred, however, are nucleic acid molecules comprising, or alternatively consisting of, a nucleotide sequence at least 90%, 95%, 96%, 97%, 98% or 99% identical to for example, the nucleic acid sequence shown in FIGS. 1A–B (SEQ ID NO:2) or FIGS. 2A–B (SEQ ID NO:4), or to a nucleic acid sequence contained in the deposited cDNA, which do, in fact, encode a polypeptide having PSGR functional activity. By "a polypeptide having PSGR functional activity" is intended polypeptides exhibiting activity similar, but not necessarily identical, to an activity of the PSGR of the invention, as measured in a particular biological assay.

Of course, due to the degeneracy of the genetic code, one of ordinary skill in the art will immediately recognize that a large number of the nucleic acid molecules having a sequence at least 90%, 95%, 96%, 97%, 98%, or 99% identical to, for example, a nucleic acid sequence contained in the deposited cDNA or the nucleic acid sequence shown in FIGS. 1A–B (SEQ ID NO:2) or FIGS. 2A–B (SEQ ID NO:4), will encode a polypeptide "having PSGR functional activity." Similarly, a large number of the nucleic acid molecules having a sequence at least 90%, 95%, 96%, 97%, 98%, or 99% identical to, for example, a nucleic acid sequence centered in the deposited cDNA or the nucleic acid sequence shown in FIGS. 1A–B (SEQ ID NO: 1) or FIGS. 2A–B (SEQ ID NO:3) will encode a polypeptide "having PSGR functional activity." In fact, since degenerate variants of these nucleotide sequences all encode the same polypeptide, this will be clear to the skilled artisan even without performing a biological assay. It will be further recognized in the art that, for such nucleic acid molecules that are not degenerate variants, a reasonable number will also encode a polypeptide having PSGR functional activity. This is because the skilled artisan is fully aware of amino acid substitutions that are either less likely or not likely to significantly effect protein function (e.g., replacing one aliphatic amino acid with a second aliphatic amino acid), as further described below.

Polynucleotide Assays

This invention is also related to the use of PSGR polynucleotides to detect complementary polynucleotides such as, for example, as a diagnostic reagent. Detection of a normal and mutated form of PSGR associated with a dysfunction will provide a diagnostic tool that can add or define a diagnosis of a disease or susceptibility to a disease which results from under-expression over-expression or altered expression of PSGR (or a soluble form thereof), such as, for example, tumors or autoimmune disease.

In specific embodiments, PSGR polynucleotides of the invention are used to detect complementary polynucleotides as a diagnostic reagent for the detection of prostate cancer.

Individuals carrying mutations in the PSGR gene may be detected at the DNA level by a variety of techniques. Nucleic acids for diagnosis may be obtained from a biological sample from a patient (e.g., a patient's cells, such as from urine, semen, blood, saliva, tissue biopsy and autopsy material). The genomic DNA may be used directly for detection or may be amplified enzymatically by using PCR prior to analysis. (Saiki et al., Nature 324:163–166 (1986)). RNA or cDNA may also be used in the same ways. As an example, PCR primers complementary to the nucleic acid encoding PSGR can be used to identify and analyze PSGR expression and mutations. For example, deletions and insertions can be detected by a change in size of the amplified product in comparison to the normal genotype. Point mutations can be identified by hybridizing amplified DNA to radiolabeled PSGR RNA or alternatively, radiolabeled PSGR antisense DNA sequences. Perfectly matched sequences can routinely be distinguished from mismatched duplexes by techniques known in the art, such as, for example, RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis using techniques known in the art. DNA fragments of different sequences may be distinguished on denaturing formamide gradient gels in which the mobilities of different DNA fragments are retarded in the gel at different positions according to their specific melting or partial melting temperatures (see, e.g., Myers et al., Science 230:1242 (1985)).

Sequence changes at specific locations also may be revealed by nuclease protection assays, such as RNase and S1 protection or the chemical cleavage method (e.g., Cotton et al., Proc. Natl. Acad. Sci. USA 85: 4397–4401 (1985)).

Thus, the detection of a specific DNA sequence may be achieved by methods which include, but are not limited to, hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Recombinant and Synthetic Production of PSGR

The present invention also relates to vectors which include the isolated DNA molecules of the present invention, host cells which are genetically engineered with the recombinant vectors and/or nucleic acids of the invention, and the production of PSGR polypeptides or fragments thereof by recombinant and synthetic techniques.

Host cells can be genetically engineered to incorporate nucleic acid molecules and express polypeptides of the present invention. The polynucleotides may be introduced alone or with other polynucleotides. Such other polynucleotides may be introduced independently, co-introduced or introduced joined to the polynucleotides of the invention.

In accordance with the present invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells (e.g., *Saccharomyces cerevisiae* or *Pichia pastoris* (ATCC Accession No. 201178)); insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlbad, Calif.). Other suitable vectors will be readily apparent to the skilled artisan.

The present invention also relates to host cells containing the above-described vector constructs described herein, and additionally encompasses host cells containing nucleotide sequences of the invention that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., PSGR coding sequence), and/or to include genetic material (e.g., heterologous polynucleotide sequences) that is operably associated with PSGR polynucleotides of the invention, and which activates, alters, and/or amplifies endogenous PSGR polynucleotides. For example, techniques known in the art may be used to operably associate heterologous control regions (e.g., promoter and/or enhancer) and endogenous PSGR polynucleotide sequences via homologous recombination (see, e.g., U.S. Pat. No. 5,641,670, issued Jun. 24, 1997; International Publication Number WO 96/29411; International Publication Number WO 94/12650; Koller et al., *Proc. Natl. Acad. Sci. USA* 86:8932–8935 (1989); and Zijlstra et al., *Nature* 342:435–438 (1989), the disclosures of each of which are incorporated by reference in their entireties).

The PSGR polypeptide may be expressed in a modified form, such as a fusion protein (comprising the polypeptide joined via a peptide bond to a heterologous protein sequence (of a different protein)), and may include not only secretion signals but also additional heterologous functional regions. Alternatively, such a fusion protein can be made by protein synthetic techniques, e.g., by use of a peptide synthesizer. Thus, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. For example, in one embodiment, polynucleotides encoding PSGR polypeptides of the invention may be fused to the pelB pectate lyase signal sequence to increase the efficiency to expression and purification of such polypeptides in Gram-negative bacteria. See, U.S. Pat. Nos. 5,576,195 and 5,846,818, the contents of which are herein incorporated by reference in their entireties.

A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses, it would be desirable to be able to delete the Fc part after the fusion protein has been expressed, detected and purified in the advantageous manner described. This is the case when the Fc portion proves to be a hindrance to use in therapy and diagnosis, for example, when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, D. Bennett et al., *Journal of Molecular Recognition* 8:52–58 (1995) and K. Johanson et al., *The Journal of Biological Chemistry* 270:16:9459–9471 (1995).

Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

In one embodiment, the yeast *Pichia pastoris* is used to express PSGR in a eukaryotic system. *Pichia pastoris* is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., *Mol. Cell. Biol.* 5:1111–21 (1985); Koutz, P. J, et al., *Yeast* 5:167–77 (1989); Tschopp, J. F., et al., *Nucl. Acids Res.* 15:3859–76 (1987). Thus, a heterologous coding sequence, such as, for example, a PSGR polynucleotide of the present invention, under the transcriptional regulation of all or part of the AOX1 regulatory sequence may be expressed at exceptionally high levels in Pichia yeast grown in the presence of methanol.

In one example, the plasmid vector pPIC9K is used to express DNA encoding a PSGR polypeptide of the invention, as set forth herein, in a Pichea yeast system essentially as described in "Pichia Protocols: Methods in Molecular Biology," D. R. Higgins and J. Cregg, eds. The Humana Press, Totowa, N.J., 1998. This expression vector is used to express and secrete a PSGR protein of the invention by virtue of the strong AOX1 promoter linked to the yeast alpha factor prepro peptide signal sequence (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a PSGR polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., PSGR coding sequence), and/or to include genetic material (e.g., heterologous polynucleotide sequences) that is operably associated with PSGR polynucleotides of the invention, and which activates, alters, and/or amplifies endogenous PSGR polynucleotides. For example, techniques known in the art may be used to operably associate heterologous control regions (e.g., promoter and/or enhancer) and endogenous PSGR polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, proteins of the invention can be chemically synthesized using techniques known in the art (e.g., see Creighton, Proteins: Structures and Molecular Principles, W. H. Freeman & Co., N.Y. (1983), and Hunkapiller, et al., *Nature* 310:105–111 (1984)). For example, a polypeptide corresponding to a fragment of the PSGR polypeptides of the invention can be synthesized by use of a peptide synthesizer. Furthermore, if desired, nonclassical amino acids or chemical amino acid analogs can be introduced as a substitution or addition into the PSGR polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention additionally, encompasses PSGR polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of PSGR which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59–72 (1996); Vorobjev et al., *Nucleosides Nucleotides* 18:2745–2750 (1999); and Caliceti et al., *Bioconjug. Chem.* 10:638–646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249–304 (1992); Francis et al., *Intern. J. of Hematol.* 68:1–18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

As mentioned the PSGR proteins of the invention may be modified by either natural processes, such as posttranslational processing, or by chemical modification techniques which are well known in the art. It will be appreciated that the same type of modification may be present in the same or varying degrees at several sites in a given PSGR polypeptide. PSGR polypeptides may be branched, for example, as a result of ubiquitination, and they may be cyclic, with or without branching. Cyclic, branched, and branched cyclic PSGR polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., *Meth Enzymol* 182:626–646 (1990); Rattan et al., *Ann NY Acad Sci* 663:48–62 (1992)).

The PSGR polypeptides of the invention can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and/or purification.

PSGR polynucleotides and polypeptides may be used in accordance with the present invention for a variety of applications, particularly those that make use of the chemical and biological properties of PSGR. Among these are applications in the detection of prostate cancer, treatment of tumors, resistance to parasites, bacteria and viruses, to inhibit proliferation of B cells, to induce proliferation of T-cells, endothelial cells and certain hematopoietic cells, to treat restenosis, graft vs. host disease, to regulate anti-viral responses and to prevent certain autoimmune diseases after stimulation of PSGR by an agonist. Additional applications relate to diagnosis and to treatment of disorders of cells, tissues and organisms. These aspects of the invention are discussed further below.

The PSGR proteins (polypeptides) of the invention may be in monomers or multimers (i.e., dimers, trimers, tetramers, and higher multimers). Accordingly, the present invention relates to monomers and multimers of the PSGR proteins (polypeptides) of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only PSGR proteins of the invention (including PSGR fragments, variants, and fusion proteins, as described herein). These homomers may contain PSGR proteins having identical or different polypeptide sequences. In a specific embodiment, a homomer of the invention is a multimer containing only PSGR proteins having an identical polypeptide sequence. In another specific embodiment, a homomer of the invention is a multimer containing PSGR proteins having different polypeptide sequences (e.g., containing PSGR proteins having identical or different polypetide sequences.. In specific embodiments, the multimer of the invention is a homodimer (e.g., containing PSGR proteins having identical or different polypeptide sequences) or a homotrimer (e.g., containing PSGR proteins having identical or different polypeptide sequences). In additional embodiments, the homomeric multimer of the invention is at least a homodimer, at least a homotrimer, or at least a homotetramer.

As used herein, the term heteromer refers to a multimer containing heterologous proteins (i.e., proteins containing only polypeptide sequences that do not correspond to a polypeptide sequences encoded by the PSGR gene) in addition to the PSGR proteins of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the PSGR proteins of the invention. Such covalent associations may involve one or more amino acid residues contained in the polypeptide sequence of the protein (e.g., the polypeptide sequence shown in FIGS. 1A–B (SEQ ID NO:2) or FIGS. 2A–B (SEQ ID NO:4), or a polypeptide encoded by the deposited cDNA clone). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a PSGR fusion protein. In one example, covalent associations are between the heterologous sequence contained in a fusion protein of the invention (see, e.g., U.S. Pat. No. 5,478,925). In a specific example, the covalent associations are between the heterologous sequence contained in a PSGR-Fc fusion protein of the invention (as described herein). In another specific example, covalent associations of fusion proteins of the invention are between heterologous polypeptide sequences from another PSGR family ligand/receptor member that is capable of forming covalently associated multimers, such as for example, oseteoprotegerin (see, e.g., International Publication No. WO 98/49305, the contents of which are herein incorporated by reference in its entirety). In another embodiment, two or more PSGR polypeptides of the invention are joined through synthetic linkers (e.g., peptide, carbohydrate or soluble polymer linkers). Examples include those peptide linkers described in U.S. Pat. No. 5,073,627 (hereby incorporated by reference). Proteins comprising multiple PSGR polypeptides separated by peptide linkers may be produced using conventional recombinant DNA technology.

Another method for preparing multimer PSGR polypeptides of the invention involves use of PSGR polypeptides fused to a leucine zipper or isoleucine polypeptide sequence. Leucine zipper domains and isoleucine zipper domains are polypeptides that promote multimerization of the proteins in which they are found. Leucine zippers were originally identified in several DNA-binding proteins (Landschulz et al., *Science* 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric PSGR proteins are those described in PCT application WO 94/10308, hereby incorporated by reference. Recombinant fusion proteins comprising a soluble PSGR polypeptide fused to a peptide that dimerizes or trimerizes in solution are expressed in suitable host cells, and the resulting soluble multimeric PSGR is recovered from the culture supernatant using techniques known in the art.

Certain members of the TNF family of proteins are believed to exist in trimeric form (Beutler and Huffel, *Science* 264:667, 1994; Banner et al., *Cell* 73:431, 1993).

Thus, trimeric PSGR may offer the advantage of enhanced biological activity. Preferred leucine zipper moieties are those that preferentially form trimers. One example is a leucine zipper derived from lung surfactant protein D (SPD), as described in Hoppe et al. (*FEBS Letters* 344:191, (1994)) and in U.S. Pat. application Ser. No. 08/446,922, hereby incorporated by reference. Other peptides derived from naturally occurring trimeric proteins may be employed in preparing trimeric PSGR.

In another example, proteins of the invention are associated by interactions between Flag® polypeptide sequence contained in Flag®-PSGR fusion proteins of the invention. In a further embodiment, associated proteins of the invention are associated by interactions between heterologous polypeptide sequence contained in Flag®-PSGR fusion proteins of the invention and anti-Flag® antibody.

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

Transgenics and "Knock-outs"

The PSGR proteins of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., nucleic acids of the invention) into animals to produce the founder lines of transgenic animals. Such techniques include, but are not limited to, pronuclear microinjection (Paterson et al., *Appl. Microbiol. Biotechnol.* 40:691–698 (1994); Carver et al., *Biotechnology* (NY) 11:1263–1270 (1993); Wright et al., *Biotechnology* (NY) 9:830–834 (1991); and Hoppe et al., U.S. Pat. No. 4,873,191 (1989)); retrovirus mediated gene transfer into germ lines (Van der Putten et al., *Proc. Natl. Acad. Sci., USA* 82:6148–6152 (1985)), blastocysts or embryos; gene targeting in embryonic stem cells (Thompson et al., *Cell* 56:313–321 (1989)); electroporation of cells or embryos (Lo, *Mol Cell. Biol.* 3:1803–1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717–723 (1989); etc. For a review of such techniques, see Gordon, "Transgenic Animals," *Intl. Rev. Cytol.* 115:171–229 (1989), which is incorporated by reference herein in its entirety. Further, the contents of each of the documents recited in this paragraph is herein incorporated by reference in its entirety. Gordon, "Transgenic Animals," Intl. Rev. Cytol. 115:171–229 (1989), which is incorporated by reference herein in its entirety. See also, U.S. Pat. No. 5,464,764 (Capecchi, et al., Positive-Negative Selection Methods and Vectors); U.S. Pat. No. 5,631,153 (Capecchi, et al., Cells and Non-Human Organisms Containing Predetermined Genomic Modifications and Positive-Negative Selection Methods and Vectors for Making Same); U.S. Pat. No. 4,736,866 (Leder, et al., Transgenic Non-Human Animals); and U.S. Pat. No. 4,873,191 (Wagner, et al., Genetic Transformation of Zygotes); each of which is hereby incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., *Nature* 380:64–66 (1996); Wilmut et al., *Nature* 385:810–813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (*Proc. Natl. Acad. Sci. USA* 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (*Science* 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of PSGR polypeptides, studying conditions and/or disorders associated with aberrant PSGR expression, and in screening for compounds effective in ameliorating such conditions and/or disorders.

In further embodiments of the invention, cells that are genetically engineered to express the proteins of the invention, or alternatively, that are genetically engineered not to express the proteins of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

PSGR Polypeptides and Fragments

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the PSGR polypeptide can be substantially purified by the one-step method described in Smith and Johnson, *Gene* 67:31–40 (1988).

Accordingly, in one embodiment, the invention provides an isolated PSGR polypeptide having the amino acid sequence encoded by encoded by the cDNA contained in ATCC Deposit No. 97131, or the amino acid sequence in FIGS. 1A–B (SEQ ID NO:2), or the amino acid sequence in FIGS. 2A–B (SEQ ID NO:4), or a polypeptide comprising a portion of the above polypeptides, such as for example, the PSGR extracellular loop I comprising, or alternatively consisting of, amino acids 77 to 98 of FIGS. 1A–B (SEQ ID NO:2) or FIGS. 2A–B (SEQ ID NO:4); the PSGR extracellular loop II comprising, or alternatively consisting of, amino acids 163 to 197 of FIGS. 1A–B (SEQ ID NO:2) or FIGS. 2A–B (SEQ ID NO:4); the PSGR extracellular loop III comprising, or alternatively consisting of, amino acids 262 to 272 of FIGS. 1A–B (SEQ ID NO:2) or FIGS. 2A–B (SEQ ID NO:4); the PSGR intracellular loop I comprising, or alternatively consisting of, amino acids 43 to 55 of FIGS. 1A–B (SEQ ID NO:2) or FIGS. 2A–B (SEQ ID NO:4); the PSGR intracellular loop II comprising, or alternatively consisting of, amino acids 120 to 141 of FIGS. 1A–B (SEQ ID NO:2) or FIGS. 2A–B (SEQ ID NO:4); and/or the PSGR intracellular loop III comprising, or alternatively consisting of, amino acids 219 to 240 of FIGS. 1A–B (SEQ ID NO:2) or FIGS. 2A–B (SEQ ID NO:4).

Polypeptide fragments of the present invention include polypeptides comprising or alternatively, consisting of: an amino acid sequence contained in FIGS. 1A–B (SEQ ID NO:2); an amino acid sequence contained in FIGS. 2A–B (SEQ ID NO:4); an amino acid sequence encoded by the cDNA contained in ATCC Deposit No. 97131; an amino acid sequence encoded by a nucleic acid containing a polynucleotide sequence which hybridizes (e.g., under stringent hybridization conditions) to the nucleotide sequence contained in the deposited clone; or an amino acid sequence encoded by a nucleic acid containing a polynucleotide sequence which hybridizes to the complementary strand of the nucleotide sequence shown in FIGS. 1A–B (SEQ ID NO: 1) or FIGS. 2A–B (SEQ ID NO:3). Polynucleotides encoding these polypeptides are also encompassed by the invention.

Protein fragments may be "free-standing," or comprised within a larger polypeptide of which the fragment forms a part or region, most preferably as a single continuous region. Representative examples of polypeptide fragments of the invention, include, for example, fragments that comprise or alternatively, consist of from about amino acid residues: 1 to 21, 22 to 42, 43 to 55, 56 to 76, 77 to 98, 99 to 119, 120 to 141, 142 to 162, 163 to 197, 198 to 218, 219 to 240, 241 to 261, 262 to 272, 273 to 293, and/or 294 to 320 of SEQ ID NO:2. Moreover, polypeptide fragments can be at least 10, 20, 30, 40, 50, 60, 70, 80, 90, 100, 110, 120, 130, 140, 150, 175, 200, 250, 300, 350, 400 or 500 amino acids in length. Polynucleotides encoding these polypeptides are also encompassed by the invention. In this context "about" includes the particularly recited ranges, larger or smaller by several (5, 4, 3, 2, or 1) amino acids, at either extreme or at both extremes. Polynucleotides encoding these polypeptides are also encompassed by the invention.

In additional embodiments, the polypeptide fragments of the invention comprise, or alternatively consist of, one or more PSGR domains. Preferred polypeptide fragments of the present invention include a member selected from the group: (a) a polypeptide comprising or alternatively, consisting of, the PSGR transmembrane domain I (predicted to constitute amino acid residues from about 22 to about 42 in FIGS. 1A–B (SEQ ID NO:2) or FIGS. 2A–B (SEQ ID NO:4)); (b) a polypeptide comprising, or alternatively consisting of, the PSGR transmembrane domain II (predicted to constitute amino acid residues from about 56 to about 76 in FIGS. 1A–B (SEQ ID NO:2) or FIGS. 2A–B (SEQ ID NO:4)); (c) a polypeptide comprising, or alternatively consisting of the PSGR transmembrane domain III (predicted to constitute amino acid residues from about 99 to about 119 in FIGS. 1A–B (SEQ ID NO:2) or FIGS. 2A–B (SEQ ID NO:4)); (d) a polypeptide comprising, or alternatively consisting of, the PSGR transmembrane domain IV (predicted to constitute amino acid residues from about 142 to about 162 in FIGS. 1A–B (SEQ ID NO:2) or FIGS. 2A–B (SEQ ID NO:4)); (e) a polypeptide comprising, or alternatively consisting of, the PSGR transmembrane domain V (predicted to constitute amino acid residues from about 198 to about 218 in FIGS. 1A–B (SEQ ID NO:2) or FIGS. 2A–B (SEQ ID NO:4)); (f) a polypeptide comprising, or alternatively consisting of, the PSGR transmembrane domain VI (predicted to constitute amino acid residues from about 241 to about 261 in FIGS. 1A–B (SEQ ID NO:2) or FIGS. 2A–B (SEQ ID NO:4)); (g) a polypeptide comprising, or alternatively consisting of, a polypeptide comprising, or alternatively consisting of, the PSGR transmembrane domain VII (predicted to constitute amino acid residues from about 273 to about 293 in FIGS. 1A–B (SEQ ID NO:2) or FIGS. 2A–B (SEQ ID NO:4)); (h) a polypeptide comprising, or alternatively consisting of, the PSGR extracellular loop I (predicted to constitute amino acid residues from about 77 to about 98 in FIGS. 1A–B (SEQ ID NO:2) or FIGS. 2A–B (SEQ ID NO:4)); (i) a polypeptide comprising, or alternatively consisting of, the PSGR extracellular loop II (predicted to constitute amino acid residues from about 163 to about 197 in FIGS. 1A–B (SEQ ID NO:2) or FIGS. 2A–B (SEQ ID NO:4)); (j) a polypeptide comprising, or alternatively consisting of, the PSGR extracellular loop III (predicted to constitute amino acid residues from about 262 to about 272 in FIGS. 1A–B (SEQ ID NO:2) or FIGS. 2A–B (SEQ ID NO:4)); (k) a polypeptide comprising, or alternatively consisting of, the PSGR intracellular loop I (predicted to constitute amino acid residues from about 43 to about 55 in FIGS. 1A–B (SEQ ID NO:2) or FIGS. 2A–B (SEQ ID NO:4)); (l) a polypeptide comprising, or alternatively consisting of, the PSGR intracellular loop II (predicted to constitute amino acid residues from about 120 to about 141 in FIGS. 1A–B (SEQ ID NO:2) or FIGS. 2A–B (SEQ ID NO:4)); (m) a polypeptide comprising, or alternatively consisting of, the PSGR intracellular loop III (predicted to constitute amino acid residues from about 219 to about 240 in FIGS. 1A–B (SEQ ID NO:2) or FIGS. 2A–B (SEQ ID NO:4)); or (n) any combination of polypeptides (a)–(m). Polynucleotides encoding these polypeptides are also encompassed by the invention.

Among the especially preferred fragments of the invention are fragments characterized by structural or functional attributes of PSGR. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, alpha amphipathic regions, beta amphipathic regions, surface forming regions, and high antigenic index regions (i.e., containing four or more contiguous amino acids having an antigenic index of greater than or equal to 1, as identified using the default parameters of the Jameson-Wolf program) of complete (i.e., full-length) PSGR (FIGS. 1A–B (SEQ ID NO:2)). Certain preferred regions are those set out in FIG. 4 and include, but are not limited to, regions of the aforementioned types identified by analysis of the amino acid sequence depicted in FIGS. 1A–B (SEQ ID NO:2), such preferred regions include; Garnier-Robson predicted alpha-regions, beta-regions, turn-regions, and coil-regions; Chou-Fasman predicted alpha-regions, beta-regions, and turn-regions; Kyte-Doolittle predicted hydrophilic; Eisenberg alpha and beta amphipathic regions; Karplus-Schulz predicted flexible regions; Jameson-Wolf high antigenic index regions; and Emini surface-forming regions, as predicted using the default parameters of these computer programs. Polynucleotides encoding these polypeptides are also encompassed by the invention.

As mentioned above, even if deletion of one or more amino acids from the N-terminus of a protein results in modification of loss of one or more biological functions of the protein, other functional activities (e.g., biological activities, ability to multimerize, ability to bind PSGR ligand or couple to G protein) may still be retained. For example, the ability of shortened PSGR muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete full-length polypeptide retains such immunologic activities can readily be determined by routine methods described herein and otherwise known in the art. It is not unlikely that an PSGR mutein with a large number of deleted N-terminal amino acid residues may retain some biological or immunogenic activities. In fact, peptides composed of as few as six PSGR amino acid residues may often evoke an immune response.

Accordingly, the present invention further provides polypeptides having one or more residues deleted from the amino terminus of the PSGR amino acid sequence shown in FIGS. 1A–B, up to the glutarnine residue at position number 315 and polynucleotides encoding such polypeptides. In particular, the present invention provides polypeptides comprising the amino acid sequence of residues $n^1$-320 of FIGS. 1A–B, where $n^1$ is an integer from 2 to 315 corresponding to the position of the amino acid residue in FIGS. 1A–B (SEQ ID NO:2).

More in particular, the invention provides polynucleotides encoding polypeptides comprising, or alternatively consisting of, the amino acid sequence of residues: S-2 to K-320; S-3 to K-320; C-4 to K-320; N-5 to K-320; F-6 to K-320; T-7 to K-320; H-8 to K-320; A-9 to K-320; T-10 to K-320; C-11 to K-320; V-12 to K-320; L-13 to K-320; I-14 to K-320; G-13 to K-320; I-16 to K-320; P-17 to K-320; G-18 to K-320; L-19 to K-320; E-20 to K-320; K-21 to K-320; A-22 to K-320; H-23 to K-320; F-24 to K-320; W-25 to K-320; V-26 to K-320; G-27 to K-320; F-28 to K-320; P-29 to K-320; L-30 to K-320; L-31 to K-320; S-32 to K-320; M-33 to K-320; Y-34 to K-320; V-35 to K-320; V-36 to K-320; A-37 to K-320; M-38 to K-320; C-39 to K-320; G-40 to K-320; N-41 to K-320; C-42 to K-320; I-43 to K-320; V-44 to K-320; V-45 to K-320; F-46 to K-320; I-47 to K-320; V-48 to K-320; R-49 to K-320; T-50 to K-320; E-51 to K-320; R-52 to K-320; S-53 to K-320; L-54 to K-320; H-55 to K-320; A-56 to K-320; P-57 to K-320; M-58 to K-320; Y-59 to K-320; L-60 to K-320; F-61 to K-320; L-62 to K-320; C-63 to K-320; M-64 to K-320; L-65 to K-320; A-66 to K-320; A-67 to K-320; I-68 to K-320; D-69 to K-320; L-70 to K-320; A-71 to K-320; L-72 to K-320; S-73 to K-320; T-74 to K-320; S-75 to K-320; T-76 to K-320; M-77 to K-320; P-78 to K-320; K-79 to K-320; I-80 to K-320; L-81 to K-320; A-82 to K-320; L-83 to K-320; F-84 to K-320; W-85 to K-320; F-86 to K-320; D-87 to K-320; S-88 to K-320; R-89 to K-320; E-90 to K-320; I-91 to K-320; S-92 to K-320; I-93 to K-320; E-94 to K-320; A-95 to K-320; C-96 to K-320; L-97 to K-320; T-98 to K-320; Q-99 to K-320; M-100 to K-320; F-101 to K-320; F-102 to K-320; I-103 to K-320; H-104 to K-320; A-105 to K-320; L-106 to K-320; S-107 to K-320; A-108 to K-320; I-109 to K-320; E-110 to K-320; S-111 to K-320; T-112 to K-320; I-113 to K-320; L-114 to K-320; L-115 to K-320; A-116 to K-320; M-117 to K-320; A-118 to K-320; F-119 to K-320; D-120 to K-320; R-121 to K-320; Y-122 to K-320; V-123 to K-320; A-124 to K-320; I-125 to K-320; C-126 to K-320; H-127 to K-320; P-128 to K-320; L-129 to K-320; R-130 to K-320; H-131 to K-320; A-132 to K-320; A-133 to K-320; V-134 to K-320; L-135 to K-320; N-136 to K-320; N-137 to K-320; T-138 to K-320; V-139 to K-320; T-140 to K-320; A-141 to K-320; Q-142 to K-320; I-143 to K-320; G-144 to K-320; I-145 to K-320; V-146 to K-320; A-147 to K-320; V-148 to K-320; V-149 to K-320; R-150 to K-320; G-151 to K-320; S-152 to K-320; L-153 to K-320; F-154 to K-320; F-155 to K-320; F-156 to K-320; P-157 to K-320; L-158 to K-320; P-159 to K-320; L-160 to K-320; L-161 to K-320; I-162 to K-320; K-163 to K-320; R-164 to K-320; L-165 to K-320; A-166 to K-320; F-167 to K-320; C-168 to K-320; H-169 to K-320; S-170 to K-320; N-171 to K-320; V-172 to K-320; L-173 to K-320; S-174 to K-320; H-175 to K-320; S-176 to K-320; Y-177 to K-320; C-178 to K-320; V-179 to K-320;

H-180 to K-320; Q-181 to K-320; D-182 to K-320; V-183 to K-320; M-184 to K-320; K-185 to K-320; L-186 to K-320; A-187 to K-320; Y-188 to K-320; A-189 to K-320; D-190 to K-320; T-191 to K-320; L-192 to K-320; P-193 to K-320; N-194 to K-320; V-195 to K-320; V-196 to K-320; Y-197 to K-320; G-198 to K-320; L-199 to K-320; T-200 to K-320; A-201 to K-320; I-202 to K-320; L-203 to K-320; L-204 to K-320; V-205 to K-320; M-206 to K-320; G-207 to K-320; V-208 to K-320; D-209 to K-320; V-210 to K-320; M-211 to K-320; F-212 to K-320; I-213 to K-320; S-214 to K-320; L-215 to K-320; S-216 to K-320; Y-217 to K-320; F-218 to K-320; L-219 to K-320; I-220 to K-320; I-221 to K-320; R-222 to K-320; T-223 to K-320; V-224 to K-320; L-225 to K-320; Q-226 to K-320; L-227 to K-320; P-228 to K-320; S-229 to K-320; K-230 to K-320; S-231 to K-320; E-232 to K-320; R-233 to K-320; A-234 to K-320; K-235 to K-320; A-236 to K-320; F-237 to K-320; G-238 to K-320; T-239 to K-320; C-240 to K-320; V-241 to K-320; S-242 to K-320; H-243 to K-320; I-244 to K-320; G-245 to K-320; V-246 to K-320; V-247 to K-320; L-248 to K-320; A-249 to K-320; F-250 to K-320; Y-251 to K-320; V-252 to K-320; P-253 to K-320; L-254 to K-320; I-255 to K-320; G-256 to K-320; L-257 to K-320; S-258 to K-320; V-259 to K-320; V-260 to K-320; H-261 to K-320; R-262 to K-320; F-263 to K-320; G-264 to K-320; N-265 to K-320; S-266 to K-320; L-267 to K-320; H-268 to K-320; P-269 to K-320; I-270 to K-320; V-271 to K-320; R-272 to K-320; V-273 to K-320; V-274 to K-320; M-275 to K-320; G-276 to K-320; D-277 to K-320; I-278 to K-320; Y-279 to K-320; L-280 to K-320; L-281 to K-320; L-282 to K-320; P-283 to K-320; P-284 to K-320; V-285 to K-320; I-286 to K-320; N-287 to K-320; P-288 to K-320; I-289 to K-320; I-290 to K-320; Y-291 to K-320; G-292 to K-320; A-293 to K-320; K-294 to K-320; T-295 to K-320; K-296 to K-320; Q-297 to K-320; I-298 to K-320; R-299 to K-320; T-300 to K-320; R-301 to K-320; V-302 to K-320; L-302 to K-320; A-304 to K-320; M-305 to K-320; F-306 to K-320; K-307 to K-320; I-308 to K-320; S-309 to K-320; C-310 to K-320; D-311 to K-320; K-312 to K-320; D-313 to K-320; L-314 to K-320 and/or Q-315 to K-320 of the PSGR sequence shown in FIGS. 1A–B (SEQ ID NO:2). Polypeptides encoded by these polynucleotides are also encompassed by the invention.

Also as mentioned above, even if deletion of one or more amino acids from the C-terminus of a protein results in modification of loss of one or more biological functions of the protein, other functional activities (e.g., biological activities, ability to multimerize, ability to bind PSGR ligand may still be retained). For example the ability of the shortened PSGR mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a PSGR mutein with a large number of deleted C-terminal amino acid residues may retain some biological or immunogenic activities. In fact, peptides composed of as few as six PSGR amino acid residues may often evoke an immune response.

Accordingly, the present invention further provides polypeptides having one or more residues deleted from the carboxy terminus of the amino acid sequence of the PSGR polypeptide shown in FIGS. 1A–B, up to the phenylalanine residue at position number 6, and polynucleotides encoding such polypeptides. In particular, the present invention provides polypeptides comprising the amino acid sequence of residues 1-m$^1$ of FIGS. 1A–B, where m$^1$ is an integer from 6 to 319 corresponding to the position of the amino acid residue in FIGS. 1A–B (SEQ ID NO:2).

More in particular, the invention provides polynucleotides encoding polypeptides comprising, or alternatively consisting of, the amino acid sequence of residues: M-1 to G-319; M-1 to G-318; M-1 to V-317; M-1 to A-316; M-1 to Q-315; M-1 to L-314; M-1 to D-319; M-1 to K-312; M-1 to D-311; M-1 to C-310; M-1 to S-309; M-1 to I-308; M-1 to K-307; M-1 to F-306; M-1 to M-305; M-1 to A-304; M-1 to L-303; M-1 to V-302; M-1 to R301; M-1 to T-300; M-1 to R-299; M-1 to I-298; M-1 to Q-297; M-1 to K-296; M-1 to T-295; M-1 to K-294; M-1 to A-293; M-1 to G-292; M-1 to Y-291; M-1 to I-290; M-1 to I-289; M-1 to P-288; M-1 to N-287; M-1 to I-286; M-1 to V-285; M-1 to P-284; M-1 to P-283; M-1 to L-282; M-1 to L-281; M-1 to L-280; M-1 to Y-279; M-1 to I-278; M-1 to D-277; M-1 to G-276; M-1 to M-275; M-1 to V-274; M-1 to V-273; M-1 to R-272; M-1 to V-271; M-1 to I-270; M-1 to P-269; M-1 to H-268; M-1 to L-267; M-1 to S-266; M-1 to N-265; M-1 to G-264; M-1 to F-263; M-1 to R-262; M-1 to H-261; M-1 to V-260; M-1 to V-259; M-1 to S-258; M-1 to L-257; M-1 to G-256; M-1 to I-255; M-1 to L-254; M-1 to P-253; M-1 to V-252; M-1 to Y-251; M-1 to F-250; M-1 to A-249; M-1 to L-248; M-1 to V-247; M-1 to V-264; M-1 to G-245; M-1 to I-244; M-1 to H-243; M-1 to S-242; M-1 to V-241; M-1 to C-240; M-1 to T-239; M-1 to G-238; M-1 to F-237; M-1 to A-236; M-1 to K-235; M-1 to A-234; M-1 to R-233; M-1 to E-232; M-1 to S-231; M-1 to K-230; M-1 to S-229; M-1 to P-228; M-1 to L-227; M-1 to Q-226; M-1 to L-225; M-1 to V-224; M-1 to T-223; M-1 to R-222; M-1 to I-221; M-1 to I-220; M-1 to L-219; M-1 to F-218; M-1 to Y-217; M-1 to S-216; M-1 to L-215; M-1 to S-214; M-1 to I-213; M-1 to F-212; M-1 to M-211; M-1 to V-210; M-1 to D-209; M-1 to V-208; M-1 to G-207; M-1 to M-206; M-1 to V-205; M-1 to L-204; M-1 to L-203; M-1 to I-202; M-1 to A-201; M-1 to T-200; M-1 to L-199; M-1 to G-198; M-1 to Y-197; M-1 to V-196; M-1 to V-195; M-1 to N-194; M-1 to P-193; M-1 to L-192; M-1 to T-191; M-1 to D-190; M-1 to A-189; M-1 to Y-188; M-1 to A-187; M-1 to L-186; M-1 to K-185; M-1 to M-184; M-1 to V-183; M-1 to D-182; M-1 to Q-181; M-1 to H-180; M-1 to V-179; M-1 to C-178; M-1 to Y-177; M-1 to S-176; M-1 to H-175; M-1 to S-174; M-1 to L-173; M-1 to V-172; M-1 to N-171; M-1 to S-170; M-1 to H-169; M-1 to C-168; M-1 to F-167; M-1 to A-166; M-1 to L-165; M-1 to R-164; M-1 to K-163; M-1 to I-162; M-1 to L-161; M-1 to L-160; M-1 to P-159; M-1 to L-158; M-1 to P-157; M-1 to F-156; M-1 to F-155; M-1 to F-154; M-1 to L-153; M-1 to S-152; M-1 to G-151; M-1 to R-150; M-1 to V-149; M-1 to V-148; M-1 to A-147; M-1 to V-146; M-1 to I-145; M-1 to G-144; M-1 to I-143; M-1 to Q-142; M-1 to A-141; M-1 to T-140; M-1 to V-139; M-1 to T-138; M-1 to N-137; M-1 to N-136; M-1 to L-135; M-1 to V-134; M-1 to A-133; M-1 to A-132; M-1 to H-131; M-1 to R-130; M-1 to L-129; M-1 to P-128; M-1 to H-127; M-1 to C-126; M-1 to I-125; M-1 to A-124; M-1 to V-123; M-1 to Y-122; M-1 to R-112; M-1 to D-120; M-1 to F-119; M-1 to A-118; M-1 to M-117; M-1 to A-116; M-1 to L-115; M-1 to L-114; M-1 to I-113; M-1 to T-112; M-1 to S-111; M-1 to E-110; M-1 to I-109; M-1 to A-108; M-1 to S-107; M-1 to L-106; M-1 to A-105; M-1 to H-104; M-1 to I-103; M-1 to F-102; M-1 to F-101; M-1 to M-100; M-1 to Q-99; M-1 to T-98; M-1 to L-97; M-1 to C-96; M-1 to A-95; M-1 to E-94; M-1 to I-93; M-1 to S-92; M-1 to I-91; M-1 to E-90; M-1 to R-89; M-1 to S-88; M-1 to D-87; M-1 to F-86; M-1 to W-85; M-1 to F-84; M-1 to L-83; M-1 to A-82; M-1 to L-81; M-1 to I-80; M-1 to K-79; M-1 to P-78; M-1 to M-77;

M-1 to T-76; M-1 to S-75; M-1 to T-74; M-1 to S-73; M-1 to L-72; M-1 to A-71; M-1 to L-70; M-1 to D-69; M-1 to I-68; M-1 to A-67; M-1 to A-66; M-1 to L-65; M-1 to M-64; M-1 to C-63; M-1 to L-62; M-1 to F-61; M-1 to L-60; M-1 to Y-59; M-1 to M-58; M-1 to P-57; M-1 to A-56; M-1 to H-55; M-1 to L-54; M-1 to S-53; M-1 to R-52; M-1 to E-51; M-1 to T-50; M-1 to R-49; M-1 to V-48; M-1 to I-47; M-1 to F-46; M-1 to V-45; M-1 to V-44; M-1 to I-43; M-1 to C-42; M-1 to N-41; M-1 to G-40; M-1 to C-39; M-1 to M-38; M-1 to A-37; M-1 to V-36; M-1 to V-35; M-1 to Y-34; M-1 to M-33; M-1 to S-32; M-1 to L-31; M-1 to L-30; M-1 to P-29; M-1 to F-28; M-1 to G-27; M-1 to V-26; M-1 to W-25; M-1 to F-24; M-1 to H-23; M-1 to A-22; M-1 to K-21; M-1 to E-20; M-1 to L-19; M-1 to G-18; M-1 to P-17; M-1 to I-16; M-1 to G-15; M-1 to I-14; M-1 to L-13; M-1 to V-12; M-1 to C-11; M-1 to T-10; M-1 to A-9; M-1 to H-8; M-1 to T-7 and/or M-1 to F-6 of the PSGR sequence shown in FIGS. 1A–B (SEQ ID NO:2). Polypeptides encoded by these polynucleotides are also encompassed by the invention.

The invention also provides polypeptides having one or more amino acids deleted from both the amino and the carboxyl termini, which may be described generally as having residues $n^1$-$m^1$ of FIGS. 1A–B (i.e., SEQ ID NO:2), where $n^1$ and $m^1$ are integers as described above. Thus, any of the above listed N- or C-terminal deletions can be combined to produce a N- and C-terminal deleted PSGR polypeptide.

In addition, the invention provides the above described polypeptide deletions (e.g., $n^1$-320, 1-$m^1$, or $n^1$-$m^1$, where $n^1$ and $m^1$ are integers as described above) containing one, two or all three of the following substitutions: a F11 replaced with C; F39 replaced with C; and F93 replaced with I of the PSGR amino acid sequence shown in FIGS. 1A–B (SEQ ID NO:2). Polynucleotides encoding these polypeptides are also encompassed by the invention.

The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the PSGR polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98% or 99% identical to the amino acid sequence described above, and polynucleotides that encode such polypeptides.

Additional preferred polynucleotides encode polypeptides comprising, or alternatively consisting of, the amino acid sequence of residues: M-1 to G-15; S-2 to I-16; S-3 to P-17; C-4 to G-18; N-5 to L-19; F-6 to E-20; T-7 to K-21; H-8 to A-22; A-9 to H-23; T-10 to F-24; C-11 to W-25; V-12 to V-26; L-13 to G-27; I-14 to F-28; G-15 to P-29; I-16 to L-30; P-17 to L-31; G-18 to S-32; L-19 to M-33; E-20 to Y-34; K-21 to V-35; A-22 to V-36; H-23 to A-37; F-24 to M-38; W-25 to C-39; V-26 to G-40; G-27 to N-41; F-28 toC-42; P-29 to I-43; L-30 to V-44; L-31 to V-45; S-32 to F-46; M-33 to I-47; Y-34 to V-48; V-35 to R-49; V-36 to T-50; A-37 to E-51; M-38 to R-52; C-39 to S-53; G-40 to L-54; N-41 to H-55; C-42 to A-56; I-43 to P-57; V-44 to M-58; V-45 to Y-59; F-46 to L-60; I-47 to F-61; V-48 to L-62; R-49 to C-63; T-50 to M-64; E-51 to L-65; R-52 to A-66; S-53 to A-67; L-54 to I-68; H-55 to D-69; A-56 to L-70; P-57 to A-71; M-58 to L-72; Y-59 to S-73; L-60 to T-74; F-61 to S-75; L-62 to T-76; C-63 to M-77; M-64 to P-78; L-65 to K-79; A-66 to I-80; A-67 to L-81; I-68 to A-82; D-69 to L-83; L-70 to F-84; A-71 to W-85; L-72 to F-86; S-73 to D-87; T-74 to S-88; S-75 to R-89; T-76 to E-90; M-77 to I-91; P-78 to S-92; K-79 to I-93; I-80 to E-94; L-81 to A-95; A-82 to C-96; L-83 to L-97; F-84 to T-98; W-85 to Q-99; F-86 to M-100; D-87 to F-101; S-88 to F-102; R-89 to I-103; E-90 to H-104; I-91 to A-105; S-92 to L-106; I-93 to S-107; E-94 to A-108; A-95 to I-109; C-96 to E-110; L-97 to S-111; T-98 to T-112; Q-99 to I-113; M-100 to L-114; F-101 to L-115; F-102 to A-116; I-103 to M-117; H-104 to A-118; A-105 to F-119; L-106 to D-120; S-107 to R-121; A-108 to Y-122; I-109 to V-123; E-110 to A-124; S-111 to I-125; T-112 to C-126; I-113 to H-127; L-114 to P-128; L-115 to L-129; A-116 to R-130; M-117 to H-131; A-118 to A-132; F-119 to A-133; D-120 to V-134; R-121 to L-135; Y-122 to N-136; V-123 to N-137; A-124 to T-138; I-125 to V-139; C-126 to T-140; H-127 to A-141; P-128 to Q-142; L-129 to I-143; R-130 to G-144; H-131 to I-145; A-132 to V-146; A-133 to A-147; V-134 to V-148; L-135 to V-149; N-136 to R-150; N-137 to G-151; T-138 to S-152; V-139 to L-153; T-140 to F-154; A-141 to F-155; Q-142 to F-156; I-143 to P-157; G-144 to L-158; I-145 to P-159; V-146 to L-160; A-147 to L-161; V-148 to I-162; V-149 to K-163; R-150 to R-164; G-151 to L-165; S-152 to A-166; L-153 to F-167; F-154 to C-168; F-155 to H-169; F-156 to S-170; P-157 to N-171; L-158 to V-172; P-159 to L-173; L-160 to S-174; L-161 to H-175; I-162 to S-176; K-163 to Y-177; R-164 to C-178; L-165 to V-179; A-166 to H-180; F-167 to Q-181; C-168 to D-182; H-169 to V-183; S-170 to M-184; N-171 to K-185; V-172 to L-186; L-173 to A-187; S-174 to Y-188; H-175 to A-189; S-176 to D-190; Y-177 to T-191; C-178 to L-192; V-179 to P-193; H-180 to N-194; Q-181 to V-195; D-182 to V-196; V-183 to Y-197; M-184 to G-198; K-185 to L-199; L-186 to T-200; A-187 to A-201; Y-188 to I-202; A-189 to L-203; D-190 to L-204; T-191 to V-205; L-192 to M-206; P-193 to G-207; N-194 to V-208; V-195 to D-209; V-196 to V-210; Y-197 to M-211; G-198 to F-212; L-199 to I-213; T-200 to S-214; A-201 to L-215; I-202 to S-216; L-203 to Y-217; L-204 to F-218; V-205 to L-219; M-206 to I-220; G-207 to I-221; V-208 to R-222; D-209 to T-223; V-210 to V-224; M-211 to L-225; F-212 to Q-226; I-213 to L-227; S-214 to P-228; L-215 to S-229; S-216 to K-230; Y-217 to S-231; F-218 to E-232; L-219 to R-233; I-220 to A-234; I-221 to K-235; R-222 to A-236; T-223 to F-237; V-224 to G-238; L-225 to T-239; Q-226 to C-240; L-227 to V-241; P-228 to S-242; S-229 to H-243; K-230 to I-244; S-231 to G-245; E-232 to V-246; R-233 to V-247; A-234 to L-248; K-235 to A-249; A-236 to F-250; F-237 to Y-251; G-238 to V-252; T-239 to P-253; C-240 to L-254; V-241 to I-255; S-242 to G-256; H-243 to L-257; I-244 to S-258; G-245 to V-259; V-246 to V-260; V-247 to H-261; L-248 to R-262; A-249 to F-263; F-250 to G-264; Y-251 to N-265; V-252 to S-266; P-253 to L-267; L-254 to H-268; I-255 to P-269; G-256 to I-270; L-257 to V-271; S-258 to R-272; V-259 to V-273; V-260 to V-274; H-261 to M-275; R-262 to G-276; F-263 to D-277; G-264 to I-278; N-265 to Y-279; S-266 to L-280; L-267 to L-281; H-268 to L-282; P-269 to P-283; I-270 to P-284; V-271 to V-285; R-272 to I-286; V-273 to N-287; V-274 to P-288; M-275 to I-289; G-276 to I-290; D-277 to Y-291; I-278 to G-292; Y-279 to A-293; L-280 to K-294; L-281 to T-295; L-282 to K-296; P-283 to Q-297; P-284 to I-298; V-285 to R-299; I-286 to T-300; N-287 to R-301; P-288 to V-302; I-289 to L-303; I-290 to A-304; Y-291 to M-305; G-292 to F-306; A-293 to K-307; K-294 to I-308; T-295 to S-309; K-296 to C-310; Q-297 to D-311; I-298 to K-312; R-299 to D-313;

T-300 to L-314; R-301 to Q-315; V-302 to A-316; L-303 to V-317; A-304 to G-318; M-305 to G-319; and F-306 to K-320 of SEQ ID NO:2. These polypeptide fragments may retain the biological activity of PSGR polypeptides of the invention and/or may be useful to generate or screen for antibodies, as described further below. Polynucleotides encoding these polypeptide fragments are also encompassed by the invention.

In addition, the invention provides the above described polypeptide fragments containing one, two or all three of the following substitutions: a F11 replaced with C; F39 replaced with C; and F93 replaced with I of the PSGR amino acid sequence shown in FIGS. 1A–B (SEQ ID NO:2). Polynucleotides encoding these polypeptides are also encompassed by the invention.

The present application is also directed to nucleic acid molecules comprising, or alternatively, consisting of, a polynucleotide sequence at least 90%, 92%, 95%, 96%, 97%, 98%, or 99% identical to the polynucleotide sequence encoding the PSGR polypeptides described above. The present invention also encompasses the above polynucleotide sequences fused to a heterologous polynucleotide sequence. Additionally, the present application is also directed to proteins containing polypeptides at least 90%, 92%, 93%, 94%, 95%, 96%, 97%, 98% or 99% identical to the PSGR polypeptide fragments set forth above. Polypeptides encoded by these polynucleotides are also encompassed by the invention.

It will be recognized in the art that some amino acid sequences of PSGR can be varied without significant effect on the structure or function of the protein. If such differences in sequence are contemplated, it should be remembered that there will be critical areas on the protein which determine activity. Thus, the invention further includes variations of the PSGR receptor, which show substantial PSGR receptor activity or which include regions of PSGR proteins, such as the protein portions discussed herein. Such mutants include deletions, insertions, inversions, repeats, and type substitutions.

For example, guidance concerning how to make phenotypically silent amino acid substitutions is provided in Bowie et al., "Deciphering the Message in Protein Sequences: Tolerance to Amino Acid Substitutions," Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

For example, site directed changes at the amino acid level of PSGR can be made by replacing a particular amino acid with a conservative amino acid. Preferred conservative mutations include: M1 replaced with A, G, I, L, S, T, or V; S2 replaced with A, G, I, L, T, M, or V; S3 replaced with A, G, I, L, T, M, or V; N5 replaced with Q; F6 replaced with W, or Y; T7 replaced with A, G, I, L, S, M, or V; H8 replaced with K, or R; A9 replaced with G, I, L, S, T, M, or V; T10 replaced with A, G, I, L, S, M, or V; V12 replaced with A, G, I, L, S, T, or M; L13 replaced with A, G, , S, T, M, or V; I14 replaced with A, G, L, S, T, M, or V; G 15 replaced with A, I, L, S, T, M, or V; I16 replaced with A, G, L, S, T, M, or V; G18 replaced with A, I, L, S, T, M, or V; L19 replaced with A, G, I, S, T, M, or V; E20 replaced with D; K21 replaced with H, or R; A22 replaced with G, I, L, S, T, M, or V; H23 replaced with K, or R; F24 replaced with W, or Y; W25 replaced with F, or Y; V26 replaced with A, G, I, L, S, T, or M; G27 replaced with A, I, L, S, T, M, or V; F28 replaced with W, or Y; L30 replaced with A, G, I, S, T, M, or V; L31 replaced with A, G, I, S, T, M, or V; S32 replaced with A, G, I, L, T, M, or V; M33 replaced with A, G, I, L, S, T, or V; Y34 replaced with F, or W; V35 replaced with A, G, I, L, S, T, or M; V36 replaced with A, G, I, L, S, T, or M; A37 replaced with G, I, L, S, T, M, or V; M38 replaced with A, G, I, L, S, T, or V; G40 replaced with A, I, L, S, T, M, or V; N41 replaced with Q; I43 replaced with A, G, L, S, T, M, or V; V44 replaced with A, G, I, L, S, T, or M; V45 replaced with A, G, I, L, S, T, or M; F46 replaced with W, or Y; I47 replaced with A, G, L, S, T, M, or V; V48 replaced with A, G, I, L, S, T, or M; R49 replaced with H, or K; T50 replaced with A, G, I, L, S, M, or V; E51 replaced with D; R52 replaced with H, or K; S53 replaced with A, G, I, L, T, M, or V; L54 replaced with A, G, I, S, T, M, or V; H55 replaced with K, or R; A56 replaced with G, I, L, S, T, M, or V; M58 replaced with A, G, I, L, S, T, or V; Y59 replaced with F, or W; L60 replaced with A, G, I, S, T, M, or V; F61 replaced with W, or Y; L62 replaced with A, G, I, S, T, M, or V; M64 replaced with A, G, I, L, S, T, or V; L65 replaced with A, G, I, S, T, M, or V; A66 replaced with G, I, L, S, T, M, or V; A67 replaced with G, I, L, S, T, M, or V; I68 replaced with A, G, L, S, T, M, or V; D69 replaced with E; L70 replaced with A, G, I, S, T, M, or V; A71 replaced with G, I, L, S, T, M, or V; L72 replaced with A, G, I, S, T, M, or V; S73 replaced with A, G, I, L, T, M, or V; T74 replaced with A, G, I, L, S, M, or V; S75 replaced with A, G, I, L, T, M, or V; T76 replaced with A, G, I, L, S, M, or V; M77 replaced with A, G, I, L, S, T, or V; K79 replaced with H, or R; I80 replaced with A, G, L, S, T, M, or V; L81 replaced with A, G, I, S, T, M, or V; A82 replaced with G, I, L, S, T, M, or V; L83 replaced with A, G, I, S, T, M, or V; F84 replaced with W, or Y; W85 replaced with F, or Y; F86 replaced with W, or Y; D87 replaced with E; S88 replaced with A, G, I, L, T, M, or V; R89 replaced with H, or K; E90 replaced with D; I91 replaced with A, G, L, S, T, M, or V; S92 replaced with A, G, I, L, T, M, or V; I93 replaced with A, G, L, S, T, M, or V; E94 replaced with D; A95 replaced with G, I, L, S, T, M, or V; L97 replaced with A, G, I, S, T, M, or V; T98 replaced with A, G, I, L, S, M, or V; Q99 replaced with N; M100 replaced with A, G, I, L, S, T, or V; F101 replaced with W, or Y; F102 replaced with W, or Y; I103 replaced with A, G, L, S, T, M, or V; H104 replaced with K, or R; A105 replaced with G, I, L, S, T, M, or V; L106 replaced with A, G, I, S, T, M, or V; S107 replaced with A, G, I, L, T, M, or V; A108 replaced with G, I, L, S, T, M, or V; I109 replaced with A, G, L, S, T, M, or V; E110 replaced with D; S111 replaced with A, G, I, L, T, M, or V; T112 replaced with A, G, I, L, S, M, or V; I113 replaced with A, G, L, S, T, M, or V; L114 replaced with A, G, I, S, T, M, or V; L115 replaced with A, G, I, S, T, M, or V; A116 replaced with G, I, L, S, T, M, or V; M117 replaced with A, G, I, L, S, T, or V; A118 replaced with G, I, L, S, T, M, or V; F119 replaced with W, or Y; D120 replaced with E; R121 replaced with H, or K; Y122 replaced with F, or W; V123 replaced with A, G, I, L, S, T, or M; A124 replaced with G, I, L, S, T, M, or V; I125 replaced with A, G, L, S, T, M, or V; H127 replaced with K, or R; L129 replaced with A, G, I, S, T, M, or V; R130 replaced with H, or K; H131 replaced with K, or R; A132 replaced with G, I, L, S, T, M, or V; A133 replaced with G, I, L, S, T, M, or V; V134 replaced with A, G, I, L, S, T, or M; L135 replaced with A, G, I, S, T, M, or V; N136 replaced with Q; N137 replaced with Q; T138 replaced with A, G, I, L, S, M, or V; V139 replaced with A, G, I, L, S, T, or M; T140 replaced with A, G, I, L, S, M, or V; A141 replaced with G, I, L, S, T, M, or V; Q142 replaced with N; I143 replaced with A, G, L, S, T, M, or V; G144 replaced with A, I, L, S, T, M, or V; I145 replaced with A, G, L, S, T, M, or V; V146 replaced with A, G, I, L, S, T, or M; A147 replaced with G, I, L, S, T, M, or V; V148 replaced with A, G, I, L, S, T, or M; V149 replaced with A, G, I, L, S, T, or M; R150 replaced with H, or K; G151 replaced with A, I, L, S, T, M, or V; S152 replaced with A, G, I, L, T, M, or V; L153 replaced with A, G, I, S, T, M, or V; F154 replaced with W, or Y; F155 replaced with W, or Y; F156 replaced with W, or Y; L158 replaced with A, G, I, S, T, M, or V; L160 replaced with A, G, I, S, T, M, or V; L161 replaced with A, G, I, S, T, M, or V; I162 replaced with A, G, L, S, T, M, or V; K163 replaced with H, or R; R164 replaced with H, or K; L165 replaced with A, G, I, S, T, M, or V; A166 replaced with G, I, L, S, T, M, or V; F167 replaced with W, or Y; H169 replaced with K, or R; S170 replaced with A, G, I, L, T, M, or V; N171 replaced with Q; V172 replaced with A, G, I, L, S, T, or M; L173 replaced with A, G, I, S, T, M, or V; S174 replaced with A, G, I, L, T, M, or V; H175 replaced with K, or R; S176 replaced with A, G, I, L, T, M, or V; Y177 replaced with F, or W; V179 replaced with A, G, I, L, S, T, or M; H180 replaced with K, or R; Q181 replaced with N; D182 replaced with E; V183 replaced with A, G, I, L, S, T, or M; M184 replaced with A, G, I, L, S, T, or V; K185 replaced with H, or R; L186 replaced with A, G, I, S, T, M, or V; A187 replaced with G, I, L, S, T, M, or V; Y188 replaced with F, or W; A189 replaced with G, I, L, S, T, M, or V; D190 replaced with E; T191 replaced with A, G, I, L, S, M, or V; L192 replaced with A, G, I, S, T, M, or V; N194 replaced with Q; V195 replaced with A, G, I, L, S, T, or M; V196 replaced with A, G, I, L, S, T, or M; Y197 replaced with F, or W; G198 replaced with A, I, L, S, T, M, or V; L199 replaced with A, G, I, S, T, M, or V; T200 replaced with A, G, I, L, S, M, or V; A201 replaced with G, I, L, S, T, M, or V; I202 replaced with A, G, L, S, T, M, or V; L203 replaced with A, G, I, S, T, M, or V; L204 replaced with A, G, I, S, T, M, or V; V205 replaced with A, G, I, L, S, T, or M; M206 replaced with A, G, I, L, S, T, or V; G207 replaced with A, I, L, S, T, M, or V; V208 replaced with A, G, I, L, S, T, or M; D209 replaced with E; V210 replaced with A, G, I, L, S, T, or M; M211 replaced with A, G, I, L, S, T, or V; F212 replaced with W, or Y; I213 replaced with A, G, L, S, T, M, or V; S214 replaced with A, G, I, L, T, M, or V; L215 replaced with A, G, I, S, T, M, or V; S216 replaced with A, G, I, L, T, M, or V; Y217 replaced with F, or W; F218 replaced with W, or Y; L219 replaced with A, G, I, S, T, M, or V; I220 replaced with A, G, L, S, T, M, or V; I221 replaced with A, G, L, S, T, M, or V; R222 replaced with H, or K; T223 replaced with A, G, I, L, S, M, or V; V224 replaced with A, G, I, L, S, T, or M; L225 replaced with A, G, I, S, T, M, or V; Q226 replaced with N; L227 replaced with A, G, I, S, T, M, or V; S229 replaced with A, G, I, L, T, M, or V; K230 replaced with H, or R; S231 replaced with A, G, I, L, T, M, or V; E232 replaced with D; R233 replaced with H, or K; A234 replaced with G, I, L, S, T, M, or V; K235 replaced with H, or R; A236 replaced with G, I, L, S, T, M, or V; F237 replaced with W, or Y; G238 replaced with A, I, L, S, T, M, or V; T239 replaced with A, G, I, L, S, M, or V; V241 replaced with A, G, I, L, S, T, or M; S242 replaced with A, G, I, L, T, M, or V; H243 replaced with K, or R; I244 replaced with A, G, L, S, T, M, or V; G245 replaced with A, I, L, S, T, M, or V; V246 replaced with A, G, I, L, S, T, or M; V247 replaced with A, G, I, L, S, T, or M; L248 replaced with A, G, I, S, T, M, or V; A249 replaced with G, I, L, S, T, M, or V; F250 replaced with W, or Y; Y251 replaced with F, or W; V252 replaced with A, G, I, L, S, T, or M; L254 replaced with A, G, I, S, T, M, or V; I255 replaced with A, G, L, S, T, M, or V; G256 replaced with A, I, L, S, T, M, or V; L257 replaced with A, G, I, S, T, M, or V; S258 replaced with A, G, I, L, T, M, or V; V259 replaced with A, G, I, L, S, T, or M; V260 replaced with A, G, I, L, S, T, or M; H261 replaced with K, or R; R262 replaced with H, or K; F263 replaced with W, or Y; G264 replaced with A, I, L, S, T, M, or V; N265 replaced with Q; S266 replaced with A, G, I, L, T, M, or V; L267 replaced with A, G, I, S, T, M, or V; H268 replaced with K, or R; 1270 replaced with A, G, L, S, T, M, or V; V271 replaced with A, G, I, L, S, T, or M; R272 replaced with H, or K; V273 replaced with A, G, I, L, S, T, or M; V274 replaced with A, G, I, L, S, T, or M; M275 replaced with A, G, I, L, S, T, or V; G276 replaced with A, I, L, S, T, M, or V; D277 replaced with E; I278 replaced with A, G, L, S, T, M, or V; Y279 replaced with F, or W; L280 replaced with A, G, I, S, T, M, or V; L281 replaced with A, G, I, S, T, M, or V; L282 replaced with A, G, I, S, T, M, or V; V285 replaced with A, G, I, L, S, T, or M; I286 replaced with A, G, L, S, T, M, or V; N287 replaced with Q; O289 replaced with A, G, L, S, T, M, or V; I290 replaced with A, G, L, S, T, M, or V; Y291 replaced with F, or W; G292 replaced with A, I, L, S, T, M, or V; A293 replaced with G, I, L, S, T, M, or V; K294 replaced with H, or R; T295 replaced with A, G, I, L, S, M, or V; K296 replaced with H, or R; Q297 replaced with N; I298 replaced with A, G, L, S, T, M, or V; R299 replaced with H, or K; T300 replaced with A, G, I, L, S, M, or V; R301 replaced with H, or K; V302 replaced with A, G, I, L, S, T, or M; L303 replaced with A, G, I, S, T, M, or V; A304 replaced with G, I, L, S, T, M, or V; M305 replaced with A, G, I, L, S, T, or V; F306 replaced with W, or Y; K307 replaced with H, or R; I308 replaced with A, G, L, S, T, M, or V; S309 replaced with A, G, I, L, T, M, or V; D311 replaced with E; K312 replaced with H, or R; D313 replaced with E; L314 replaced with A, G, I, S, T, M, or V; Q315 replaced with N; A316 replaced with G, I, L, S, T, M, or V; V317 replaced with A, G, I, L, S, T, or M;

G318 replaced with A, I, L, S, T, M, or V; G319 replaced with A, I, L, S, T, M, or V; and/or K320 replaced with H, or R in the PSGR amino acid sequence shown in FIGS. 1A–B (SEQ ID NO:2).

The resulting constructs can be routinely screened for activities or functions described throughout the specification and known in the art. Preferably, the resulting constructs have an increased and/or a decreased PSGR activity or function, while the remaining PSGR activities or functions are maintained. More preferably, the resulting constructs have more than one increased and/or decreased PSGR activity or function, while the remaining PSGR activities or functions are maintained.

Besides conservative amino acid substitution, variants of PSGR include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification or (v) fusion of the the polypeptide with another compound, such as albumin (including but not limited to recombinant albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). Such variant polypeptides are deemed to be within the scope of those skilled in the art from the teachings herein.

For example, PSGR polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

For example, preferred non-conservative substitutions of PSGR include M1 replaced with D, E, H, K, R, N, Q, F, W, Y, P, or C; S2 replaced with D, E, H, K, R, N, Q, F, W, Y, P, or C; S3 replaced with D, E, H, K, R, N, Q, F, W, Y, P, or C; C4 replaced with D, E, H, K, R, A, G, I, L, S, T,M, V,N, Q,F, W, Y, or P; N5 replaced with D, E,H, K,R, A, G, I, L, S, T, M, V, F, W, Y, P, or C; F6 replaced with D, E, H, K, R, N, Q, A, G, I, L, S, T, M, V, P, or C; T7 replaced with D, E, H, K, R, N, Q, F, W, Y, P, or C; H8 replaced with D, E, A, G, I, L, S, T, M, V, N, Q, F, W, Y, P, or C; A9 replaced with D, E, H, K, R, N, Q, F, W, Y, P, or C; T10 replaced with D, E, H, K, R, N, Q, F, W, Y, P, or C; C11 replaced with D, E, H, K, R, A, G, I, L, S, T, M, V, N, Q, F, W, Y, or P; V12 replaced with D, E, H, K, R, N, Q, F, W, Y, P, or C; L13 replaced with D, E, H, K, R, N, Q, F, W, Y, P, or C; I14 replaced with D, E, H, K, R, N, Q, F, W, Y, P, or C; G15 replaced with D, E, H, K, R, N, Q, F, W, Y, P, or C; I16 replaced with D, E, H, K, R, N, Q, F, W, Y, P, or C; P17 replaced with D, E, H, K, R, A, G, I, L, S, T, M, V, N, Q, F, W, Y, or C; G18 replaced with D, E, H, K, R, N, Q, F, W, Y, P, or C; L19 replaced with D, E, H, K, R, N, Q, F, W, Y, P, or C; E20 replaced with H, K, R, A, G, I, L, S, T, M, V, N, Q, F, W, Y, P, or C; K21 replaced with D, E, A, G, I, L, S, T, M, V, N, Q, F, W, Y, P, or C; A22 replaced with D, E, H, K, R, N, Q, F, W, Y, P, or C; H23 replaced with D, E, A, G, I, L, S, T, M, V, N, Q, F, W, Y, P, or C; F24 replaced with D, E, H, K, R, N, Q, A, G, I, L, S, T, M, V, P, or C; W25 replaced with D, E, H, K, R, N, Q, A, G, I, L, S, T, M, V, P, or C; V26 replaced with D, E, H, K, R, N, Q, F, W, Y, P, or C; G27 replaced with D, E, H, K, R, N, Q, F, W, Y, P, or C; F28 replaced with D, E, H, K, R, N, Q, A, G, I, L, S, T, M, V, P, or C; P29 replaced with D, E, H, K, R, A, G, I, L, S, T, M, V, N, Q, F, W, Y, or C; L30 replaced with D, E, H, K, R, N, Q, F, W, Y, P, or C; L31 replaced with D, E, H, K, R, N, Q, F, W, Y, P, or C; S32 replaced with D, E, H, K, R, N, Q, F, W, Y, P, or C; M33 replaced with D, E, H, K, R, N, Q, F, W, Y, P, or C; Y34 replaced with D, E, H, K, R, N, Q, A, G, I, L, S, T, M, V, P, or C; V35 replaced with D, E, H, K, R, N, Q, F, W, Y, P, or C; V36 replaced with D, E, H, K, R, N, Q, F, W, Y, P, or C; A37 replaced with D, E, H, K, R, N, Q, F, W, Y, P, or C; M38 replaced with D, E, H, K, R, N, Q, F, W, Y, P, or C; C39 replaced with D, E, H, K, R, A, G, I, L, S, T, M, V, N, Q, F, W, Y, or P; G40 replaced with D, E, H, K, R, N, Q, F, W, Y, P, or C; N41 replaced with D, E, H, K, R, A, G, I, L, S, T, M, V, F, W, Y, P, or C; C42 replaced with D, E, H, K, R, A, G, I, L, S, T, M, V, N, Q, F, W, Y, or P; I43 replaced with D, E, H, K, R, N, Q, F, W, Y, P, or C; V44 replaced with D, E, H, K, R, N, Q, F, W, Y, P, or C; V45 replaced with D, E, H, K, R, N, Q, F, W, Y, P, or C; F46 replaced with D, E, H, K, R, N, Q, A, G, I, L, S, T, M, V, P, or C; I47 replaced with D, E, H, K, R, N, Q, F, W, Y, P, or C; V48 replaced with D, E, H, K, R, N, Q, F, W, Y, P, or C; R49 replaced with D, E, A, G, I, L, S, T, M, V, N, Q, F, W, Y, P, or C; T50 replaced with D, E, H, K, R, N, Q, F, W, Y, P, or C; E51 replaced with H, K, R, A, G, I, L, S, T, M, V, N, Q, F, W, Y, P, or C; R52 replaced with D, E, A, G, I, L, S, T, M, V, N, Q, F, W, Y, P, or C; S53 replaced with D, E, H, K, R, N, Q, F, W, Y, P, or C; L54 replaced with D, E, H, K, R, N, Q, F, W, Y, P, or C; H55 replaced with D, E, A, G, I, L, S, T, M, V, N, Q, F, W, Y, P, or C; A56 replaced with D, E, H, K, R, N, Q, F, W, Y, P, or C; P57 replaced with D, E, H, K, R, A, G, I, L, S, T, M, V, N, Q, F, W, Y, or C; M58 replaced with D, E, H, K, R, N, Q, F, W, Y, P, or C; Y59 replaced with D, E, H, K, R, N, Q, A, G, I, L, S, T, M, V, P, or C; L60 replaced with D, E, H, K, R, N, Q, F, W, Y, P, or C; F61 replaced with D, E, H, K, R, N, Q, A, G, I, L, S, T, M, V, P, or C; L62 replaced with D, E, H, K, R, N, Q, F, W, Y, P, or C; C63 replaced with D, E, H, K, R, A, G, I, L, S, T, M, V, N, Q, F, W, Y, or P; M64 replaced with D, E, H, K, R, N, Q, F, W, Y, P, or C; L65 replaced with D, E, H, K, R, N, Q, F, W, Y, P, or C; A66 replaced with D, E, H, K, R, N, Q, F, W, Y, P, or C; A67 replaced with D, E, H, K, R, N, Q, F, W, Y, P, or C; I68 replaced with D, E, H, K, R, N, Q, F, W, Y, P, or C; D69 replaced with H, K, R, A, G, I, L, S, T, M, V, N, Q, F, W, Y, P, or C; L70 replaced with D, E, H, K, R, N, Q, F, W, Y, P, or C; A71 replaced with D, E, H, K, R, N, Q, F, W, Y, P, or C; L72 replaced with D, E, H, K, R, N, Q, F, W, Y, P, or C; S73 replaced with D, E, H, K, R, N, Q, F, W, Y, P, or C; T74 replaced with D, E, H, K, R, N, Q, F, W, Y, P, or C; S75replaced with D, E, H, K, R, N, Q, F, W, Y, P, or C; T76 replaced with D, E, H, K, R, N, Q, F, W, Y, P, or C; M77 replaced with D, E, H, K, R, N, Q, F, W, Y, P, or C; P78 replaced with D, E, H, K, R, A, G, I, L, S, T, M, V, N, Q, F, W, Y, or C; K79 replaced with D, E, A, G, I, L, S, T, M, V, N, Q, F, W, Y, P, or C; I80 replaced with D, E, H, K, R, N, Q, F, W, Y, P, or C; L81 replaced with D, E, H, K, R, N, Q, F, W, Y, P, or C; A82 replaced with D, E, H, K, R, N, Q, F, W, Y, P, or C; L83 replaced with D, E, H, K, R, N, Q, F, W, Y, P, or C; F84 replaced with D, E, H, K, R, N, Q, A, G, I, L, S, T, M, V, P, or C; W85 replaced with D, E, H, K, R, N, Q, A, G, I, L, S, T, M, V, P, or C; F86 replaced with D, E, H, K, R, N, Q, A, G, I, L, S, T, M, V, P, or C; D87 replaced with H, K, R, A, G, I, L, S, T, M, V, N, Q, F, W, Y, P, or C; S88 replaced with D, E, H, K, R, N, Q, F, W, Y, P, or C; R89 replaced with D, E, A, G, I, L, S, T, M, V, N, Q, F, W, Y, P, or C; E90 replaced with H, K, R, A, G, I, L, S, T, M, V, N, Q, F, W, Y, P, or C; I91 replaced with D, E, H, K, R, N, Q, F, W, Y, P, or C; S92 replaced with D, E, H, K, R, N, Q, F, W, Y, P, or C; I93 replaced with D, E, H, K, R, N, Q, F, W, Y, P, or C; E94 replaced with H, K, R, A, G, I, L, S, T, M, V, N, Q, F, W, Y, P, or C; A95 replaced with D, E, H, K, R, N, Q, F, W, Y, P, or C; C96 replaced with D, E, H, K, R, A, G, I, L, S, T, M, V, N, Q, F, W, Y, or P; L97 replaced with D, E, H, K, R, N, Q, F, W, Y, P, or C; T98 replaced with D, E, H, K, R, N, Q, F, W, Y, P, or C; Q99 replaced with D, E, H, K, R, A, G, I, L, S, T, M, V, F, W, Y, P, or C; M100 replaced with D, E, H, K, R, N, Q, F, W, Y, P, or C; F101 replaced with D, E, H, K, R, N, Q, A, G, I, L, S, T, M, V, P, or C; F102 replaced with D, E, H, K, R, N, Q, A, G, I, L, S, T, M, V, P, or C; I103 replaced with D, E, H, K, R, N, Q, F, W, Y, P, or C; H104 replaced with D, E, A, G, I, L, S, T, M, V, N, Q, F, W, Y, P, or C; A105 replaced with D, E, H, K, R, N, Q, F, W, Y, P, or C; L106 replaced with D, E, H, K, R, N, Q, F, W, Y, P, or C; S107 replaced with D, E, H, K, R, N, Q, F, W, Y, P, or C; A108 replaced with D, E, H, K, R, N, Q, F, W, Y, P, or C; I109 replaced with D, E, H, K, R, N, Q, F, W, Y, P, or C; E110 replaced with H, K, R, A, G, I, L, S, T, M, V, N, Q, F, W, Y, P, or C; S111 replaced with D, E, H, K, R, N, Q, F, W, Y, P, or C; T112 replaced with D, E, H, K, R, N, Q, F, W, Y, P, or C; I113 replaced with D, E, H, K, R, N, Q, F, W, Y, P, or C; L114 replaced with D, E, H, K, R, N, Q, F, W, Y, P, or C; L 115 replaced with D, E, H, K, R, N, Q, F, W, Y, P, or C; A116 replaced with D, E, H, K, R, N, Q, F, W, Y, P, or C; M117 replaced with D, E, H, K, R, N, Q, F, W, Y, P, or C; A118 replaced with D, E, H, K, R, N, Q, F, W, Y, P, or C; F119 replaced with D, E, H, K, R, N, Q, A, G, I, L, S, T, M, V, P, or C; D120 replaced with H, K, R, A, G, I, L, S, T, M, V, N, Q, F, W, Y, P, or C; R121 replaced with D, E, A, G, I, L, S, T, M, V, N, Q, F, W, Y, P, or C; Y122 replaced with D, E, H, K, R, N, Q, A, G, I, L, S, T, M, V, P, or C; V123 replaced with D, E, H, K, R, N, Q, F, W, Y, P, or C; A124 replaced with D, E, H, K, R, N, Q, F, W, Y, P, or C; I125 replaced with D, E, H, K, R, N, Q, F, W, Y, P, or C; C126 replaced with D, E, H, K, R, A, G, I, L, S, T, M, V, N, Q, F, W, Y, or P; H127 replaced with D, E, A, G, I, L, S, T, M, V, N, Q, F, W, Y, P, or C; P128 replaced with D, E, H, K, R, A, G, I, L, S, T, M, V, N, Q, F, W, Y, or C; L129 replaced with D, E, H, K, R, N, Q, F, W, Y, P, or C; R130 replaced with D, E, A, G, I, L, S, T, M, V, N, Q, F, W, Y, P, or C; H131 replaced with D, E, A, G, I, L, S, T, M, V, N, Q, F, W, Y, P, or C; A132 replaced with D, E, H, K, R, N, Q, F, W, Y, P, or C; A133 replaced with D, E, H, K, R, N, Q, F, W, Y, P, or C; V134 replaced with D, E, H, K, R, N, Q, F, W, Y, P, or C; L135 replaced with D, E, H, K, R, N, Q, F, W, Y, P, or C; N136 replaced with D, E, H, K, R, A, G, I, L, S, T, M, V, F, W, Y, P, or C; N137 replaced with D, E, H, K, R, A, G, I, L, S, T, M, V, F, W, Y, P, or C; T138 replaced with D, E, H, K, R, N, Q, F, W, Y, P, or C; V139 replaced with D, E, H, K, R, N, Q, F, W, Y, P, or C; T140 replaced with D, E, H, K, R, N, Q, F, W, Y, P, or C; A141 replaced with D, E, H, K, R, N, Q, F, W, Y, P, or C; Q142 replaced with D, E, H, K, R, A, G, I, L, S, T, M, V, F, W, Y, P, or C; I143 replaced with D, E, H, K, R, N, Q, F, W, Y, P, or C; G144 replaced with D, E, H, K, R, N, Q, F, W, Y, P, or C; I145 replaced with D, E, H, K, R, N, Q, F, W, Y, P, or C; V146 replaced with D, E, H, K, R, N, Q, F, W, Y, P, or C; A147 replaced with D, E, H, K, R, N, Q, F, W, Y, P, or C; V148 replaced with D, E, H, K, R, N, Q, F, W, Y, P, or C; V149 replaced with D, E, H, K, R, N, Q, F, W, Y, P, or C; R150 replaced with D, E, A, G, I, L, S, T, M, V, N, Q, F, W, Y, P, or C; G151 replaced with D, E, H, K, R, N, Q, F, W, Y, P, or C; S152 replaced with D, E, H, K, R, N, Q, F, W, Y, P, or C; L153 replaced with D, E, H, K, R, N, Q, F, W, Y, P, or C; F154 replaced with D, E, H, K, R, N, Q, A, G, I, L, S, T, M, V, P, or C; F155 replaced with D, E, H, K, R, N, Q, A, G, I, L, S, T, M, V, P, or C; F156 replaced with D, E, H, K, R, N, Q, A, G, I, L, S, T, M, V, P, or C; P157 replaced with D, E, H, K, R, A, G, I, L, S, T, M, V, N, Q, F, W, Y, or C; L158 replaced with D, E, H, K, R, N, Q, F, W, Y, P, or C; P159 replaced with D, E, H, K, R, A, G, I, L, S, T, M, V, N, Q, F, W, Y, or C; L160 replaced with D, E, H, K, R, N, Q, F, W, Y, P, or C; L161 replaced with D, E, H, K, R, N, Q, F, W, Y, P, or C; I162 replaced with D, E, H, K, R, N, Q, F, W, Y, P, or C; K163 replaced with D, E, A, G, I, L, S, T, M, V, N, Q, F, W, Y, P, or C; R164 replaced with D, E, A, G, 1, L, S, T, M, V, N, Q, F, W, Y, P, or C; L165 replaced with D, E, H, K, R, N, Q, F, W, Y, P, or C; A166 replaced with D, E, H, K, R, N, Q, F, W, Y, P, or C; F167 replaced with D, E, H, K, R, N, Q, A, G, I, L, S, T, M, V, P, or C; C168 replaced with D, E, H, K, R, A, G, I, L, S, T, M, V, N, Q, F, W, Y, or P; H169 replaced with D, E, A, G, I, L, S, T, M, V, N, Q, F, W, Y, P, or C; S170 replaced with D, E, H, K, R, N, Q, F, W, Y, P, or C; N171 replaced with D, E, H, K, R, A, G, I, L, S, T, M, V, F, W, Y, P, or C; V172 replaced with D, E, H, K, R, N, Q, F, W, Y, P, or C; L173 replaced with D, E, H, K, R, N, Q, F, W, Y, P, or C; S174 replaced with D, E, H, K, R, N, Q, F, W, Y, P, or C; H175 replaced with D, E, A, G, I, L, S, T, M, V, N, Q, F, W, Y, P, or C; S176 replaced with D, E, H, K, R, N, Q, F, W, Y, P, or C; Y177 replaced with D, E, H, K, R, N, Q, A, G, I, L, S, T, M, V, P, or C; C178 replaced with D, E, H, K, R, A, G, I, L, S, T, M, V, N, Q, F, W, Y, or P; V179 replaced with D, E, H, K, R, N, Q, F, W, Y, P, or C; H180 replaced with D, E, A, G, I, L, S, T, M, V, N, Q, F, W, Y, P, or C; Q181 replaced with D, E, H, K, R, A, G, I, L, S, T, M, V, F, W, Y, P, or C; D182 replaced with H, K, R, A, G, I, L, S, T, M, V, N, Q, F, W, Y, P, or C; V183 replaced with D, E, H, K, R, N, Q, F, W, Y, P, or C; M184 replaced with D, E, H, K, R, N, Q, F, W, Y, P, or C; K185 replaced with D, E, A, G, I, L, S, T, M, V, N, Q, F, W, Y, P, or C; L186 replaced with D, E, H, K, R, N, Q, F, W, Y, P, or C; A187 replaced with D, E, H, K, R, N, Q, F, W, Y, P, or C; Y188 replaced with D, E, H, K, R, N, Q, A, G, I, L, S, T, M, V, P, or C; A189 replaced with D, E, H, K, R, N, Q, F, W, Y, P, or C; D190 replaced with H, K, R, A, G, I, L, S, T, M, V, N, Q, F, W, Y, P, or C; T191 replaced with D, E, H, K, R, N, Q, F, W, Y, P, or C; L192 replaced with D, E, H, K, R, N, Q, F, W, Y, P, or C; P193 replaced with D, E, H, K, R, A, G, I, L, S, T, M, V, N, Q, F, W, Y, or C; N194 replaced with D, E, H, K, R, A, G, I, L, S, T, M, V, F, W, Y, P, or C; V195 replaced with D, E, H, K, R, N, Q, F, W, Y, P, or C; V196 replaced with D, E, H, K, R, N, Q, F, W, Y, P, or C; Y197 replaced with D, E, H, K, R, N, Q, A, G, I, L, S, T, M, V, P, or C; G198 replaced with D, E, H, K, R, N, Q, F, W, Y, P, or C; L199 replaced with D, E, H, K, R, N, Q, F, W, Y, P, or C; T200 replaced with D, E, H, K, R, N, Q, F, W, Y, P, or C; A201 replaced with D, E, H, K, R, N, Q, F, W, Y, P, or C; I202 replaced with D, E, H, K, R, N, Q, F, W, Y, P, or C; L203 replaced with D, E, H, K, R, N, Q, F, W, Y, P, or C; L204 replaced with D, E, H, K, R, N, Q, F, W, Y, P, or C; V205 replaced with D, E, H, K, R, N, Q, F, W, Y, P, or C; M206 replaced with D, E, H, K, R, N, Q, F, W, Y, P, or C; G207 replaced with D, E, H, K, R, N, Q, F, W, Y, P, or C; V208 replaced with D, E, H, K, R, N, Q, F, W, Y, P, or C; D209 replaced with H, K, R, A, G, I, L, S, T, M, V, N, Q, F, W, Y, P, or C; V210 replaced with D, E, H, K, R, N, Q, F, W, Y, P, or C; M211 replaced with D, E, H, K, R, N, Q, F, W, Y, P, or C; F212 replaced with D, E, H, K, R, N, Q, A, G, I, L, S, T, M, V, P, or C; I213 replaced with D, E, H, K, R, N, Q, F, W, Y, P, or C; S214 replaced with D, E, H, K, R, N, Q, F, W, Y, P, or C; L215 replaced with D, E, H, K, R, N, Q, F, W, Y, P, or C; S216 replaced with D, E, H, K, R, N, Q, F, W, Y, P, or C; Y217 replaced with D, E, H, K, R, N, Q, A, G, I, L, S, T, M, V, P, or C; F218 replaced with D, E, H, K, R, N, Q, A, G, I, L, S, T, M, V, P, or C; L219 replaced with D, E, H, K, R, N, Q, F, W, Y, P, or C; I220 replaced with D, E, H, K, R, N, Q, F, W, Y, P, or C; I221 replaced with D, E, H, K, R, N, Q, F, W, Y, P, or C; R222 replaced with D, E, A, G, I, L, S, T, M, V, N, Q, F, W, Y, P, or C; T223 replaced with D, E, H, K, R, N, Q, F, W, Y, P, or C; V224 replaced with D, E, H, K, R, N, Q, F, W, Y, P, or C; L225 replaced with D, E, H, K, R, N, Q, F, W, Y, P, or C; Q226 replaced with D, E, H, K, R, A, G, I, L, S, T, M, V, F, W, Y, P, or C; L227 replaced with D, E, H, K, R, N, Q, F, W, Y, P, or C; P228 replaced with D, E, H, K, R, A, G, I, L, S, T, M, V, N, Q, F, W, Y, or C; S229 replaced with D, E, H, K, R, N, Q, F, W, Y, P, or C; K230 replaced with D, E, A, G, I, L, S, T, M, V, N, Q, F, W, Y, P, or C; S231 replaced with D, E, H, K, R, N, Q, F, W, Y, P, or C; E232 replaced with H, K, R, A, G, I, L, S, T, M, V, N, Q, F, W, Y, P, or C; R233 replaced with D, E, A, G, I, L, S, T, M, V, N, Q, F, W, Y, P, or C; A234 replaced with D, E, H, K, R, N, Q, F, W, Y, P, or C; K235 replaced with D, E, A, G, I, L, S, T, M, V, N, Q, F, W, Y, P, or C; A236 replaced with D, E, H, K, R, N, Q, F, W, Y, P, or C; F237 replaced with D, E, H, K, R, N, Q, A, G, I, L, S, T, M, V, P, or C; G238 replaced with D, E, H, K, R, N, Q, F, W, Y, P, or C; T239 replaced with D, E, H, K, R, N, Q, F, W, Y, P, or C; C240 replaced with D, E, H, K, R, A, G, I, L, S, T, M, V, N, Q, F, W, Y, or P; V241 replaced with D, E, H, K, R, N, Q, F, W, Y, P, or C; S242 replaced with D, E, H, K, R, N, Q, F, W, Y, P, or C; H243 replaced with D, E, A, G, I, L, S, T, M, V, N, Q, F, W, Y, P, or C; I244 replaced with D, E, H, K, R, N, Q, F, W, Y, P, or C; G245 replaced with D, E, H, K, R, N, Q, F, W, Y, P, or C; V246 replaced with D, E, H, K, R, N, Q, F, W, Y, P, or C; V247 replaced with D, E, H, K, R, N, Q, F, W, Y, P, or C; L248 replaced with D, E, H, K, R, N, Q, F, W, Y, P, or C; A249 replaced with D, E, H, K, R, N, Q, F, W, Y, P, or C; F250 replaced with D, E, H, K, R, N, Q, A, G, I, L, S, T, M, V, P, or C; Y251 replaced with D, E, H, K, R, N, Q, A, G, I, L, S, T, M, V, P, or C; V252 replaced with D, E, H, K, R, N, Q, F, W, Y, P, or C; P253 replaced with D, E, H, K, R, A, G, I, L, S, T, M, V, N, Q, F, W, Y, or C; L254 replaced with D, E, H, K, R, N, Q, F, W, Y, P, or C; I255 replaced with D, E, H, K, R, N, Q, F, W, Y, P, or C; G256 replaced with D, E, H, K, R, N, Q, F, W, Y, P, or C; L257 replaced with D, E, H, K, R, N, Q, F, W, Y, P, or C; S258 replaced with D, E, H, K, R, N, Q, F, W, Y, P, or C; V259 replaced with D, E, H, K, R, N, Q, F, W, Y, P, or C; V260 replaced with D, E, H, K, R, N, Q, F, W, Y, P, or C; H261 replaced with D, E, A, G, I, L, S, T, M, V, N, Q, F, W, Y, P, or C; R262 replaced with D, E, A, G, I, L, S, T, M, V, N, Q, F, W, Y, P, or C; F263 replaced with D, E, H, K, R, N, Q, A, G, I, L, S, T, M, V, P, or C; G264 replaced with D, E, H, K, R, N, Q, F, W, Y, P, or C; N265 replaced with D, E, H, K, R, A, G, I, L, S, T, M, V, F, W, Y, P, or C; S266 replaced with D, E, H, K, R, N, Q, F, W, Y, P, or C; L267 replaced with D, E, H, K, R, N, Q, F, W, Y, P, or C; H268 replaced with D, E, A, G, I, L, S, T, M, V, N, Q, F, W, Y, P, or C; P269 replaced with D, E, H, K, R, A, G, I, L, S, T, M, V, N, Q, F, W, Y, or C; I270 replaced with D, E, H, K, R, N, Q, F, W, Y, P, or C; V271 replaced with D, E, H, K, R, N, Q, F, W, Y, P, or C; R272 replaced with D, E, A, G, I, L, S, T, M, V, N, Q, F, W, Y, P, or C; V273 replaced with D, E, H, K, R, N, Q, F, W, Y, P, or C; V274 replaced with D, E, H, K, R, N, Q, F, W, Y, P, or C; M275 replaced with D, E, H, K, R, N, Q, F, W, Y, P, or C; G276 replaced with D, E, H, K, R, N, Q, F, W, Y, P, or C; D277 replaced with H, K, R, A, G, I, L, S, T, M, V, N, Q, F, W, Y, P, or C; I278 replaced with D, E, H, K, R, N, Q, F, W, Y, P, or C; Y279 replaced with D, E, H, K, R, N, Q, A, G, I, L, S, T, M, V, P, or C; L280 replaced with D, E, H, K, R, N, Q, F, W, Y, P, or C; L281 replaced with D, E, H, K, R, N, Q, F, W, Y, P, or C; L282 replaced with D, E, H, K, R, N, Q, F, W, Y, P, or C; P283 replaced with D, E, H, K, R, A, G, I, L, S, T, M, V, N, Q, F, W, Y, or C; P284 replaced with D, E, H, K, R, A, G, I, L, S, T, M, V, N, Q, F, W, Y, or C; V285 replaced with D, E, H, K, R, N, Q, F, W, Y, P, or C; I286 replaced with D, E, H, K, R, N, Q, F, W, Y, P, or C; N287 replaced with D, E, H, K, R, A, G, I, L, S, T, M, V, F, W, Y, P, or C; P288 replaced with D, E, H, K, R, A, G, I, L, S, T, M, V, N, Q, F, W, Y, or C; I289 replaced with D, E, H, K, R, N, Q, F, W, Y, P, or C; I290 replaced with D, E, H, K, R, N, Q, F, W, Y, P, or C; Y291 replaced with D, E, H, K, R, N, Q, A, G, I, L, S, T, M, V, P, or C; G292 replaced with D, E, H, K, R, N, Q, F, W, Y, P, or C; A293 replaced with D, E, H, K, R, N, Q, F, W, Y, P, or C; K294 replaced with D, E, A, G, I, L, S, T, M, V, N, Q, F, W, Y, P, or C; T295 replaced with D, E, H, K, R, N, Q, F, W, Y, P, or C; K296 replaced with D, E, A, G, I, L, S, T, M, V, N, Q, F, W, Y, P, or C; Q297 replaced with D, E, H, K, R, A, G, I, L, S, T, M, V, F, W, Y, P, or C; I298 replaced with D, E, H, K, R, N, Q, F, W, Y, P, or C; R299 replaced with D, E, A, G, I, L, S, T, M, V, N, Q, F, W, Y, P, or C; T300 replaced with D, E, H, K, R, N, Q, F, W, Y, P, or C; R301 replaced with D, E, A, G, I, L, S, T, M, V, N, Q, F, W, Y, P, or C; V302 replaced with D, E, H, K, R, N, Q, F, W, Y, P, or C; L303 replaced with D, E, H, K, R, N, Q, F, W, Y, P, or C; A304 replaced with D, E, H, K, R, N, Q, F, W, Y, P, or C; M305 replaced with D, E, H, K, R, N, Q, F, W, Y, P, or C; F306 replaced with D, E, H, K, R, N, Q, A, G, I, L, S, T, M, V, P, or C; K307 replaced with D, E, A, G, I, L, S, T, M, V, N, Q, F, W, Y, P, or C; I308 replaced with D, E, H, K, R, N, Q, F, W, Y, P, or C; S309 replaced with D, E, H, K, R, N, Q, F, W, Y, P, or C; C310 replaced with D, E, H, K, R, A, G, I, L, S, T, M, V, N, Q, F, W, Y, orP; D311 replaced with H, K, R, A, G, I, L, S, T, M, V, N, Q, F, W, Y, P, or C; K312 replaced with D, E, A, G, I, L, S, T, M, V, N, Q, F, W, Y, P, or C; D313 replaced with H, K, R, A, G, I, L, S, T, M, V, N, Q, F, W, Y, P, or C; L314 replaced with D, E, H, K, R, N, Q, F, W, Y, P, or C; Q315 replaced with D, E, H, K, R, A, G, I, L, S, T, M, V, F, W, Y, P, or C; A316 replaced with D, E, H, K, R, N, Q, F, W, Y, P, or C; V317 replaced with D, E, H, K, R, N, Q, F, W, Y, P, or C; G318 replaced with D, E, H, K, R, N, Q, F, W, Y, P, or C; G319 replaced with D, E, H, K, R, N, Q, F, W, Y, P, or C; and/or K320 replaced with D, E, A, G, I, L, S, T, M, V, N, Q, F, W, Y, P, or C of the PSGR amino acid sequence shown in FIGS. 1A–B (SEQ ID NO:2).

The resulting constructs can be routinely screened for activities or functions described throughout the specification and known in the art. Preferably, the resulting constructs have an increased and/or decreased PSGR activity or function, while the remaining PSGR activities or functions are maintained. More preferably, the resulting constructs have more than one increased and/or decreased PSGR activity or function, while the remaining PSGR activities or functions are maintained.

Additionally, more than one amino acid (e.g., 2, 3, 4, 5, 6, 7, 8, 9 and 10) can be replaced with the substituted amino acids as described above (either conservative or nonconservative). The substituted amino acids can occur in the full length, mature, or proprotein form of PSGR protein, as well as the N- and C- terminal deletion mutants, having the general formula $n^1$-$m^1$, listed above.

A further embodiment of the invention relates to a polypeptide which comprises the amino acid sequence of a PSGR polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polypeptide to have an amino acid sequence which comprises the amino acid sequence of a PSGR polypeptide, which contains at least one, but not more than 10, 9, 8, 7, 6, 5, 4, 3, 2 or 1 amino acid substitutions. In specific embodiments, the number of additions, substitutions, and/or deletions in the amino acid sequence of FIGS. 1A–B or fragments thereof (e.g., the mature form and/or other fragments described herein), is 1–5, 5–10, 5–25, 5–50, 10–50 or 50–150, conservative amino acid substitutions are preferable.

Preferred substitutions include F11 replaced with C; F39 replaced with C; and F93 replaced with I of the PSGR amino acid sequence shown in FIGS. 1A–B (SEQ ID NO:2). Polynucleotides encoding these polypeptides are also encompassed by the invention.

Thus, the fragment, derivative, or analog of the polypeptide of FIGS. 1A–B (SEQ ID NO:2), or a polypeptide of FIGS. 2A–B (SEQ ID NO:4), or a polypeptide encoded by of the cDNA in ATCC Deposit No. 97131, may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence or (v) one in which the mature polypeptide is fused with another compound, such as albumin (including but not limited to recombinant albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). Such fragments, derivatives and analogs are deemed to be within the scope of those skilled in the art from the teachings herein.

The replacement of amino acids can also change the selectivity of binding to cell surface receptors. Ostade et al., *Nature* 361:266–268 (1993), describes certain mutations resulting in selective binding of TNF-α to only one of the two known types of TNF receptors. Thus, the PSGR polypeptides of the present invention may include one or more amino acid substitutions, deletions, or additions, either from natural mutations or human manipulation.

In specific embodiments, the number of substitutions, additions or deletions in the amino acid sequence of FIGS. 1A–B and/or any of the polypeptide fragments described herein (e.g., the extracellular domain, transmembrane domains, or intracellular domain) is 75, 70, 60, 50, 40, 35, 30, 25, 20, 15, 10, 9, 8, 7, 6, 5, 4, 3, 2, 1 or 30–20, 20–15, 20–10, 15–10, 10–1, 5–10, 1–5, 1–3 or 1–2.

Amino acids in the PSGR proteins of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

To improve or alter the characteristics of PSGR polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res*. 13:4331 (1986); and Zoller et al., *Nucl. Acids Res*. 10:6487 (1982)), cassette mutagenesis (see e.g., Wells et al., *Gene* 34:315 (1985)), restriction selection mutagenesis (see e.g., Wells et al., *Philos. Trans. R. Soc. London SerA* 317:415 (1986)).

Thus, the invention also encompasses PSGR derivatives and analogs that have one or more amino acid residues deleted, added, or substituted to generate PSGR polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognitions sequences in the PSGR polypeptides of the invention, and/or an amino acid deletion at the second position of any one or more such recognition sequences will prevent glycosylation of the PSGR at the modified tripeptide sequence (see, e.g., Miyajimo et al., *EMBO J* 5(6): 1193–1197). Additionally, one or more of the amino acid residues of the polypeptides of the invention (e.g., arginine and lysine residues) may be deleted or substituted with another residue to eliminate undesired processing by proteases such as, for example, furins or kexins.

The polypeptides of the present invention include a polypeptide comprising, or alternatively, consisting of a polypeptide having the amino acid sequence encoded by the cDNA in ATCC Deposit No. 97131; a polypeptide comprising, or alternatively, consisting of a polypeptide having the amino acid sequence encoded by the cDNA in ATCC Deposit No. 97131 minus the N terminal methionine; a polypeptide comprising, or alternatively, consisting of amino acids from about 1 to about 320 in FIGS. 1A–B (SEQ ID NO:2); a polypeptide comprising, or alternatively consisting of, a portion of the above polypeptides, such as for example, the PSGR extracellular loop I comprising, or alternatively consisting of, amino acids 77 to 98 of FIGS. 1A–B (SEQ ID NO:2); the PSGR extracellular loop II comprising, or alternatively consisting of, amino acids 163 to 197; the PSGR extracellular loop III comprising, or alternatively consisting of, amino acids 262 to 272; the PSGR intracellular loop I comprising, or alternatively consisting of, amino acids 43 to 55; the PSGR intracellular loop II comprising, or alternatively consisting of, amino acids 120 to 141; and/or the PSGR intracellular loop III comprising, or alternatively consisting of, amino acids 219 to 240 as well as polypeptides which are at least 80% identical, more preferably at least 90% or 95% identical, still more preferably at least 96%, 97%, 98%, 99% or 100% identical to the polypeptides described above (e.g., the polypeptide encoded by the cDNA in ATCC Deposit 97131, and the polypeptide of FIGS. 1A–B (SEQ ID NO:2)), and also include portions of such polypeptides with at least 30 amino acids and more preferably at least 50 or at least 100 amino acids. Polynucleotides encoding these polypeptides are also encompassed by the invention.

By a polypeptide having an amino acid sequence at least, for example, 95% "identical" to a reference amino acid sequence of a PSGR polypeptide is intended that the amino acid sequence of the polypeptide is identical to the reference sequence except that the polypeptide sequence may include up to five amino acid alterations per each 100 amino acids of the reference amino acid of PSGR. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98%, or 99% identical to, for instance, the amino acid sequence shown in FIGS. 1A–B (SEQ ID NO:2), or to the amino acid sequence encoded by the cDNA in ATCC Deposit 97131, can be determined conventionally using known computer programs such the Bestfit program (Wisconsin Sequence Analysis Package, Version 8 for Unix, Genetics Computer Group, University Research Park, 575 Science Drive, Madison, Wis. 5371). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (*Comp. App. Biosci.* 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty= 0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N-and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present application is also directed to proteins cotaining polypeptides at least 90%, 95%, 96%, 97%, 98% or 99% identical to the PSGR polypeptide sequence set forth as $n^1$-$m^1$ herein. In preferred embodiments, the application is directed to proteins containing polypeptides at least 90%, 95%, 96%, 97%, 98% or 99% identical to polypeptides having the amino acid sequence of the specific PSGR N- and C-terminal deletions recited herein. Polynucleotides encoding these polypeptides are also encompassed by the invention.

In certain preferred embodiments, PSGR proteins of the invention comprise fusion proteins as described above wherein the PSGR polypeptides are those described as $n^1$-$m^1$, herein. In preferred embodiments, the application is directed to nucleic acid molecules at least 90%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross- reactivity with other antigens. Antigenic epitopes need not necessarily be immunogenic.

Fragments which function as epitopes may be produced by any conventional means. (See, e.g., Houghten, Proc. Natl. Acad. Sci. USA 82:513–5135 (1985), further described in U.S. Pat. No. 4,631,211).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, J. G. Sutcliffe et al., "Antibodies That React With Predetermined Sites on Proteins," *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful, for example, to raise antibodies, including monoclonal antibodies, that bind specifically to a polypeptide of the invention. See, for instance, Wilson et al., *Cell* 37:767–778 (1984) at 777. Antigenic epitope-bearing peptides and polypeptides of the invention preferably contain a sequence of at least seven, more preferably at least nine, at least 20, at least 25, at least 30, at least 40, at least 50 and most preferably between at least about 55 to about 100 amino acids contained within the amino acid sequence of a polypeptide of the invention. Non-limiting examples of antigenic polypeptides or peptides that can be used to generate PSGR-specific antibodies include: a polypeptide comprising or alternatively consisting of amino acid residues from about 50 to about 55 in FIGS. 1A–B (SEQ ID NO:2); a polypeptide comprising or alternatively consisting of amino acid residues from about 87 to about 90 in FIGS. 1A–B (SEQ ID NO:2); a polypeptide comprising or alternatively consisting of amino acid residues from about 227 to about 234 in FIGS. 1A–B (SEQ ID NO:2); a polypeptide comprising or alternatively consisting of amino acid residues from about 309 to about 313 in FIGS. 1A–B (SEQ ID NO:2). As indicated above, the inventors have determined that the above polypeptide fragments are antigenic regions of the PSGR protein. Polynucleotides encoding theses polypeptides are also encompassed by the invention.

The epitope-bearing peptides and polypeptides of the invention may be produced by any conventional means. R. A. Houghten, "General Method for the Rapid Solid-phase Synthesis of Large Numbers of Peptides: Specificity of Antigen-Antibody Interaction at the Level of Individual Amino Acids," *Proc. Natl. Acad. Sci. USA* 82:5131–5135 (1985). This "Simultaneous Multiple Peptide Synthesis (SMPS)" process is further described in U.S. Pat. No. 4,631,211 to Houghten et al. (1986).

As one of skill in the art will appreciate, PSGR polypeptides of the present invention and the epitope-bearing fragments thereof, described herein (e.g., including, but not limited to, a portion of one, two, or all three of the the extracellular loops, such as, for example, amino acid residues 77 to 98, 163 to 197, or 262 to 272 of SEQ ID NO:2; or a portion of one, two, or all three of the intracellular loops, such as for example, amino acid residues 43 to 55, 120 to 141, or 219 to 240 of SEQ ID NO:2), can be combined with heterologous polypeptide sequences, for example, the polypeptides of the present invention may be fused with the constant domain of immunoglobulins (IgA, IgE, IgG, IgM) or portions thereof (CH1, CH2, CH3, and any combination thereof, including both entire domains and portions thereof), or albumin (including, but not limited to, recombinant albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric PSGR protein or protein fragment alone (Fountoulakis et al., *J. Biochem.* 270:3958–3964 (1995)).

Preferred Fc fusions of the present invention include, but are not limited to constructs comprising, or alternatively consisting of, amino acid residues 1 to 98, 1 to 197, 1 to 272, 22 to 320, 77 to 320, 163 to 320, 262 to 320, 77 to 272, 77 to 197, and/or 22 to 98 of SEQ ID NO:2.

The polypeptides of the present invention have uses which include, but are not limited to, as sources for generating antibodies that bind the polypeptides of the invention, and as molecular weight markers on SDS-PAGE gels or on molecular sieve gel filtration columns using methods well known to those of skill in the art.

Diagnostic Assays

The compounds of the present invention are useful for diagnosis or treatment of various prostate related disorders in mammals, preferably humans. Such disorders include but are not limited to including inflammatory disorders, such as chronic prostatitis, granulomatous prostatitis and malacoplakia, prostatic hyperplasia and prostate neoplastic disorders, including adenocarcinoma, transitional cell carcinomas, ductal carcinomas, squamous cell carcinomas, or as hormones or factors with systemic or reproductive functions.

PSGR is expressed in prostate, predominantly in the epithelial cells of gland, with an increased expression level in prostate cancer. For a number of prostate-related disorders, substantially altered (increased or decreased) levels of PSGR gene expression can be detected in prostate tissue or other cells or bodily fluids (e.g., sera, plasma, urine, semen, synovial fluid or spinal fluid) taken from an individual having such a disorder, relative to a "standard" PSGR gene expression level, that is, the PSGR expression level in prostate tissues or bodily fluids from an individual not having the prostate disorder. Thus, the invention provides a diagnostic method useful during diagnosis of an system disorder, which involves measuring the expression level of the gene encoding the PSGR polypeptide in prostate tissue or other cells or body fluid from an individual and comparing the measured gene expression level with a standard PSGR gene expression level, whereby an increase or decrease in the gene expression level(s) compared to the standard is indicative of an prostate disorder.

In particular, it is believed that certain tissues in mammals with cancer of cells or tissue of the prostate express significantly enhanced or reduced levels of normal or altered PSGR polypeptide and MRNA encoding the PSGR polypeptide when compared to a corresponding "standard" level. Further, it is believed that enhanced or depressed levels of the PSGR polypeptide can be detected in certain body fluids (e.g., sera, plasma, urine, and spinal fluid) or cells or tissue from mammals with such a cancer when compared to sera from mammals of the same species not having the cancer.

For example, as disclosed herein, PSGR polypeptides of the invention are expressed in prostate. Accordingly, polynucleotides of the invention (e.g., polynucleotide sequences complementary to all or a portion of PSGR MRNA) and antibodies (and antibody fragments) directed against the polypeptides of the invention may be used to quantitate or qualitate concentrations of cells of the prostate expressing PSGR on their cell surfaces. These antibodies additionally have diagnostic applications in detecting abnormalities in the level of PSGR gene expression, or abnormalities in the structure and/or temporal, tissue, cellular, or subcellular location of PSGR. These diagnostic assays may be performed in vivo or in vitro, such as, for example, on blood samples, biopsy tissue or autopsy tissue.

Thus, the invention provides a diagnostic method useful during diagnosis of a prostate disorder, including cancers, which involves measuring the expression level of the gene encoding the PSGR polypeptide in prostate tissue or other cells or body fluid from an individual and comparing the measured gene expression level with a standard PSGR gene expression level, whereby an increase or decrease in the gene expression level compared to the standard is indicative of a prostate disorder.

Where a diagnosis of a disorder in the prostate, including diagnosis of a tumor, has already been made according to conventional methods, the present invention is useful as a prognostic indicator, whereby patients exhibiting enhanced or depressed PSGR gene expression will experience a worse clinical outcome relative to patients expressing the gene at a level nearer the standard level.

By "assaying the expression level of the gene encoding the PSGR polypeptide" is intended qualitatively or quantitatively measuring or estimating the level of the PSGR polypeptide or the level of the mRNA encoding the PSGR polypeptide in a first biological sample either directly (e.g., by determining or estimating absolute protein level or mRNA level) or relatively (e.g., by comparing to the PSGR polypeptide level or mRNA level in a second biological sample). Preferably, the PSGR polypeptide level or mRNA level in the first biological sample is measured or estimated and compared to a standard PSGR polypeptide level or MRNA level, the standard being taken from a second biological sample obtained from an individual not having the disorder or being determined by averaging levels from a population of individuals not having a disorder of the prostate. As will be appreciated in the art, once a standard PSGR polypeptide level or mRNA level is known, it can be used repeatedly as a standard for comparison.

By "biological sample" is intended any biological sample obtained from an individual, cell line, tissue culture, or other source containing PSGR protein (including portions thereof) or mRNA. As indicated, biological samples include body fluids (such as sera, plasma, urine, synovial fluid and spinal fluid) which contain soluble domains of the PSGR polypeptide, cells expressing PSGR polypeptides, prostate tissue, and other tissue sources found to express the full length or soluble domains of PSGR. Methods for obtaining tissue biopsies and body fluids from mammals are well known in the art. Where the biological sample is to include mRNA, a tissue biopsy is the preferred source.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the PSGR polypeptide are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-L CR).

The present invention also relates to diagnostic assays such as quantitative and diagnostic assays for detecting levels of PSGR protein, or the soluble form thereof, in a biological sample (e.g., cells and tissues), including determination of normal and abnormal levels of polypeptides. Thus, for instance, a diagnostic assay in accordance with the invention for detecting over-expression of PSGR compared to normal control tissue samples may be used to detect the presence of tumors, for example. Assay techniques that can be used to determine levels of a protein, such as a PSGR protein of the present invention in a sample derived from a host are well-known to those of skill in the art. Such assay methods include radioimmunoassays, competitive-binding assays, Western Blot analysis and ELISA assays. Assaying PSGR protein levels in a biological sample can occur using any art-known method.

Assaying PSGR polypeptide levels in a biological sample can occur using antibody-based techniques. For example, PSGR polypeptide expression in tissues can be studied with classical immunohistological methods (Jalkanen, M., et al., *J. Cell. Biol.* 101:976–985 (1985); Jalkanen, M., et al, *J. Cell. Biol.* 105:3087–3096 (1987)). Other antibody-based methods useful for detecting PSGR polypeptide gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

The tissue or cell type to be analyzed will generally include those which are known, or suspected, to express the PSGR gene (such as, for example, cells of the prostate or prostate cancer). The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of the PSGR gene.

For example, antibodies, or fragments of antibodies, such as those described herein, may be used to quantitatively or qualitatively detect the presence of PSGR gene products or conserved variants or peptide fragments thereof. This can be accomplished, for example, by immunofluorescence techniques employing a fluorescently labeled antibody coupled with light microscopic, flow cytometric, or fluorimetric detection.

In a preferred embodiment, antibodies, or fragments of antibodies directed to any one or all of the extracellular or intracellular domains of PSGR may be used to quantitatively or qualitatively detect the presence of PSGR gene products or conserved variants or peptide fragments thereof. This can be accomplished, for example, by immunofluorescence techniques employing a fluorescently labeled antibody coupled with light microscopic, flow cytometric, or fluorimetric detection.

In an additional preferred embodiment, antibodies, or fragments of antibodies directed to a conformational epitope of PSGR may be used to quantitatively or qualitatively detect the presence of PSGR gene products or conserved variants or peptide fragments thereof. This can be accomplished, for example, by immunofluorescence techniques employing a fluorescently labeled antibody coupled with light microscopic, flow cytometric, or fluorimetric detection.

The antibodies (or fragments thereof), and/or PSGR polypeptides of the present invention may, additionally, be employed histologically, as in immunofluorescence, immunoelectron microscopy or non-immunological assays, for in situ detection of PSGR gene products or conserved variants or peptide fragments thereof. In situ detection may be accomplished by removing a histological specimen from a patient, and applying thereto a labeled antibody or PSGR polypeptide of the present invention. The antibody (or fragment) or PSGR polypeptide is preferably applied by overlaying the labeled antibody (or fragment) onto a biological sample. Through the use of such a procedure, it is possible to determine not only the presence of the PSGR gene product, or conserved variants or peptide fragments, or PSGR polypeptide binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for PSGR gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of binding PSGR gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled anti-PSGR antibody or detectable PSGR polypeptide. The solid phase support may then be washed with the buffer a second time to remove unbound antibody or polypeptide. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-PSGR antibody or PSGR polypeptide may be determined according to well known methods. Those skilled in the art will be able to determine operative and optimal assay conditions for each determination by employing routine experimentation.

In addition to assaying PSGR polypeptide levels or polynucleotide levels in a biological sample obtained from an individual, PSGR polypeptide or polynucleotide can also be detected in vivo by imaging. For example, in one embodiment of the invention, PSGR polypeptide and/or anti-PSGR antibodies are used to image prostate neoplasms. In another embodiment, PSGR polynucleotides of the invention (e.g., polynucleotides complementary to all or a portion of PSGR MRNA) and/or anti-PSGR antibodies (e.g., antibodies directed to any one or a combination of the extracellular or intracellular domains of PSGR, antibodies directed to a conformational epitope of PSGR, antibodies directed to the full length polypeptide expressed on the cell surface of a mammalian cell) are used to image prostate neoplastic tissues.

Antibody labels or markers for in vivo imaging of PSGR polypeptide include those detectable by X-radiography, NMR, MRI, CAT-scans or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma. Where in vivo imaging is used to detect enhanced levels of PSGR polypeptide for diagnosis in humans, it may be preferable to use human antibodies or "humanized" chimeric monoclonal antibodies. Such antibodies can be produced using techniques described herein or otherwise known in the art. For example methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Additionally, any PSGR polypeptide whose presence can be detected, can be administered. For example, PSGR polypeptides labeled with a radio-opaque or other appropriate compound can be administered and visualized in vivo, as discussed, above for labeled antibodies. Further such PSGR polypeptides can be utilized for in vitro diagnostic procedures.

A PSGR polypeptide-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for a prostate disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain PSGR protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

With respect to antibodies, one of the ways in which the anti-PSGR antibody can be detectably labeled is by linking the same to an enzyme and using the linked product in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller et al., *J. Clin. Pathol.* 31:507–520 (1978); Butler, J. E., *Meth. Enzymol.* 73:482–523 (198); Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect PSGR through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by means including, but not limited to, a gamma counter, a scintillation counter, or autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, ophthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Epitopes and Antibodies

The present invention encompasses polypeptides comprising, or alternatively consisting of, an epitope of the polypeptide having an amino acid sequence of SEQ ID NO:2, or an eptiope of the polypeptide having an amino acid sequence of SEQ ID NO:4, or an epitope of the polypeptide sequence encoded by a polynucleotide sequence contained in ATCC deposit No. 97131, or encoded by a polynucleotide that hybridizes to the complement of the sequence of SEQ ID NO:1, or encoded by a polynucleotide that hybridizes to the complement of the sequence of SEQ ID NO:3, or contained in ATCC deposit No. 97131 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO: 1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,21).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl- N-hydroxysuccinimide ester (MBS), while other peptides may be coupled to carriers using a more general linking agent such as glutaraldehyde. Animals such as rabbits, rats and mice are immunized with either free or carrier- coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a PSGR polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, gG3, gG4, gA1 and IgA2) or subclass of immunoglobulin molecule. In a specific embodiment, the immunoglobulin molecules of the invention are IgG1. In another specific embodiment, the immunoglobulin molecules of the invention are IgG4.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (199); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$M, $5\times10^{-7}$ M, $10^{7}$ M, $5\times10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):198–1988 (1998); Chen et al., Cancer Res. 58(16):3668–3678 (1998); Harrop et al., J. Immunol. 16(4):1786–1794 (1998); Zhu et Cancer Res. 58(15):3209–3214 (1998); Yoon et al., J. Immunol. 160(7):3170–3179 (1998Prat et al., J. Cell. Sci. 111(Pt2):237–247 (1998); Pitard et al., J. Immunol. Methods 205(2):177–190 (1997); Liautard et al., Cytokine 9(4):233–241 (1997); Carlson et al Chem. 272(17):11295–11301 (1997); Taryman et al., Neuron 14(4):755–762 (1995); Mull et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 198) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art and as discussed in detail in the Examples (e.g., Example 5). In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:19–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:104–1043 (1988) (said references incorporated by reference in their entireties).

Examples of techniques which can be used to produce single-chain Fvs and antibodies include those described in U.S. Pat. 4,946,778 and 5,258,498; Huston et al., Methods in Enzymology 203:46–88 (199); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:19–202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489–498 (199); Studnicka et al., Protein Engineering 7(6):805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (199)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a PSGR polypeptide of the invention, preferably, an antibody that binds to a polypeptide having the amino acid sequence of SEQ ID NO:2 or SEQ ID NO:4.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio-Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, N.Y., which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervari ability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:85–855 (1984); Neuberger et al., Nature 312:604–608

(1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt- cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (198)); gpt, which confers resistance to mycophenolic acid (Mulligan & Berg, Proc. Natl. Acad. Sci. USA 78:2072 (198)); neo, which confers resistance to the aminoglycoside G-418 Clinical Pharmacy 12:488–505; Wu and Wu, Biotherapy 3:87–95 (199); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 1(5):155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, N.Y. (1993); Kriegler, Gene Transfer and Expression, A Laboratory Manual, Stockton Press, N.Y. (1990); and in Chapters 12 and 13, Dracopoli et al. (eds), Current Protocols in Human Genetics, John Wiley & Sons, N.Y. (1994); Colberre-Garapin et al., J. Mol. Biol. 150:1 (198), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide of the present invention (or portion thereof, preferably at least 10, 20, 30, 40, 50, 60, 70, 80, 90 or 100 amino acids of the polypeptide) to generate fusion proteins. The fusion does not necessarily need to be direct, but may occur through linker sequences. The antibodies may be specific for antigens other than polypeptides of the present invention (or portion thereof, preferably at least 10, 20, 30, 40, 50, 60, 70, 80, 90 or 100 amino acids of the polypeptide). For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:9–99 (1994); U.S. Pat. No. 5,474,981; Gillies et al., PNAS 89:1428–1432 (1992); Fell et al., J. Immunol. 146:2446–2452(199), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (199); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a PSGR polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 9131), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

In specific embodiments, an antibody or fragment thereof is attached to macrocyclic chelators useful for conjugating radiometal ions, including but not limited to, 177Lu, 90Y, 166Ho, and 153Sm, to polypeptides. In specific embodiments, the macrocyclic chelator is 1,4,7,10-tetraazacyclododecane-N,N',N'',N'''-tetraacetic acid (DOTA). In other specific embodiments, the DOTA is attached to the an antibody of the invention or fragment thereof via a linker molecule. Examples of linker molecules useful for conjugating DOTA to a polypeptide are commonly known in the art—see, for example, DeNardo et al., Clin Cancer Res. 4(10):2483–90, 1998; Peterson et al., Bioconjug. Chem. 10(4):553–7, 1999; and Zimmerman et al, Nucl. Med. Biol. 26(8):943–50, 1999 which are hereby incorporated by reference in their entirety.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. In a specific embodiment, the antibodies can be used diagnostically to, for example, monitor the development or progression of a prostatic neoplasm as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/3491), Fas Ligand (Takahashi et al., *Int. Immunol.*, 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Imunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell*, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1%

Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$p or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Antibodies of the invention may be characterized using Immunocytochemisty methods on cells (e.g., mammalian cells, such as CHO cells) transfected with a vector enabling the expression of PSGR or with vector alone using techniques commonly known in the art. Antibodies that bound PSGR transfected- but not vector-only tranfected, cells are PSGR specific.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

In a specific and preferred embodiment, the present invention is directed to antibody-based therapies which involve administering antibodies of the invention to an animal, preferably a mammal, and most preferably a human, patient for treating one or more of the diseases, disorders, or conditions of the prostate, including, but not limited to, inflammatory disorders, such as chronic prostatitis, granulomatous prostatitis and malacoplakia, prostatic hyperplasia; and prostate neoplastic disorders, including adenocarcinoma, transitional cell carcinomas, ductal carcinomas, squamous cell carcinomas; or as hormones or factors with systemic or reproductive functions. Therapeutic compounds of the invention include, but are not limited to, antibodies of the invention (e.g., antibodies directed to one or any combination of the extracellular and intracellular domains of PSGR; antibodies directed to the full length protein expressed on the cell surface of a mammalian cell; antibodies directed to an epitope of PSGR (such as, a linear epitope or a conformational epitope), including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions of the prostate described herein. The treatment and/or prevention of diseases, disorders, or conditions of the prostate associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and antitumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (199); Tolstoshev, Ann. Rev. Pharmacol. Toxicol. 32:573–596 (1993); Mulligan, Science 260:926–932 (1993); and Morgan and Anderson, Ann. Rev. Biochem. 62:19–217 (1993); May, TIBTECH 1(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; W092/20316; W093/14188, WO 93/2022). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (199); Rosenfeld et al., Cell 68:143–155 (1992); Mastrangeli et al., J. Clin. Invest. 91:225–234 (1993); PCT Publication WO 94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox—like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a prostate disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of a PSGR polypeptide in an animal, preferably a mammal and most preferably a human. A preferred aspect of the invention is the detection and diagnosis of a disease or disorder of the prostate associated with aberrant expression of PSGR in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a PSGR polypeptide (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against PSGR polynucleotides and polypeptides. Such a kit may include a control antibody that does not react with the polypeptide of interest. Such a kit may include a substantially isolated polypeptide antigen comprising an epitope which is specifically immunoreactive with at least one anti-PSGR antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Uses of the PSGR Polynucleotides

The PSGR polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Clone HPRAJ70 is specifically targeted to and can hybridize with 11p15. Thus, PSGR polynucleotides of the present invention can routinely be used as a chromosome marker for chromosome 11 using techniques known in the art.

Briefly, sequences can be mapped to chromosomes by preparing PCR primers (preferably 15–25 bp) from the sequences shown in SEQ ID NO:1. Primers can optionally be selected using computer analysis so that primers do not span more than one predicted exon in the genomic DNA. These primers are then used for PCR screening of somatic cell hybrids containing individual human chromosomes. Only those hybrids containing the human PSGR gene corresponding to the SEQ ID NO:1 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the PSGR polynucleotides can be achieved with panels of specific chromosome fragments. Other gene mapping strategies that can be used include in situ hybridization, prescreening with labeled flow-sorted chromosomes, preselection by hybridization to construct chromosome specific-cDNA libraries, and computer mapping techniques (See, e.g., Shuler, Trends Biotechnol 16:456–459 (1998) which is hereby incorporated by reference in its entirety).

Precise chromosomal location of the PSGR polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the PSGR polynucleotides can be used individually (to mark a single chromosome or a single site on that chromosome) or in panels (for marking multiple sites and/or multiple chromosomes).

Thus, the present invention also provides a method for chromosomal localization which involves (a) preparing PCR primers from the polynucleotide sequence in SEQ ID NO:1 and (b) screening somatic cell hybrids containing individual chromosomes.

The polynucleotides of the present invention would likewise be useful for radiation hybrid mapping, HAPPY mapping, and long range restriction mapping. For a review of these techniques and others known in the art, see, e.g., Dear, "Genome Mapping: A Practical Approach," IRL Press at Oxford University Press, London (1997); Aydin, J. Mol. Med. 77:691–694 (1999); Hacia et al., Mol. Psychiatry 3:483–492 (1998); Herrick et al., Chromosome Res. 7:409–423 (1999); Hamilton et al., Methods Cell Biol. 62:265–280 (2000); and/or Ott, J. Hered. 90:68–70 (1999) each of which is hereby incorporated by reference in its entirety.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the PSGR polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the PSGR polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using PSGR polynucleotides. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an individual and comparing the measured gene expression level with a standard level of polynucleotide expression level, whereby an increase or decrease in the gene expression level compared to the standard is indicative of a disorder.

In still another embodiment, the invention includes a kit for analyzing samples for the presence of proliferative and/or cancerous polynucleotides derived from a test subject. In a general embodiment, the kit includes at least one polynucleotide probe containing a nucleotide sequence that will specifically hybridize with a polynucleotide of the present invention and a suitable container. In a specific embodiment, the kit includes two polynucleotide probes defining an internal region of the polynucleotide of the present invention, where each probe has one strand containing a 3'mer-end internal to the region. In a further embodiment, the probes may be useful as primers for polymerase chain reaction amplification.

Where a diagnosis of a disorder, has already been made according to conventional methods, the present invention is useful as a prognostic indicator, whereby patients exhibiting enhanced or depressed polynucleotide of the present invention expression will experience a worse clinical outcome relative to patients expressing the gene at a level nearer the standard level.

By "measuring the expression level of polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of individuals not having a disorder. As will be appreciated in the art, once a standard polypeptide level or mRNA level is known, it can be used repeatedly as a standard for comparison.

By "biological sample" is intended any biological sample obtained from an individual, body fluid, cell line, tissue culture, or other source which contains the polypeptide of the present invention or mRNA. As indicated, biological samples include body fluids (such as semen, lymph, sera, plasma, urine, synovial fluid and spinal fluid) which contain the polypeptide of the present invention, and other tissue sources found to express the polypeptide of the present invention. Methods for obtaining tissue biopsies and body fluids from mammals are well known in the art. Where the biological sample is to include mRNA, a tissue biopsy is the preferred source.

The method(s) provided above may preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including cancerous diseases and conditions. Such a method is described in U.S. Pat. Nos. 5,858,659 and 5,856,104. The U.S. Patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point (T.sub.m) by 8°–20° C., vs. 4°–16° C. for the DNA/DNA 15-mer duplex. Also, the absence of charge groups in PNA means that hybridization can be done at low ionic strengths and reduce possible interference by salt during the analysis.

The present invention is useful for detecting cancer in mammals. In particular the invention is useful during diagnosis of pathological cell proliferative neoplasias which include, but are not limited to: acute myelogenous leukemias including acute monocytic leukemia, acute myeloblastic leukemia, acute promyelocytic leukemia, acute myelomonocytic leukemia, acute erythroleukemia, acute megakaryocytic leukemia, and acute undifferentiated leukemia, etc.; and chronic myelogenous leukemias including chronic myelomonocytic leukemia, chronic granulocytic leukemia, etc. Preferred mammals include monkeys, apes, cats, dogs, cows, pigs, horses, rabbits and humans. Particularly preferred are humans.

Pathological cell proliferative disorders are often associated with inappropriate activation of proto-oncogenes. (Gelmann, E. P. et al., "The Etiology of Acute Leukemia: Molecular Genetics and Viral Oncology," in Neoplastic Diseases of the Blood, Vol 1., Wiernik, P. H. et al. eds., 16–182 (1985)). Neoplasias are now believed to result from the qualitative alteration of a normal cellular gene product, or from the quantitative modification of gene expression by insertion into the chromosome of a viral sequence, by chromosomal translocation of a gene to a more actively transcribed region, or by some other mechanism. (Gelmann et al., supra) It is likely that mutated or altered expression of specific genes is involved in the pathogenesis of some leukemias, among other tissues and cell types. (Gelmann et al., supra) Indeed, the human counterparts of the oncogenes involved in some animal neoplasias have been amplified or translocated in some cases of human leukemia and carcinoma. (Gelmann et al., supra)

For example, c-myc expression is highly amplified in the non-lymphocytic leukemia cell line HL-60. When HL-60 cells are chemically induced to stop proliferation, the level of c-myc is found to be downregulated. (International Publication Number WO 91/15580) However, it has been shown that exposure of HL-60 cells to a DNA construct that is complementary to the 5' end of c-myc or c-myb blocks translation of the corresponding mRNAs which downregulates expression of the c-myc or c-myb proteins and causes arrest of cell proliferation and differentiation of the treated cells. (International Publication Number WO 91/15580; Wickstrom et al., Proc. Natl. Acad. Sci. 85:1028 (1988); Anfossi et al., Proc. Natl. Acad. Sci. 86:3379 (1989)). However, the skilled artisan would appreciate the present invention's usefulness would not be limited to treatment of proliferative diseases, disorders, and/or conditions of hematopoietic cells and tissues, in light of the numerous cells and cell types of varying origins which are known to exhibit proliferative phenotypes.

In addition to the foregoing, a PSGR polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression,CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991) ) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

PSGR polynucleotides are also useful in gene therapy. One goal of gene therapy is to insert a normal gene into an organism having a defective gene, in an effort to correct the genetic defect. PSGR offers a means of targeting such genetic defects in a highly accurate manner. Another goal is to insert a new gene that was not present in the host genome, thereby producing a new trait in the host cell.

The PSGR polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The PSGR polynucleotides can be used as additional DNA markers for RFLP.

The PSGR polynucleotides can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once a unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., urine, semen, blood, saliva, synovial fluid, amniotic fluid, breast milk, lymph, pulmonary sputum or surfactant, fecal matter, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, PSGR polynucleotides can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from PSGR sequences. Panels of such reagents can identify tissue by species and/or by organ type. In a similar fashion, these reagents can be used to screen tissue cultures for contamination.

Because PSGR is found expressed in prostate, PSGR polynucleotides are useful as hybridization probes for differential identification of the tissue(s) or cell type(s) present in a biological sample. Similarly, polypeptides and antibodies directed to PSGR polypeptides are useful to provide immunological probes for differential identification of the tissue(s) or cell type(s). In addition, for a number of diseases, disorders, and/or conditions of the above tissues or cells, particularly of the reproductive system, significantly higher or lower levels of PSGR gene expression may be detected in certain tissues (e.g., prostate, cancerous and wounded tissues) or bodily fluids (e.g., urine, semen, serum, plasma, synovial fluid or spinal fluid) taken from an individual having such a disorder, relative to a "standard" PSGR gene expression level, i.e., the PSGR expression level in healthy tissue from an individual not having the reproductive system disorder.

Thus, the invention provides a diagnostic method of a disorder, which involves: (a) assaying PSGR gene expression level in cells or body fluid of an individual; (b) comparing the PSGR gene expression level with a standard PSGR gene expression level, whereby an increase or decrease in the assayed PSGR gene expression level compared to the standard expression level is indicative of disorder in the reproductive system.

In a preferred embodiment, the invention provides a diagnostic method of a disorder, which involves: (a) assaying PSGR gene expression level in prostate cells or body fluid of an individual (e.g., blood, urine, semen); (b) comparing the PSGR gene expression level with a standard PSGR gene expression level, whereby an increase or decrease in the assayed PSGR gene expression level compared to the standard expression level is indicative of disorder in the reproductive system, particularly, indicative of a disorder of the prostate, including but not limited to prostate cancer.

In the very least, the PSGR polynucleotides can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of PSGR Polypeptides

PSGR polypeptides can be used in numerous ways. The following description should be considered exemplary and utilizes known techniques.

Polypeptides and antibodies directed to polypeptides of the present invention are useful to provide immunological probes for differential identification of the tissue(s) (e.g., immunohistochemistry assays such as, for example, ABC immunoperoxidase (Hsu et al., J. Histochem. Cytochem. 29:577–580 (1981)) or cell type(s) (e.g., immunocytochemistry assays).

Antibodies can be used to assay levels of polypeptides encoded by polynucleotides of the invention in a biological sample using classical immunohistological methods known to those of skill in the art (Jalkanen, M., et al., J. Cell. Biol. 101:976–985 (1985); Jalkanen, M., et al., J. Cell . Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminescent labels, such as luminol; and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, $^{131}$I, $^{112}$In, $^{99m}$Tc, ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F, $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru), a radioopaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

In one embodiment, the invention provides a method for the specific delivery of compositions of the invention to cells by administering polypeptides of the invention (e.g., polypeptides encoded by polynucleotides of the invention and/or antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells, such as prostate neoplasms) by administering polypeptides of the invention (e.g., polypeptides encoded by polynucleotides of the invention and/or antibodies) in association with toxins or cytotoxic prodrugs.

In a preferred embodiment, the invention provides a method for the specific destruction of prostate cells (e.g., aberrant prostate cells, prostate neoplasm) by administering polypeptides of the invention (e.g., polypeptides encoded by polynucleotides of the invention and/or antibodies) in association with toxins or cytotoxic prodrugs.

By "toxin" is meant one or more compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{111}$In $^{68}$Ge, $^{57}$Co, $^{65}$Zn, $^{85}$Sr, $^{32}$P, $^{35}$S $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin.

In a specific embodiment, the invention provides a method for the specific destruction of cells (e.g., the destruction of tumor cells) by administering polypeptides of the invention or antibodies of the invention in association with radioisotopes $^{90}$Y, $^{111}$In and/or $^{131}$I.

Techniques known in the art may be applied to label polypeptides of the invention (including antibodies). Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

Thus, the invention provides a diagnostic method of a disorder, which involves (a) assaying the expression of PSGR polypeptide in cells or body fluid of an individual; (b) comparing the level of gene expression with a standard gene expression level, whereby an increase or decrease in the assayed PSGR polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, PSGR polypeptides can be used to treat, prevent, and/or diagnose disease or conditions of the prostate such as, for example, inflammatory disorders, such as chronic prostatitis, granulomatous prostatitis and malacoplakia, prostatic hyperplasia and prostate neoplastic disorders, including adenocarcinoma, transitional cell carcinomas, ductal carcinomas, squamous cell carcinomas, or as hormones or factors with systemic or reproductive functions. For example, patients can be administered PSGR polypeptides in an effort to replace absent or decreased levels of the PSGR polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor supressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to PSGR polypeptides can also be used to treat, prevent, and/or diagnose disease. For example, administration of an antibody directed to a PSGR polypeptide can bind and reduce overproduction of the polypeptide. Similarly, administration of an antibody can activate the polypeptide, such as by binding to a polypeptide bound to a membrane (receptor).

At the very least, the PSGR polypeptides can be used as molecular weight markers on SDS-PAGE gels or on molecular sieve gel filtration columns using methods well known to those of skill in the art. PSGR polypeptides can also be used to raise antibodies, which in turn are used to measure protein expression from a recombinant cell, as a way of assessing transformation of the host cell. Moreover, PSGR polypeptides can be used to test the following biological activities.

Methods for Detecting Cancer

In general, a cancer may be detected in a patient based on the presence of one or more PSGR proteins and/or polynucleotides encoding such proteins in a biological sample (for example, blood, sera, urine, and/or tumor biopsies) obtained from the patient. In other words, such proteins may be used as markers to indicate the presence or absence of a cancer such as prostate cancer. In addition, such proteins may be useful for the detection of other cancers. The binding agents provided herin generally permit detection of the level of antigen that binds to the agent in the biological sample. Polynucleotide primers and probes may be used to detect the level of mRNA encoding PSGR, which is also indicative of the presence or absence of a cancer. In general, PSGR should be present at a level that is at least three fold higher in tumor tissue than in normal tissue.

There are a variety of assay formats known to those of ordinary skill in the art for using a binding agent to detect polypeptide markers in a sample. See, e.g., Harlow and Lane, supra. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include PSGR and portions thereof to which the binding agent binds, as described above.

The solid support may be any material known to those of skill in the art to which PSGR may be attached. For example, the solid support may be a test well in a microtiter plate or a nitrocellulose or other suitable membrane. Alternatively, the support may be a bead or disc, such as glass fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply descibed in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for the suitable amount of time. The contact time varies with temperature, but is typically between about 1 hour and about 1 day. In general, contacting a well of plastic microtiter plate (such as polystyrene or polyvinylchloride) with an amount of binding agent ranging from about 10 ng to about 10 ug, and preferably about 100 ng to about 1 ug, is sufficient to immobilize an adequate amount of binding agent.

Covalent attachment of binding agent to a solid suport may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of the PSGR polypeptide of the present invention. This method requires a polynucleotide which codes for a PSGR polypeptide operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a PSGR polynucleotide ex vivo, with the engineered cells then being provided to a patient to be treated with the polypeptide. Such methods are well-known in the art. For example, see Belldegrun, A., et al., J. Natl. Cancer Inst. 85: 207–216 (1993); Ferrantini, M. et al., Cancer Research 53: 1107–1112 (1993); Ferrantini, M. et al., J. Immunology 153: 4604–4615 (1994); Kaido, T., et al., Int. J. Cancer 60: 22–229 (1995); Ogura, H., et al., Cancer Research 50: 5102–5106 (1990); Santodonato, L., et al., Human Gene Therapy 7:1–10 (1996); Santodonato, L., et al., Gene Therapy 4:1246–1255 (1997); and Zhang, J.-F. et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the PSGR polynucleotide constructs can be delivered by any method that delivers injectable materials to the cells of an animal, such as, injection into the interstitial space of tissues (heart, muscle, skin, lung, liver, and the like). The PSGR polynucleotide constructs may be delivered in a pharmaceutically acceptable liquid or aqueous carrier.

In one embodiment, the PSGR polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the PSGR polynucleotides can also be delivered in liposome formulations and lipofectin formulations and the like can be prepared by methods well known to those skilled in the art. Such methods are described, for example, in U.S. Pat. Nos. 5,593,972, 5,589, 466, and 5,580,859, which are herein incorporated by reference.

The PSGR polynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1V5, pcDNA3.1, and pRc/CMV2 available from Invitrogen. Other suitable vectors will be readily apparent to the skilled artisan.

Any strong promoter known to those skilled in the art can be used for driving the expression of PSGR polynucleotide sequence. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for PSGR.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The PSGR polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked PSGR DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the PSGR polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA (1987) 84:7413–7416, which is herein incorporated by reference); mRNA (Malone et al., Proc. Natl. Acad. Sci. USA (1989) 86:6077–6081, which is herein incorporated by reference); and purified transcription factors (Debs et al., J. Biol. Chem. (1990) 265:10189–10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl Acad. Sci. USA (1987) 84:7413–7416, which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Felgner et al., Proc. Natl. Acad. Sci. USA 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology (1983), 101:512–527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta (1975) 394:483; Wilson et al., Cell (1979) 17:77); ether injection (Deamer, D. and Bangham, A., Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); detergent dialysis (Enoch, H. and Strittmatter, P., Proc. Natl. Acad. Sci. USA (1979) 76:145); and reverse-phase evaporation (REV) (Fraley et al., J. Biol. Chem. (1980) 255:10431; Szoka, F. and Papahadjopoulos, D., Proc. Natl. Acad. Sci. USA (1978) 75:145; Schaefer-Ridder et al., Science (1982) 215:166), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding PSGR. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding PSGR. Such retroviral vector particles then may be employed, to transduce eukaryotic cells, either in vitro or in vivo. The transduced eukaryotic cells will express PSGR.

In certain other embodiments, cells are engineered, ex vivo or in vivo, with PSGR polynucleotide contained in an adenovirus vector. Adenovirus can be manipulated such that it encodes and expresses PSGR, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) Am. Rev. Respir. Dis.109:233–238). Finally, adenovirus mediated gene transfer has been demonstrated in a number of instances including transfer of alpha-1-antitrypsin and CFTR to the lungs of cotton rats (Rosenfeld, M. A. et al. (1991) Science 252:43–434; Rosenfeld et al., (1992) Cell 68:143–155). Furthermore, extensive studies to attempt to establish adenovirus as a causative agent in human cancer were uniformly negative (Green, M. et al. (1979) Proc. Natl. Acad. Sci. USA 76:6606).

Suitable adenoviral vectors useful in the present invention are described, for example, in Kozarsky and Wilson, Curr. Opin. Genet. Devel. 3:499–503 (1993); Rosenfeld et al., Cell 68:143–155 (1992); Engelhardt et al., Human Genet. Ther. 4:759–769 (1993); Yang et al., Nature Genet. 7:362–369 (1994); Wilson et al., Nature 365:69–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express Ela and Elb, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., Curr. Topics in Microbiol. Immunol. 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The PSGR polynucleotide construct is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the PSGR polynucleotide construct. These viral particles are then used to transduce eukaryotic cells, either ex vivo or in vivo. The transduced cells will contain the PSGR polynucleotide construct integrated into its genome, and will express PSGR.

Another method of gene therapy involves operably associating heterologous control regions and endogenous polynucleotide sequences (e.g. encoding PSGR) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the PSGR desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous PSGR sequence is placed under the control of the promoter. The promoter then drives the expression of the endogenous PSGR sequence.

The polynucleotides encoding PSGR may be administered along with other polynucleotides encoding an angiogenic protein. Examples of angiogenic proteins include, but are not limited to, acidic and basic fibroblast growth factors, VEGF-1, VEGF-2, VEGF-3, epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding PSGR contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., Science 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189:11277–11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities of PSGR

PSGR polynucleotides or polypeptides, or agonists or antagonists of PSGR, can be used in assays to test for one or more biological activities. If PSGR polynucleotides or polypeptides, or agonists or antagonists of PSGR, do exhibit activity in a particular assay, it is likely that PSGR may be involved in the diseases associated with the biological activity. Therefore, PSGR could be used to treat, prevent, and/or diagnose the associated disease.

PSGR is a member of the seven transmembrane G-protein coupled odorant receptor gene family which demonstrates prostatic epithelial cell resticted expression with tumor cells exhibiting significantly increased expression.

Thus, PSGR may be useful as a therapeutic molecule. It would be useful for diagnosis, detection, treatment and/or prevention of diseases or disorders of the prostate, including inflammatory disorders, such as chronic prostatitis, granulomatous prostatitis and malacoplakia, prostatic hyperplasia and prostate neoplastic disorders, including adenocarcinoma, transitional cell carcinomas, ductal carcinomas, squamous cell carcinomas, or as hormones or factors with systemic or reproductive functions. Particularly, PSGR may be a useful therapeutic for prostate cancer. Treatment, diagnosis, detection, and/or prevention of prostate disorders could be carried out using a soluble form of PSGR, the PSGR ligand, gene therapy, or ex vivo applications. Moreover, inhibitors of PSGR, either blocking antibodies or mutant forms, could modulate the expression of PSGR. These inhibitors may be useful to treat, diagnose, detect, and/or prevent diseases associated with the misregulation of PSGR.

In one embodiment, the invention provides a method for the specific delivery of compositions of the invention to cells (e.g., prostate or prostate cancer cells) by administering polypeptides of the invention (e.g., PSGR polypeptides or anti-PSGR antibodies) that are associated with heterologous polypeptides or nucleic acids. In one example, the invention provides a method for delivering a therapeutic protein into the targeted cell (e.g., a prostate cancer cell). In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., PSGR polypeptides or anti-PSGR antibodies) in association with toxins or cytotoxic prodrugs.

By "toxin" is meant compounds that bind and activate endogenous cytotoxic effector systems, radioisotopes, holotoxins, modified toxins, catalytic subunits of toxins, cytotoxins (cytotoxic agents), or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{153}$Gd, luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

It will be appreciated that conditions caused by a decrease in the standard or normal level of PSGR activity in an individual, particularly disorders of the prostate, can be treated by administration of PSGR polypeptide (e.g., in the form of soluble extracellular domain or cells expressing the complete protein) or agonist. Thus, the invention also provides a method of treatment of an individual in need of an increased level of PSGR activity comprising administering to such an individual a pharmaceutical composition comprising an amount of an isolated PSGR polypeptide of the invention, or agonist thereof (e.g, an agonistic PSGR antibody), effective to increase the PSGR activity level in such an individual.

It will also be appreciated that conditions caused by a increase in the standard or normal level of PSGR activity in an individual, particularly disorders of the prostate, can be treated by administration of PSGR polypeptides (e.g., in the form of soluble extracellular domain or cells expressing the complete protein) or antagonist (e.g., an antagonistic PSGR antibody). Thus, the invention also provides a method of treatment of an individual in need of an dereased level of PSGR activity comprising administering to such an individual a pharmaceutical composition comprising an amount of an isolated PSGR polypeptide of the invention, or antagonist thereof, effective to decrease the PSGR activity level in such an individual.

Immune Activity

PSGR polynucleotides or polypeptides, or agonists or antagonists of PSGR, may be useful in treating diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, PSGR polynucleotides or polypeptides, or agonists or antagonists of PSGR, can be used as a marker or detector of a particular immune system disease or disorder.

PSGR polynucleotides or polypeptides, or agonists or antagonists of PSGR, may be useful in treating, preventing, and/or diagnosing diseases, disorders, and/or conditions of hematopoietic cells. PSGR polynucleotides or polypeptides, or agonists or antagonists of PSGR, could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, PSGR polynucleotides or polypeptides, or agonists or antagonists of PSGR, can also be used to modulate hemostatic (the stopping of bleeding) or thrombolytic activity (clot formation). For example, by increasing hemostatic or thrombolytic activity, PSGR polynucleotides or polypeptides, or agonists or antagonists of PSGR, could be used to treat or prevent blood coagulation diseases, disorders, and/or conditions (e.g., afibrinogenemia, factor deficiencies), blood platelet diseases, disorders, and/or conditions (e.g. thrombocytopenia), or wounds resulting from trauma, surgery, or other causes. Alternatively, PSGR polynucleotides or polypeptides, or agonists or antagonists of PSGR, that can decrease hemostatic or thrombolytic activity could be used to inhibit or dissolve clotting. These molecules could be important in the treatment or prevention of heart attacks (infarction), strokes, or scarring.

PSGR polynucleotides or polypeptides, or agonists or antagonists of PSGR, may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of PSGR polynucleotides or polypeptides, or agonists or antagonists of PSGR, that can inhibit an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by PSGR include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by PSGR polynucleotides or polypeptides, or agonists or antagonists of PSGR. Moreover, these molecules can be used to treat anaphylaxis, hypersensitivity to an antigenic molecule, or blood group incompatibility.

PSGR polynucleotides or polypeptides, or agonists or antagonists of PSGR, may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of PSGR polynucleotides or polypeptides, or agonists or antagonists of PSGR, that inhibits an immune response, particularly the proliferation, differentiation, or chemotaxis of T-cells, may be an effective therapy in preventing organ rejection or GVHD.

Similarly, PSGR polynucleotides or polypeptides, or agonists or antagonists of PSGR, may also be used to modulate inflammation. For example, PSGR polynucleotides or polypeptides, or agonists or antagonists of PSGR, may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

PSGR polynucleotides or polypeptides, or agonists or antagonists of PSGR, can be used to treat, prevent, and/or diagnose hyperproliferative diseases, disorders, and/or conditions, including neoplasms.

In a specific embodiment, PSGR polynucleotides or polypeptides, or agonists or antagonists of PSGR, can be used to treat, prevent, and/or diagnose hyperproliferative diseases, disorders, and/or conditions of the prostate.

In a preferred embodiment, PSGR polynucleotides or polypeptides, or agonists or antagonists of PSGR, can be used to treat, prevent, and/or diagnose prostate neoplasms.

PSGR polynucleotides or polypeptides, or agonists or antagonists of PSGR, may inhibit the proliferation of the disorder through direct or indirect interactions. Alternatively, PSGR polynucleotides or polypeptides, or agonists or antagonists of PSGR, may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by PSGR polynucleotides or polypeptides, or agonists or antagonists of PSGR, include, but are not limited to neoplasms located in the: prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by PSGR polynucleotides or polypeptides, or agonists or antagonists of PSGR. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating cell proliferative diseases, disorders, and/or conditions by inserting into an abnormally proliferating cell a polynucleotide of the present invention, wherein said polynucleotide represses said expression.

Another embodiment of the present invention provides a method of treating cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the poynucleotides of the present invention is inserted into cells to be treated utilizing a retrovirus, or more preferrably an adenoviral vector (see, e.g., G J. Nabel, et. al., PNAS 96: 324–326 (1999), which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e., magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e., to increase, decrease, or inhibit expression of the present invention) based upon said external stimulus.

Polynucleotides of the present invention may be useful in repressing expression of oncogenic genes or antigens. By "repressing expression of the oncogenic genes " is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g., as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragements thereof, of the present invention. Such antibodies, fragments, or regions, will preferably have an affinity for polynucleotides or polypeptides, including fragments thereof. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5-10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Moreover, polypeptides of the present invention are useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (see, e.g., Joseph I B, et al. J Natl Cancer Inst, 90(2):1648–53 (1998), which is hereby incorporated by reference). Antibodies directed to polypeptides or polynucleotides of the present invention may also result in inhibition of angiogenesis directly, or indirectly (see, e.g., Witte L, et al., Cancer Metastasis Rev. 17(2):155–61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (see, e.g., Schulze-Osthoff K, et.al., Eur J Biochem 254(3):439–59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuviants, such as apoptonin, galectins, thioredoxins, anti-inflammatory proteins (See for example, Mutat Res 400 (1–2):447–55 (1998), Med Hypotheses.50(5):423–33 (1998), Chem Biol Interact. Apr 24;111–112:23–34 (1998), J Mol Med.76(6):402–12 (1998), Int J Tissue React;20(1):3–15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewere herein, or indirectly, such as activating the expression of proteins known to inhibit metastasis, for example alpha 4 integrins, (See, e.g., Curr Top Microbiol Immunol 1998;231:125–41, which is hereby incorporated by reference). Such thereapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodes associated with heterologous polypeptides, heterologous nucleic acids, toxins, or prodrugs) to targeted cells expressing the polypeptide of the present invention. Polypeptides or polypeptide antibodes of the invention may be associated with with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

PSGR polynucleotides or polypeptides, or agonists or antagonists of PSGR, encoding PSGR may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

PSGR polynucleotides or polypeptides, or agonists or antagonists of PSGR, are especially effective for the treatment of critical limb ischemia and coronary disease. PSGR polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. PSGR polypeptides may be administered as part of a Therapeutic, described in more detail below. Methods of delivering PSGR polynucleotides are described in more detail herein.

Anti-Angiogenesis Activity

The naturally occurring balance between endogenous stimulators and inhibitors of angiogenesis is one in which inhibitory influences predominate. Rastinejad et al., *Cell* 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye diseases, disorders, and/or conditions, and psoriasis. See, e.g., reviews by Moses et al., *Biotech.* 9:630–634 (1991); Folkman et al., *N. Engl. J. Med.*, 333:1757–1763 (1995); Auerbach et al., *J. Microvasc. Res.* 29:40–411 (1985); Folkman, Advances in Cancer Research, eds. Klein and Weinhouse, Academic Press, New York, pp. 175–203 (1985); Patz, *Am. J. Opthalmol.* 94:715–743 (1982); and Folkman et al., Science 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment of diseases, disorders, and/or conditions associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)).Thus, the present invention provides a method of treating an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treat or prevent a cancer or tumor. Cancers which may be treated with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat or prevent cancers such as skin cancer, head and neck tumors, breast tumors, and Kaposi's sarcoma.

Within yet other aspects, polynucleotides, polypeptides, antagonists and/or agonists may be utilized to treat, prevent, and/or diagnose superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating other diseases, disorders, and/or conditions, besides cancers, which involve angiogenesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., bums), and is preferably initiated after the proliferative phase has had time to progress (approximately 14 days after the initial injury), but before hypertrophic scar or keloid development. As noted above, the present invention also provides methods for treating neovascular diseases of the eye, including for example, corneal neovascularization, neovascular glaucoma, proliferative diabetic retinopathy, retrolental fibroplasia and macular degeneration.

Moreover, Ocular diseases, disorders, and/or conditions associated with neovascularization which can be treated with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:29–312 (1978).

Thus, within one aspect of the present invention methods are provided for treating neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of diseases, disorders, and/or conditions can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a mucoadhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself.

Within another aspect of the present invention, methods are provided for treating neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat or prevent early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, diseases, disorders, and/or conditions which can be treated with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, diseases, disorders, and/or conditions and/or states, which can be treated with be treated with the the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (Helicobacter pylori), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22–26, 199); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:1732–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem. 262(4):1659–1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312–316, 1992); Thalidomide; Angostatic steroid; AGM-1470; carboxynaminolmidazole; and metalloproteinase inhibitors such as BB94.

Diseases at the Cellular Level

Diseases associated with increased cell survival or the inhibition of apoptosis that could be treated, prevented, and/or diagnosed by PSGR polynucleotides or polypeptides, as well as antagonists or agonists of PSGR, include cancers (such as prostate cancer, follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, PSGR polynucleotides, polypeptides, and/or antagonists of the invention are used to inhibit growth, progression, and/or metasis of cancers, in particular those listed above.

Additional diseases or conditions associated with increased cell survival that could be treated, prevented, and/or diagnosed by PSGR polynucleotides or polypeptides, or agonists or antagonists of PSGR, include, but are not limited to, progression, and/or metastases of malignancies and related diseases, disorders, and/or conditions such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by PSGR polynucleotides or polypeptides, as well as agonists or antagonists of PSGR, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing PSGR polynucleotides or polypeptides, as well as agonists or antagonists of PSGR, for therapeutic purposes, for example, to stimulate epithelial cell proliferation and basal keratinocytes for the purpose of wound healing, and to stimulate hair follicle production and healing of dermal wounds. PSGR polynucleotides or polypeptides, as well as agonists or antagonists of PSGR, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. PSGR polynucleotides or polypeptides, as well as agonists or antagonists of PSGR, could be used to promote dermal reestablishment subsequent to dermal loss PSGR polynucleotides or polypeptides, as well as agonists or antagonists of PSGR, could be used to increase the adherence of skin grafts to a wound bed and to stimulate re-epithelialization from the wound bed. The following are types of grafts that PSGR polynucleotides or polypeptides, agonists or antagonists of PSGR, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. PSGR polynucleotides or polypeptides, as well as agonists or antagonists of PSGR, can be used to promote skin strength and to improve the appearance of aged skin.

It is believed that PSGR polynucleotides or polypeptides, as well as agonists or antagonists of PSGR, will also produce changes in hepatocyte proliferation, and epithelial cell proliferation in the lung, breast, pancreas, stomach, small intesting, and large intestine. PSGR polynucleotides or polypeptides, as well as agonists or antagonists of PSGR, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. PSGR polynucleotides or polypeptides, agonists or antagonists of PSGR, may promote proliferation of endothelial cells, keratinocytes, and basal keratinocytes.

PSGR polynucleotides or polypeptides, as well as agonists or antagonists of PSGR, could also be used to reduce the side effects of gut toxicity that result from radiation, chemotherapy treatments or viral infections. PSGR polynucleotides or polypeptides, as well as agonists or antagonists of PSGR, may have a cytoprotective effect on the small intestine mucosa. PSGR polynucleotides or polypeptides, as well as agonists or antagonists of PSGR, may also stimulate healing of mucositis (mouth ulcers) that result from chemotherapy and viral infections.

PSGR polynucleotides or polypeptides, as well as agonists or antagonists of PSGR, could further be used in full regeneration of skin in full and partial thickness skin defects, including bums, (i.e., repopulation of hair follicles, sweat glands, and sebaceous glands), treatment of other skin defects such as psoriasis. PSGR polynucleotides or polypeptides, as well as agonists or antagonists of PSGR, could be used to treat, prevent, and/or diagnose epidermolysis bullosa, a defect in adherence of the epidermis to the underlying dermis which results in frequent, open and painful blisters by accelerating reepithelialization of these lesions. PSGR polynucleotides or polypeptides, as well as agonists or antagonists of PSGR, could also be used to treat, prevent, and/or diagnose gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, PSGR polynucleotides or polypeptides, as well as agonists or antagonists of PSGR, could be used to promote the resurfacing of the mucosal surface to aid more rapid healing and to prevent progression of inflammatory bowel disease. Treatment with PSGR polynucleotides or polypeptides, agonists or antagonists of PSGR, is expected to have a significant effect on the production of mucus throughout the gastrointestinal tract and could be used to protect the intestinal mucosa from injurious substances that are ingested or following surgery. PSGR polynucleotides or polypeptides, as well as agonists or antagonists of PSGR, could be used to treat, prevent, and/or diagnose diseases associate with the under expression of PSGR.

Moreover, PSGR polynucleotides or polypeptides, as well as agonists or antagonists of PSGR, could be used to prevent and heal damage to the lungs due to various pathological states. A growth factor such as PSGR polynucleotides or polypeptides, as well as agonists or antagonists of PSGR, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and bums, that cause necrosis of the bronchiolar epithelium and alveoli could be effectively treated using PSGR polynucleotides or polypeptides, agonists or antagonists of PSGR. Also, PSGR polynucleotides or polypeptides, as well as agonists or antagonists of PSGR, could be used to stimulate the proliferation of and differentiation of type II pneumocytes, which may help treat, prevent, and/or diagnose disease such as hyaline membrane diseases, such as infant respiratory distress syndrome and bronchopulmonary displasia, in premature infants.

PSGR polynucleotides or polypeptides, as well as agonists or antagonists of PSGR, could stimulate the proliferation and differentiation of hepatocytes and, thus, could be used to alleviate or treat, prevent, and/or diagnose liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, PSGR polynucleotides or polypeptides, as well as agonists or antagonists of PSGR, could be used treat, prevent, and/or diagnose the onset of diabetes mellitus. In patients with newly diagnosed Types I and II diabetes, where some islet cell function remains, PSGR polynucleotides or polypeptides, as well as agonists or antagonists of PSGR, could be used to maintain the islet function so as to alleviate, delay or prevent permanent manifestation of the disease. Also, PSGR polynucleotides or polypeptides, as well as agonists or antagonists of PSGR, could be used as an auxiliary in islet cell transplantation to improve or promote islet cell function.

Neurological Diseases

Nervous system diseases, disorders, and/or conditions, which can be treated with the PSGR compositions of the invention (e.g., PSGR polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the PSGR polypeptides, polynucleotides, or agonists or antagonists of the invention are used to protect neural cells from the damaging effects of cerebral hypoxia. According to this embodiment, the PSGR compositions of the invention are used to treat, prevent, and/or diagnose neural cell injury associated with cerebral hypoxia. In one aspect of this embodiment, the PSGR polypeptides, polynucleotides, or agonists or antagonists of the invention are used to treat, prevent, and/or diagnose neural cell injury associated with cerebral ischemia. In another aspect of this embodiment, the PSGR polypeptides, polynucleotides, or agonists or antagonists of the invention are used to treat, prevent, and/or diagnose neural cell injury associated with cerebral infarction. In another aspect of this embodiment, the PSGR polypeptides, polynucleotides, or agonists or antagonists of the invention are used to treat, prevent, and/or diagnose neural cell injury associated with a stroke. In a further aspect of this embodiment, the PSGR polypeptides, polynucleotides, or agonists or antagonists of the invention are used to treat, prevent, and/or diagnose neural cell injury associated with a heart attack.

The compositions of the invention which are useful for treating, preventing, and/or diagnosing a nervous system disorder may be selected by testing for biological activity in promoting the survival or differentiation of neurons. For example, and not by way of limitation, PSGR compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507–3515 (1990)); increased sprouting of neurons may be detected by methods known in the art, such as, for example, the methods set forth in Pestronk et al. (Exp. Neurol. 70:65–82 (1980)) or Brown et al. (Ann. Rev. Neurosci. 4:17–42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Additional examples of neurologic diseases which can be treated, prevented, and/or diagnosed with polynucleotides, polypeptides, agonists, and/or antagonists of the present invention include brain diseases, such as metabolic brain diseases which includes phenylketonuria such as maternal phenylketonuria, pyruvate carboxylase deficiency, pyruvate dehydrogenase complex deficiency, Wernicke's Encephalopathy, brain edema, brain neoplasms such as cerebellar neoplasms which include infratentorial neoplasms, cerebral ventricle neoplasms such as choroid plexus neoplasms, hypothalamic neoplasms, supratentorial neoplasms, canavan disease, cerebellar diseases such as cerebellar ataxia which include spinocerebellar degeneration such as ataxia telangiectasia, cerebellar dyssynergia, Friederich's Ataxia, Machado-Joseph Disease, olivopontocerebellar atrophy, cerebellar neoplasms such as infratentorial neoplasms, diffuse cerebral sclerosis such as encephalitis periaxialis, globoid cell leukodystrophy, metachromatic leukodystrophy and subacute sclerosing panencephalitis, cerebrovascular diseases, disorders, and/or conditions (such as carotid artery diseases which include carotid artery thrombosis, carotid stenosis and Moyamoya Disease, cerebral amyloid angiopathy, cerebral aneurysm, cerebral anoxia, cerebral arteriosclerosis, cerebral arteriovenous malformations, cerebral artery diseases, cerebral embolism and thrombosis such as carotid artery thrombosis, sinus thrombosis and Wallenberg's Syndrome, cerebral hemorrhage such as epidural hematoma, subdural hematoma and subarachnoid hemorrhage, cerebral infarction, cerebral ischemia such as transient cerebral ischemia, Subclavian Steal Syndrome and vertebrobasilar insufficiency, vascular dementia such as multi-infarct dementia, periventricular leukomalacia, vascular headache such as cluster headache, migraine, dementia such as AIDS Dementia Complex, presenile dementia such as Alzheimer's Disease and Creutzfeldt-Jakob Syndrome, senile dementia such as Alzheimerz's Disease and progressive supranuclear palsy, vascular dementia such as multi-infarct dementia, encephalitis which include encephalitis periaxialis, viral encephalitis such as epidemic encephalitis, Japanese Encephalitis, St. Louis Encephalitis, tick-borne encephalitis and West Nile Fever, acute disseminated encephalomyelitis, meningoencephalitis such as uveomeningoencephalitic syndrome, Postencephalitic Parkinson Disease and subacute sclerosing panencephalitis, encephalomalacia such as periventricular leukomalacia, epilepsy such as generalized epilepsy which includes infantile spasms, absence epilepsy, myoclonic epilepsy which includes MERRF Syndrome, tonic-clonic epilepsy, partial epilepsy such as complex partial epilepsy, frontal lobe epilepsy and temporal lobe epilepsy, post-traumatic epilepsy, status epilepticus such as Epilepsia Partialis Continua, Hallervorden-Spatz Syndrome, hydrocephalus such as Dandy-Walker Syndrome and normal pressure hydrocephalus, hypothalamic diseases such as hypothalamic neoplasms, cerebral malaria, narcolepsy which includes cataplexy, bulbar poliomyelitis, cerebri pseudotumor, Rett Syndrome, Reye's Syndrome, thalamic diseases, cerebral toxoplasmosis, intracranial tuberculoma and Zellweger Syndrome, central nervous system infections such as AIDS Dementia Complex, Brain Abscess, subdural empyema, encephalomyelitis such as Equine Encephalomyelitis, Venezuelan Equine Encephalomyelitis, Necrotizing Hemorrhagic Encephalomyelitis, Visna, cerebral malaria, meningitis such as arachnoiditis, aseptic meningitis such as viral meningtitis which includes lymphocytic choriomeningitis. Bacterial meningtitis which includes Haemophilus Meningtitis, Listeria Meningtitis, Meningococcal Meningtitis such as Waterhouse-Friderichsen Syndrome, Pneumococcal Meningtitis and meningeal tuberculosis, fungal meningitis such as Cryptococcal Meningtitis, subdural effusion, meningoencephalitis such as uvemeningoencephalitic syndrome, myelitis such as transverse myelitis, neurosyphilis such as tabes dorsalis, poliomyelitis which includes bulbar poliomyelitis and postpoliomyelitis syndrome, prion diseases (such as Creutzfeldt-Jakob Syndrome, Bovine Spongiform Encephalopathy, Gerstmann-Straussler Syndrome, Kuru, Scrapie) cerebral toxoplasmosis, central nervous system neoplasms such as brain neoplasms that include cerebellear neoplasms such as infratentorial neoplasms, cerebral ventricle neoplasms such as choroid plexus neoplasms, hypothalamic neoplasms and supratentorial neoplasms, meningeal neoplasms, spinal cord neoplasms which include epidural neoplasms, demyelinating diseases such as Canavan Diseases, diffuse cerebral sceloris which includes adrenoleukodystrophy, encephalitis periaxialis, globoid cell leukodystrophy, diffuse cerebral sclerosis such as metachromatic leukodystrophy, allergic encephalomyelitis, necrotizing hemorrhagic encephalomyelitis, progressive multifocal leukoencephalopathy, multiple sclerosis, central pontine myelinolysis, transverse myelitis, neuromyelitis optica, Scrapie, Swayback, Chronic Fatigue Syndrome, Visna, High Pressure Nervous Syndrome, Meningism, spinal cord diseases such as amyotonia congenita, amyotrophic lateral sclerosis, spinal muscular atrophy such as Werdnig-Hoffmann Disease, spinal cord compression, spinal cord neoplasms such as epidural neoplasms, syringomyelia, Tabes Dorsalis, Stiff-Man Syndrome, mental retardation such as Angelman Syndrome, Cri-du-Chat Syndrome, De Lange's Syndrome, Down Syndrome, Gangliosidoses such as gangliosidoses G(M1), Sandhoff Disease, Tay-Sachs Disease, Hartnup Disease, homocystinuria, Laurence-Moon-Biedl Syndrome, Lesch-Nyhan Syndrome, Maple Syrup Urine Disease, mucolipidosis such as fucosidosis, neuronal ceroid-lipofuscinosis, oculocerebrorenal syndrome, phenylketonuria such as maternal phenylketonuria, Prader-Willi Syndrome, Rett Syndrome, Rubinstein-Taybi Syndrome, Tuberous Sclerosis, WAGR Syndrome, nervous system abnormalities such as holoprosencephaly, neural tube defects such as anencephaly which includes hydrangencephaly, Arnold-Chairi Deformity, encephalocele, meningocele, meningomyelocele, spinal dysraphism such as spina bifida cystica and spina bifida occulta, hereditary motor and sensory neuropathies which include Charcot-Marie Disease, Hereditary optic atrophy, Refsum's Disease, hereditary spastic paraplegia, Werdnig-Hoffmann Disease, Hereditary Sensory and Autonomic Neuropathies such as Congenital Analgesia and Familial Dysautonomia, Neurologic manifestations (such as agnosia that include Gerstmann's Syndrome, Amnesia such as retrograde amnesia, apraxia, neurogenic bladder, cataplexy, communicative diseases, disorders, and/or conditions such as hearing diseases, disorders, and/or conditions that includes deafness, partial hearing loss, loudness recruitment and tinnitus, language diseases, disorders, and/or conditions such as aphasia which include agraphia, anomia, broca aphasia, and Wernicke Aphasia, Dyslexia such as Acquired Dyslexia, language development diseases, disorders, and/or conditions, speech diseases, disorders, and/or conditions such as aphasia which includes anomia, broca aphasia and Wernicke Aphasia, articulation diseases, disorders, and/or conditions, communicative diseases, disorders, and/or conditions such as speech disorders which include dysarthria, echolalia, mutism and stuttering, voice diseases, disorders, and/or conditions such as aphonia and hoarseness, decerebrate state, delirium, fasciculation, hallucinations, meningism, movement diseases, disorders, and/or conditions such as angelman syndrome, ataxia, athetosis, chorea, dystonia, hypokinesia, muscle hypotonia, myoclonus, tic, torticollis and tremor, muscle hypertonia such as muscle rigidity such as stiff-man syndrome, muscle spasticity, paralysis such as facial paralysis which includes Herpes Zoster Oticus, Gastroparesis, Hemiplegia, ophthalmoplegia such as diplopia, Duane's Syndrome, Homer's Syndrome, Chronic progressive external ophthalmoplegia such as Kearns Syndrome, Bulbar Paralysis, Tropical Spastic Paraparesis, Paraplegia such as Brown-Sequard Syndrome, quadriplegia, respiratory paralysis and vocal cord paralysis, paresis, phantom limb, taste diseases, disorders, and/or conditions such as ageusia and dysgeusia, vision diseases, disorders, and/or conditions such as amblyopia, blindness, color vision defects, diplopia, hemianopsia, scotoma and subnormal vision, sleep diseases, disorders, and/or conditions such as hypersomnia which includes Kleine-Levin Syndrome, insomnia, and somnambulism, spasm such as trismus, unconsciousness such as coma, persistent vegetative state and syncope and vertigo, neuromuscular diseases such as amyotonia congenita, amyotrophic lateral sclerosis, Lambert-Eaton Myasthenic Syndrome, motor neuron disease, muscular atrophy such as spinal muscular atrophy, Charcot-Marie Disease and Werdnig-Hoffmann Disease, Postpoliomyelitis Syndrome, Muscular Dystrophy, Myasthenia Gravis, Myotonia Atrophica, Myotonia Confenita, Nemaline Myopathy, Familial Periodic Paralysis, Multiplex Paramyloclonus, Tropical Spastic Paraparesis and Stiff-Man Syndrome, peripheral nervous system diseases such as acrodynia, amyloid neuropathies, autonomic nervous system diseases such as Adie's Syndrome, Barre-Lieou Syndrome, Familial Dysautonomia, Homer's Syndrome, Reflex Sympathetic Dystrophy and Shy-Drager Syndrome, Cranial Nerve Diseases such as Acoustic Nerve Diseases such as Acoustic Neuroma which includes Neurofibromatosis 2, Facial Nerve Diseases such as Facial Neuralgia, Melkersson-Rosenthal Syndrome, ocular motility diseases, disorders, and/or conditions which includes amblyopia, nystagmus, oculomotor nerve paralysis, ophthalmoplegia such as Duane's Syndrome, Horner's Syndrome, Chronic Progressive External Ophthalmoplegia which includes Kearns Syndrome, Strabismus such as Esotropia and Exotropia, Oculomotor Nerve Paralysis, Optic Nerve Diseases such as Optic Atrophy which includes Hereditary Optic Atrophy, Optic Disk Drusen, Optic Neuritis such as Neuromyelitis Optica, Papilledema, Trigeminal Neuralgia, Vocal Cord Paralysis, Demyelinating Diseases such as Neuromyelitis Optica and Swayback, Diabetic neuropathies such as diabetic foot, nerve compression syndromes such as carpal tunnel syndrome, tarsal tunnel syndrome, thoracic outlet syndrome such as cervical rib syndrome, ulnar nerve compression syndrome, neuralgia such as causalgia, cervico-brachial neuralgia, facial neuralgia and trigeminal neuralgia, neuritis such as experimental allergic neuritis, optic neuritis, polyneuritis, polyradiculoneuritis and radiculities such as polyradiculitis, hereditary motor and sensory neuropathies such as Charcot-Marie Disease, Hereditary Optic Atrophy, Refsum's Disease, Hereditary Spastic Paraplegia and Werdnig-Hoffmann Disease, Hereditary Sensory and Autonomic Neuropathies which include Congenital Analgesia and Familial Dysautonomia, POEMS Syndrome, Sciatica, Gustatory Sweating and Tetany).

Infectious Disease

PSGR polynucleotides or polypeptides, or agonists or antagonists of PSGR, can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, PSGR polynucleotides or polypeptides, or agonists or antagonists of PSGR, may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., Corynebacterium, Mycobacterium, Norcardia), *Cryptococcus neoformans*, Aspergillosis, Bacillaceae (e.g., Anthrax, Clostridium), Bacteroidaceae, Blastomycosis, Bordetella, Borrelia (e.g., *Borrelia burgdorferi*), Brucellosis, Candidiasis, Campylobacter, Coccidioidomycosis, Cryptococcosis, Dermatocycoses, *E. coli* (e.g., Enterotoxigenic *E. coli* and Enterohemorrhagic *E. coli*), Enterobacteriaceae (Klebsiella, Salmonella (e.g., *Salmonella typhi*, and *Salmonella paratyphi*), Serratia, Yersinia), Erysipelothrix, Helicobacter, Legionellosis, Leptospirosis, Listeria, Mycoplasmatales, *Mycobacterium leprae, Vibrio cholerae*, Neisseriaceae (e.g., Acinetobacter, Gonorrhea, Menigococcal), *Meisseria meningitidis*, Pasteurellacea Infections (e.g., Actinobacillus, Heamophilus (e.g., *Heamophilus influenza* type B), Pasteurella), Pseudomonas, Rickettsiaceae, Chlamydiaceae, Syphilis, Shigella spp., Staphylococcal, Meningiococcal, Pneumococcal and Streptococcal (e.g., *Streptococcus pneumoniae* and Group B Streptococcus). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

PSGR polynucleotides or polypeptides, or agonists or antagonists of PSGR, can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, PSGR polynucleotides or polypeptides, or agonists or antagonists of PSGR, may increase regeneration of tissues difficult to heal. For example, increased tendon/ligament regeneration would quicken recovery time after damage. PSGR polynucleotides or polypeptides, or agonists or antagonists of PSGR, of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using PSGR polynucleotides or polypeptides, or agonists or antagonists of PSGR, to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the PSGR polynucleotides or polypeptides, or agonists or antagonists of PSGR.

Chemotaxis

PSGR polynucleotides or polypeptides, or agonists or antagonists of PSGR, may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

PSGR polynucleotides or polypeptides, or agonists or antagonists of PSGR, may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that PSGR polynucleotides or polypeptides, or agonists or antagonists of PSGR, may inhibit chemotactic activity. These molecules could also be used to treat, prevent, and/or diagnose diseases, disorders, and/or conditions. Thus, PSGR polynucleotides or polypeptides, or agonists or antagonists of PSGR, could be used as an inhibitor of chemotaxis.

Binding Activity

PSGR polypeptides may be used to screen for molecules that bind to PSGR or for molecules to which PSGR binds. The binding of PSGR and the molecule may activate (agonist), increase, inhibit (antagonist), or decrease activity of the PSGR or the molecule bound. Examples of such molecules include antibodies, oligonucleotides, proteins (e.g., receptors), or small molecules.

Preferably, the molecule is closely related to the natural ligand of PSGR, e.g., a fragment of the ligand, or a natural substrate, a ligand, a structural or functional mimetic. (See, Coligan et al., Current Protocols in Immunology 1(2) :Chapter 5 (1991).) The molecule can be rationally designed using known techniques.

Preferably, the screening for these molecules involves producing appropriate cells which express PSGR, either as a secreted protein or on the cell membrane. Preferred cells include cells from mammals, yeast, Drosophila, or E. coli. Cells expressing PSGR (or cell membrane containing the expressed polypeptide) are then preferably contacted with a test compound potentially containing the molecule to observe binding, stimulation, or inhibition of activity of PSGR or the molecule.

The assay may simply test binding of a candidate compound to PSGR, wherein binding is detected by a label, or in an assay involving competition with a labeled competitor. Further, the assay may test whether the candidate compound results in a signal generated by binding to PSGR.

Alternatively, the assay can be carried out using cell-free preparations, polypeptide/molecule affixed to a solid support, chemical libraries, or natural product mixtures. The assay may also simply comprise the steps of mixing a candidate compound with a solution containing PSGR, measuring PSGR/molecule activity or binding, and comparing the PSGR molecule activity or binding to a standard.

Preferably, an ELISA assay can measure PSGR level or activity in a sample (e.g., biological sample) using a monoclonal or polyclonal antibody. The antibody can measure PSGR level or activity by either binding, directly or indirectly, to PSGR or by competing PSGR for a substrate.

Additionally, the receptor to which PSGR binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of PSGR thereby effectively generating agonists and antagonists of PSGR. See generally, U.S. Pat. Nos. 5,605,793, 5,811,238, 5,830,721, 5,834,252, and 5,837,458, and Patten, P. A., et al., *Curr. Opinion Biotechnol.* 8:724–33 (1997); Harayama, S. *Trends Biotechnol.* 16(2):76–82 (1998); Hansson, L. O., et al., *J. Mol. Biol.* 287:265–76 (1999); and Lorenzo, M. M. and Blasco, R. *Biotechniques* 24(2):308–13 (1998) (each of these patents and publications are hereby incorporated by reference). In one embodiment, alteration of PSGR polynucleotides and corresponding polypeptides may be achieved by DNA shuffling. DNA shuffling involves the assembly of two or more DNA segments into a desired PSGR molecule by homologous, or site-specific, recombination. In another embodiment, PSGR polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of PSGR may be recombined with one or more components, motifs, sections, parts, domains, fragments, etc. of one or more heterologous molecules. In preferred embodiments, the heterologous molecules are G-protein coupled receptor family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active PSGR fragments. Biologically active fragments are those exhibiting activity similar, but not necessarily identical, to an activity of the PSGR polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and $^3$[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of $^3$[H] thymidine in each case. The amount of fibroblast cell proliferation is measured by liquid scintillation chromatography which measures the incorporation of $^3$[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the PSGR receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to PSGR comprising the steps of: (a) incubating a candidate binding compound with PSGR; and (b) determining if binding has occurred. Moreover, the invention includes a method of identifying agonists/antagonists comprising the steps of: (a) incubating a candidate compound with PSGR, (b) assaying a biological activity, and (b) determining if a biological activity of PSGR has been altered.

Also, one could identify molecules bind PSGR experimentally by using the beta-pleated sheet regions disclosed in FIG. 3 and Table 1. Accordingly, specific embodiments of the invention are directed to polynucleotides encoding polypeptides which comprise, or alternatively consist of, the amino acid sequence of each beta pleated sheet regions disclosed in FIG. 3/Table 1. Additional embodiments of the invention are directed to polynucleotides encoding PSGR polypeptides which comprise, or alternatively consist of, any combination or all of the beta pleated sheet regions disclosed in FIG. 3/Table 1. Additional preferred embodiments of the invention are directed to polypeptides which comprise, or alternatively consist of, the PSGR amino acid sequence of each of the beta pleated sheet regions disclosed in FIG. 3/Table 1. Additional embodiments of the invention are directed to PSGR polypeptides which comprise, or alternatively consist of, any combination or all of the beta pleated sheet regions disclosed in FIG. 3/Table 1.

Targeted Delivery

In another embodiment, the invention provides a method of delivering compositions to targeted cells expressing a PSGR polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

In a specific embodiment, the invention provides a method for the specific destruction of prostate cells by administering polypeptides of the invention (e.g., polypeptides of the invention or antibodies of the invention) in association with toxins or cytotoxic prodrugs.

In a preferred embodiment, the invention provides a method for the specific destruction of aberrant or diseased prostate cells by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

Antisense And Ribozyme (Antagonists)

In specific embodiments, antagonists according to the present invention are nucleic acids corresponding to the sequences contained in SEQ ID NO:1, or the complementary strand thereof, and/or to nucleotide sequences contained in the deposited clone 97131. n one embodiment, antisense sequence is generated internally, by the organism, in another embodiment, the antisense sequence is separately administered (see, for example, O'Connor, J., Neurochem. 56:560 (1991). Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5' end and a HindIII site on the 3' end. Next, the pair of oligonucleotides is heated at 90° C. for one minute and then annealed in 2× ligation buffer (20 mM TRIS HCl pH 7.5, 10 mM MgC12, 10 MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the PSGR antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the PSGR antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding PSGR, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:144–1445 (1981), the regulatory sequences of the metallothionein gene (Brinster, et al., Nature 296:39–42 (1982)), etc.

The antisense nucleic acids of the invention comprise a sequence complementary to at least a portion of an RNA transcript of a PSGR gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded PSGR antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a PSGR RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'-non-translated, non-coding regions of PSGR shown in FIGS. 1A–B could be used in an antisense approach to inhibit translation of endogenous PSGR mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of PSGR mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., 1987, Nucl. Acids Res. 15:6625–664). The oligonucleotide is a 2'-0-methylribonucleotide (Inoue et al., 1987, Nucl. Acids Res. 15:613–6148), or a chimeric RNA-DNA analogue (Inoue et al., 1987, FEBS Lett. 215:327–330).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–745), etc.

While antisense nucleotides complementary to the PSGR coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222–1225 (1990). While ribozymes that cleave mRNA at site specific recognition sequences can be used to destroy PSGR mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of PSGR (FIGS. 1A–B). Preferably, the ribozyme is engineered so that the cleavage recognition site is located near the 5' end of the PSGR mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express PSGR in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous PSGR messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Other Activities

A polypeptide, polynucleotide, agonist, or antagonist of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. The polypeptide, polynucleotide, agonist, or antagonist of the present invention may also be employed to stimulate angiogenesis and limb regeneration, as discussed above.

A polypeptide, polynucleotide, agonist, or antagonist of the present invention may also be employed for treating, preventing, and/or diagnosing wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

A polypeptide, polynucleotide, agonist, or antagonist of the present invention may also be employed stimulate neuronal growth and to treat and prevent neuronal damage which occurs in certain neuronal diseases, disorders, and/or conditions or neuro-degenerative conditions such as Alzheimer's disease, Parkinson's disease, and AIDS-related complex. A polypeptide, polynucleotide, agonist, or antagonist of the present invention may have the ability to stimulate chondrocyte growth, therefore, they may be employed to enhance bone and periodontal regeneration and aid in tissue transplants or bone grafts.

A polypeptide, polynucleotide, agonist, or antagonist of the present invention may be also be employed to prevent skin aging due to sunburn by stimulating keratinocyte growth.

A polypeptide, polynucleotide, agonist, or antagonist of the present invention may also be employed for preventing hair loss, since FGF family members activate hair-forming cells and promotes melanocyte growth. Along the same lines, a polypeptide, polynucleotide, agonist, or antagonist of the present invention may be employed to stimulate growth and differentiation of hematopoietic cells and bone marrow cells when used in combination with other cytokines.

A polypeptide, polynucleotide, agonist, or antagonist of the present invention may also be employed to maintain organs before transplantation or for supporting cell culture of primary tissues. A polypeptide, polynucleotide, agonist, or antagonist of the present invention may also be employed for inducing tissue of mesodermal origin to differentiate in early embryos.

A polypeptide, polynucleotide, agonist, or antagonist of the present invention may also increase or decrease the differentiation or proliferation of embryonic stem cells, besides, as discussed above, hematopoietic lineage.

A polypeptide, polynucleotide, agonist, or antagonist of the present invention may also be used to modulate mammalian characteristics, such as body height, weight, hair color, eye color, skin, percentage of adipose tissue, pigmentation, size, and shape (e.g., cosmetic surgery). Similarly, a polypeptide, polynucleotide, agonist, or antagonist of the present invention may be used to modulate mammalian metabolism affecting catabolism, anabolism, processing, utilization, and storage of energy.

A polypeptide, polynucleotide, agonist, or antagonist of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

A polypeptide, polynucleotide, agonist, or antagonist of the present invention may also be used as a food additive or preservative, such as to increase or decrease storage capabilities, fat content, lipid, protein, carbohydrate, vitamins, minerals, cofactors or other nutritional components.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

Having generally described the invention, the same will be more readily understood by reference to the following examples, which are provided by way of illustration and are not intended as limiting.

EXAMPLE 1

Expression and Purification of a Soluble Portion of PSGR in E. coli

The bacterial expression vector pQE60 is used for bacterial expression in this example. (QIAGEN, Inc., 9259 Eton Avenue, Chatsworth, Calif., 9131). pQE60 encodes ampicillin antibiotic resistance ("Amp$^r$") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6xHis tag") covalently linked to the carboxyl terminus of that polypeptide.

The DNA sequence encoding the desired portion of the PSGR protein is amplified from the deposited cDNA clone using PCR oligonucleotide primers which anneal to the amino terminal sequences of the desired portion of the PSGR protein or to the carboxy terminal sequences of the desired protion of the PSGR protein. Additional nucleotides containing restriction sites to facilitate cloning in the pQE60 vector are added to the 5' and 3' sequences, respectively.

For cloning the the portion of PSGR from Arg-262 to Lys-321, the 5' primer has the sequence: 5'-ACTG <u>CCATGG</u>GCCGCTTTGGAAACAGCCTTCAT-3' (SEQ ID NO:4) containing the underlined NcoI restriction site followed by nucleotides complementary to the coding sequence starting at Arg-262 of the PSGR in FIGS. 1A–B. One of ordinary skill in the art would appreciate, of course, that the point in the protein coding sequence where the 5' primer begins may be varied to amplify a desired portion of the complete protein shorter or longer than that described herein.

The 3' primer has the sequence: 5'-GTAC <u>AGATCT</u>CTTGCCTCCCACAGCCTG -3' (SEQ ID NO:5) containing the underlined BglII site followed by nucleotides complementary to 3' sequences in the PSGR DNA sequence in FIGS. 1A–B.

The amplified PSGR DNA fragments and the vector pQE60 are digested with Nco I and BglII and the digested DNAs then ligated together. Insertion of the PSGR protein DNA into the restricted pQE60 vector places the PSGR protein coding region (including its associated stop codon) downstream from the IPTG-inducible promoter and in-frame with an initiating AUG. The associated stop codon prevents translation of the six histidine codons downstream of the insertion point.

The ligation mixture is transformed into competent E. coli cells using standard procedures. Such procedures are described in Sambrook et al., Molecular Cloning: a Laboratory Manual, 2nd Ed.; Cold Spring Harbor Laboratory Press, Cold Spring Harbor, N.Y. (1989). E. coli strain M15/rep4, containing multiple copies of the plasmid pREP4, which expresses lac repressor and confers kanamycin resistance ("Kan$^r$"), is used in carrying out the illustrative example described herein. This strain, which is only one of many that are suitable for expressing PSGR protein, is available commercially from Qiagen, Inc., supra.

Transformants are identified by their ability to grow on LB plates in the presence of ampicillin and kanamycin. Plasmid DNA is isolated from resistant colonies and the identity of the cloned DNA confirmed by restriction analysis, PCR, and DNA sequencing.

Clones containing the desired constructs are grown overnight ("O/N") in liquid culture in LB media supplemented with both ampicillin (100 ug/ml) and kanamycin (25 ug/ml). The O/N culture is used to inoculate a large culture, at a dilution of approximately 1:100 to 1:250. The cells are grown to an optical density at 600 nm ("OD600") of between 0.4 and 0.6. sopropyl-B-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH8. The cell debris is removed by centrifugation, and the supernatant containing the PSGR is loaded onto a nickel-nitrilo-tri-acetic acid ("NiNTA") affinity resin column (available from QIAGEN, Inc., supra). Proteins with a 6xHis tag bind to the NI-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH8, the column is first washed with 10 volumes of 6 M guanidine-HCl, pH8, then washed with 10 volumes of 6 M guanidine-HCl pH6, and finally the PSGR is eluted with 6 M guanidine-HCl, pH5.

The purified protein is then renatured by dialyzing it against phosphatebuffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH6 buffer plus 200 mM NaCl. The purified protein is stored at 4° C. or frozen at –80° C.

EXAMPLE 2

Cloning and Expression of PSGR in a Baculovirus Expression System

In this illustrative example, the plasmid shuttle vector pA2 is used to insert the cloned DNA encoding the complete protein, including its naturally associated secretary signal (leader) sequence, into a baculovirus to express the mature PSGR protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI and Asp718. The polyadenylation site of the simian virus 40 ("SV40") is used for efficient polyadenylation. For easy selection of recombinant virus, the plasrmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:3–39 (1989).

The cDNA sequence encoding the full length PSGR receptor protein in the deposited clone shown in FIGS. 1A–B (SEQ ID NO:2), is amplified using PCR oligonucleotide primers corresponding to the 5' and 3' sequences of the gene.

The 5' primer has the sequence 5'-GCTAG TCTAGATCCGCCATCATGAGTTCCTGCAACTTC-3' (SEQ ID NO:6) containing the underlined Xba I restriction enzyme site, an efficient signal for initiation of translation in eukaryotic cells, as described by M. Kozak, *J. Mol. Biol.* 196:947–950 (1987), followed by bases of the sequence of the full length PSGR protein shown in FIGS. 1A–B, beginning with the indicated N-terminus of the protein.

The 3' primer for PSGR has the sequence 5'-GCAGCA GGTACCTCACTTGCCTCCCACAGC-3' (SEQ ID NO:7) containing the underlined Asp 718 restriction site followed by nucleotides complementary to the 3' end of the coding sequence in FIGS. 1A–B.

The amplified fragment is isolated from a 1% agarose gel using a commercially available kit ("Geneclean," B101 Inc., La Jolla, Calif.) The fragment then is digested with Xba I and Asp 718 and again is purified on a 1% agarose gel. This fragment is designated "F1."

The plasmid is digested with the restriction enzyme Xba I and Asp718 and optionally can be dephosphorylated using calf intestinal phosphatase, using routine procedures known in the art. The DNA is then isolated from a 1% agarose gel using a commercially available kit ("Geneclean" BIO 101 Inc., La Jolla, Calif.). The vector DNA is designated herein "V1."

Fragment F1 and the dephosphorylated plasmid V1 are ligated together with T4 DNA ligase. *E. coli* HB 101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with the human PSGR gene using the PCR method, in which one of the primers that is used to amplify the gene and the second primer is from well within the vector so that only those bacterial colonies containing the PSGR gene fragment will show amplification of the DNA. The sequence of the cloned fragment is confirmed by DNA sequencing. This plasmid is designated herein pBac PSGR.

Five ug of the plasmid pBac PSGR is co-transfected with 1.0 ug of a commercially available linearized baculovirus DNA ("BaculoGold™ baculovirus DNA", Pharmingen, San Diego, Calif.), using the lipofectin method described by Felgner et al., *Proc. Natl. Acad. Sci. USA* 84:7413–7417 (1987). 1 ug of BaculoGold™ virus DNA and 5 ug of the plasmid pBac PSGR are mixed in a sterile well of a microliter plate containing 50 ul of serum free Grace's medium (Life Technologies, Inc., Rockville, Md.). Afterwards, 10 ul Lipofectin plus 90 $_{13}$1 Grace's medium are added, mixed, and incubated for 15 minutes at room temperature. Then, the transfection mixture is added dropwise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours, the transfection solution is removed from the plate and 1 ml of Grace's insect medium supplemented with 10% fetal calf serum is added. The plate is put back into an incubator and cultivation is continued at 27° C. for four days.

After four days, the supernatant is collected and a plaque assay is performed, as described by Summers and Smith, cited above. An agarose gel with "Blue Gal" (Life Technologies, Inc., Rockville, Md.) is used to allow easy identification and isolation of gal-expressing clones, which produce blue-stained plaques. (A detailed description of a "plaque assay" of this type can also be found in the user's guide for insect cell culture and baculovirology distributed by Life Technologies, Inc., Rockville, Md., pages 9–10). After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-PSGR.

To verify the expression of the PSGR gene, Sf9 cells are grown in Grace's medium supplemented with 10% heat inactivated FBS. The cells are infected with the recombinant baculovirus V-PSGR at a multiplicity of infection ("MOI") of about 2. Six hours later the medium is removed and is replaced with SF900 II medium minus methionine and cysteine (available from Life Technologies, Inc., Rockville, Md.). If radiolabeled proteins are desired, 42 hours later, 5 uCi of $^{35}$S-methionine and 5 uCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

EXAMPLE 3

Cloning and Expression of the PSGR Receptor in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing.

Highly efficient transcription can be achieved with the early and late promoters from SV40, the long terminal repeats (LTRs) from Retroviruses, e.g. RSV, HTLVI, HIVI and the early promoter of the cytomegalovirus (CMV). However, cellular signals can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela 293, H9 and Jurkat cells, mouse NIH3T3 and C127 cells, Cos 1, Cos 7 and CV1, quail QC1-3 cells, mouse L cells, and Chinese hamster ovary (CHO) cells.

Alternatively, the gene can be expressed in stable cell lines that contain the gene integrated into a chromosome. Co-transfection with a selectable marker such as dhfr, gpt, neomycin, or hygromycin allows the identification and isolation of the transfected cells.

The transfected gene can also be amplified to express large amounts of the encoded protein. The dihydrofolate reductase (DHFR) marker is useful to develop cell lines that carry several hundred or even several thousand copies of the gene of interest. Another useful selection marker is the enzyme glutamine synthase (GS) (Murphy et al., *Biochem. J.* 227:277–279 (1991); Bebbington et al., *Bio/Technology* 10:169–175 (1992)). Using these markers, the mammalian cells are grown in selective medium and the cells with the highest resistance selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology* 5:438–447 (March 1985)), plus a fragment of the CMV-enhancer (Boshart et al., *Cell* 41:52–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

EXAMPLE 3A

Cloning and Expression of the Full Length PSGR in COS cells

The expression plasmid, pCDNA3.1:HPRAJ70.Flag, is made by cloning a cDNA encoding PSGR into the expression vector pCDNA3.1 (which can be obtained from Invitrogen, Inc.).

The expression vector pCDNA3.1 contains: (1) an *E. coli* origin of replication effective for propagation in *E. coli* and other prokaryotic cell; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire PSGR precursor and a FLAG tag fused in frame to its 3' end is cloned into the polylinker region of the vector so that recombinant protein expression is directed by the CMV promoter. The FLAG tag corresponds to the 11 amino acid leader peptide of the gene 10 product from bacteriophage T7 described by Witzgall et al., *Anal. Biochem.* 223:29–8 (1994). The fusion of the FLAG tag to the target protein allows easy detection of the recombinant protein with an antibody that recognizes the FLAG epitope.

The plasmid construction strategy is as follows:

Portions of the PSGR cDNA of the deposited clones is amplified using primers that contain convenient restriction sites, much as described above regarding the construction of expression vectors for expression of PSGR in *E. coli*.

To facilitate detection, purification and characterization of the expressed PSGR, one of the primers contains a FLAG tag as described above.

Suitable primers for PSGR include the following, which are used in this example:

The 5' primer,

5'                                        CATGGA AGATCTGCCACCATGGACTACAAAGACGATGAC GACAAGAGT TCCTGCAACTTCACAC-3' (SEQ ID NO:8) contains the underlined BglII site, an ATG start codon and in-frame FLAG tag, and the first seven codons of PSGR. The 3' primer for PSGR contains the underlined XbaI site, the last 21 nucleotides of the 3' coding sequence (at the 3' end), and has the following sequence:

5'-CATTGC TCTAGATCACTTGCCTCCCACAGCCTG-3' (SEQ ID NO:9).

The PCR amplified DNA fragment and the vector, pCDNA3.1, are digested with BglII and XbaI and then ligated. The ligation mixture is transformed into *E. coli* strain SURE (available from Stratagene Cloning Systems, 11099 North Torrey Pines Road, La Jolla, Calif. 92037) the transformed culture is plated on ampicillin media plates which then are incubated to allow growth of ampicillin resistant colonies. Plasmid DNA is isolated from resistant colonies and examined by restriction analysis and gel sizing for the presence of the PSGR-encoding fragment.

For expression of recombinant PSGR, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of PSGR by the vector.

Expression of the FLAG-PSGR fusion protein is detected by radiolabelling and immunoprecipitation, using methods described in, for example Harlow et al., *Antibodies: a Laboratory Manual*, 2nd Ed., Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and then lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

EXAMPLE 4

Protein Fusions of PSGR

PSGR polypeptides of the invention are optionally fused to other proteins. These fusion proteins can be used for a variety of applications. For example, fusion of PSGR polypeptides to His-tag, HA-tag, protein A, IgG domains, and maltose binding protein facilitates purification. (See EP A 394,827; Traunecker, et al., *Nature* 331:84–86 (1988)). Similarly, fusion to IgG-1, IgG-3, and albumin increases the halflife time in vivo. Nuclear localization signals fused to PSGR polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made using techniques known in the art or by using or routinely modifying the following protocol, which outlines the fusion of a polypeptide to an IgG molecule.

Briefly, the human Fc portion of the IgG molecule can be PCR amplified, using primers that span the 5' and 3' ends of the sequence described below (SEQ ID NO:10). These primers also preferably contain convenient restriction enzyme sites that will facilitate cloning into an expression vector, preferably a mammalian expression vector.

For example, if the pC4 (Accession No. 209646) expression vector is used, the human Fc portion can be ligated into the BamHI cloning site. Note that the 3' BamHI site should be destroyed. Next, the vector containing the human Fc portion is re-restricted with BamHI, linearizing the vector, and PSGR polynucleotide, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:

playing antibody fragments, approximately $10^9$ E. coli harbouring the phagemid are used to inoculate 50 ml of 2×TY containing 1% glucose and 100 ug/ml of ampicillin (2×TY-AMP-GLU) and grown to an O.D. of 0.8 with shaking. Five ml of this culture is used to innoculate 50 ml of 2×TY-AMP-GLU, $2\times10^8$ TU of Δ gene 3 helper phage (M13 Δ gene III, see WO92/01047) are added and the culture incubated at 37° C. for 45 minutes without shaking and then at 37° C. for 45 minutes with shaking. The culture is centrifuged at 4000 r.p.m. for 10 minutes and the pellet resuspended in 2 liters of 2×TY containing 100 ug/ml ampicillin and 50 ug/ml kanamycin and grown overnight. Phage are prepared as described in WO92/01047.

M13 Δ gene III is prepared as follows: M13 Δ gene III helper phage does not encode gene III protein, hence the phage(mid) displaying antibody fragments have a greater avidity of binding to antigen. Infectious M13 Δ gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are pelleted (IEC-Centra 8, 4000 revs/min for 10 min), resuspended in 300 ml 2×TY broth containing 100 ug ampicillin/ml and 25 ug kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 um filter (Minisart NML; Sartorius) to give a final concentration of approximately $10^{13}$ transducing units/ml (ampicillin-resistant clones).

Panning of the Library

Immunotubes (Nunc) are coated overnight in PBS with 4 ml of either 100 mg/ml or 10 mg/ml of a polypeptide of the

```
GGGATCCGGAGCCCAAATCTTCTGACAAAACTCACACATGCCCACCGTGCCCAGCACCTGAATTC    (SEQ ID NO:10)

GAGGGTGCACCGTCAGTCTTCCTCTTCCCCCCAAAACCCAAGGACACCCTCATGATCTCCCGGACT

CCTGAGGTCACATGCGTGGTGGTGGACGTAAGCCACGAAGACCCTGAGGTCAAGTTCAACTGGTA

CGTGGACGGCGTGGAGGTGCATAATGCCAAGACAAAGCCGCGGGAGGAGCAGTACAACAGCACG

TACCGTGTGGTCAGCGTCCTCACCGTCCTGCACCAGGACTGGCTGAATGGCAAGGAGTACAAGTG

CAAGGTCTCCAACAAAGCCCTCCCAACCCCCATCGAGAAAACCATCTCCAAAGCCAAAGGGCAGC

CCCGAGAACCACAGGTGTACACCCTGCCCCCATCCCGGGATGAGCTGACCAAGAACCAGGTCAGC

CTGACCTGCCTGGTCAAAGGCTTCTATCCAAGCGACATCGCCGTGGAGTGGGAGAGCAATGGGCA

GCCGGAGAACAACTACAAGACCACGCCTCCCGTGCGGACTCCGACGGCTCCTTCTTCCTCTACAG

CAAGCTCACCGTGGACAAGAGCAGGTGGCAGCAGGGGAACGTCTTCTCATGCTCCGTGATGCATG

AGGCTCTGCACAACCACTACACGCAGAAGAGCCTCTCCCTGTCTCCGGGTAAATGAGTGCGACGG

CCGCGACTCTAGAGGAT
```

EXAMPLE 5
Isolation of Antibody Fragments Directed against Polypeptides of the Present Invention from a Library of scFvs Naturally occuring V-genes isolated from human PBLs are constructed into a large library of antibody fragments which contain reactivities against polypeptides of the present invention to which the donor may or may not have been exposed (see e.g., U.S. Pat. No. 5,885,793 incorporated herein in its entirety by reference).

Rescue of the Library

A library of scFvs is constructed from the RNA of human PBLs as described in WO92101047. To rescue phage dis-present invention. Tubes are blocked with 2% Marvel-PBS for 2 hours at 37° C. and then washed 3 times in PBS. Approximately $10^{13}$ TU of phage are applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0 M Tris-HCl, pH 7.4. Phage are then used to infect 10 ml of mid-log E. coli TG1 by incubating eluted phage with bacteria for 30 minutes at 37° C. The *E. coli* are then plated on TYE plates containing 1% glucose and 100 ug/ml ampicillin. The resulting bacterial library is then rescued with Δ gene III helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

EXAMPLE 6
Tissue Distribution of PSGR mRNA Expression

Northern blot analysis was carried out to examine PSGR gene expression in human tissues, using methods described by, among others, Sambrook et al., cited above. A cDNA probe containing the entire nucleotide sequence of the PSGR protein (SEQ ID NO:1) was labeled with $^{32}$P using the rediprime™ DNA labeling system (Amersham Life Science), according to manufacturer's instructions. After labeling, the probe was purified using a CHROMA SPIN-100 column (Clontech Laboratories, Inc.), according to manufacturer's protocol number PT1200-1. The purified labeled probe was then used to examine various human tissues for PSGR mRNA.

Multiple Tissue Northern (MTN) blots containing various human tissues (H) or human immune system tissues (IM) were obtained from Clontech and were examined with labeled probe using ExpressHyb™ hybridization solution (Clontech) according to manufacturer's protocol number PT1190-1. Following hybridization and washing, the blots were mounted and exposed to film at −70° C. overnight, and films developed according to standard procedures. Expression of PSGR was detected in normal and diseased prostate tissues. It can be envisaged that PSGR plays a role in prostate function.

EXAMPLE 7
Method of Determining Alterations in the PSGR Gene

RNA is isolated from entire families or individual patients presenting with a phenotype of interest (such as a disease). cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95° C. for 30 seconds; 60–120 seconds at 52–58° C.; and 60–120 seconds at 70° C., using buffer solutions described in Sidransky, D., et al., *Science* 252:706 (1991).

PCR products are then sequenced using primers labeled at their 5' end with T4 polynucleotide kinase, employing SequiTherm Polymerase. (Epicentre Technologies). The intron-exon borders of selected exons of PSGR are also determined and genomic PCR products analyzed to confirm the results. PCR products harboring suspected mutations in PSGR is then cloned and sequenced to validate the results of the direct sequencing.

PCR products of PSGR are cloned into T-tailed vectors as described in Holton, T. A. and Graham, M. W., *Nucleic Acids Research*, 19:1156 (1991) and sequenced with T7 polymerase (United States Biochemical). Affected individuals are identified by mutations in PSGR not present in unaffected individuals.

Genomic rearrangements are also observed as a method of determining alterations in the PSGR gene. Genomic clones isolated using techniques known in the art are nick-translated with digoxigenindeoxy-uridine 5' -triphosphate (Boehringer Manheim), and FISH performed as described in Johnson, Cg. et al., *Methods Cell Biol.* 35:73–99 (1991). Hybridization with the labeled probe is carried out using a vast excess of human cot-1 DNA for specific hybridization to the PSGR genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., *Genet. Anal. Tech. Appl.*, 8:75 (1991).) Image collection, analysis and chromosomal fractional length measurements are performed using the ISee Graphical Program System. (Inovision Corporation, Durham, N.C.) Chromosome alterations of the genomic region of PSGR (hybridized by the probe) are identified as insertions, deletions, and translocations. These PSGR alterations are used as a diagnostic marker for an associated disease.

EXAMPLE 8
Method of Detecting Abnormal Levels of PSGR in a Biological Sample PSGR polypeptides can be detected in a biological sample, and if an increased or decreased level of PSGR is detected, this polypeptide is a marker for a particular phenotype. Methods of detection are numerous, and thus, it is understood that one skilled in the art can modify the following assay to fit their particular needs.

For example, antibody-sandwich ELISAs are used to detect PSGR in a sample, preferably a biological sample. Wells of a microtiter plate are coated with specific antibodies to PSGR, at a final concentration of 0.2 to 10 ug/ml. The antibodies are either monoclonal or polyclonal and are produced using technique known in the art. The wells are blocked so that non-specific binding of PSGR to the well is reduced.

The coated wells are then incubated for >2 hours at RT with a sample containing PSGR. Preferably, serial dilutions of the sample should be used to validate results. The plates are then washed three times with deionized or distilled water to remove unbounded PSGR.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

75 ul of 4-methylumbelliferyl phosphate (MUP) or p-nitrophenyl phosphate (NPP) substrate solution is then added to each well and incubated 1 hour at room temperature to allow cleavage of the substrate and flourescence. The flourescence is measured by a microtiter plate reader. A standard curve is preparded using the experimental results from serial dilutions of a control sample with the sample concentration plotted on the X-axis (log scale) and fluorescence or absorbance on the Y-axis (linear scale). The PSGR polypeptide concentration in a sample is then interpolated using the standard curve based on the measured flourescence of that sample.

EXAMPLE 9
Method of Treating Decreased Levels of PSGR

The present invention relates to a method for treating an individual in need of a decreased level of PSGR biological activity in the body comprising, administering to such an individual a composition comprising a therapeutically effective amount of PSGR antagonist. Preferred antagonists for use in the present invention are PSGR-specific antibodies.

Moreover, it will be appreciated that conditions caused by a decrease in the standard or normal expression level of PSGR in an individual can be treated by administering PSGR, preferably in a soluble and/or secreted form. Thus, the invention also provides a method of treatment of an individual in need of an increased level of PSGR polypeptide comprising administering to such an individual a pharmaceutical composition comprising an amount of PSGR to increase the biological activity level of PSGR in such an individual.

For example, a patient with decreased levels of PSGR polypeptide receives a daily dose 0.1–100 ug/kg of the polypeptide for six consecutive days. Preferably, the polypeptide is in a soluble and/or secreted form.

EXAMPLE 10
Method of Treating Increased Levels of PSGR

The present invention also relates to a method for treating an individual in need of an increased level of PSGR biological activity in the body comprising administering to such an individual a composition comprising a therapeutically effective amount of PSGR or an agonist thereof.

Antisense technology is used to inhibit production of PSGR. This technology is one example of a method of decreasing levels of PSGR polypeptide, preferably a soluble and/or secreted form, due to a variety of etiologies, such as cancer.

For example, a patient diagnosed with abnormally increased levels of PSGR is administered intravenously antisense polynucleotides at 0.5, 1.0, 1.5, 2.0 and 3.0 mg/kg day for 21 days. This treatment is repeated after a 7-day rest period if the is determined to be well tolerated.

EXAMPLE 11
Method of Treatment Using Gene Therapy—Ex Vivo

One method of gene therapy transplants fibroblasts, which are capable of expressing soluble and/or mature PSGR polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., *DNA*, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding PSGR can be amplified using PCR primers which correspond to the 5' and 3' end encoding sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform *E. coli* HB101, which are then plated onto agar containing kanamycin for the purpose of confirming that the vector contains properly inserted PSGR.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the PSGR gene is then added to the media and the packaging cells transduced with the vector. The packaging cells now produce infectious viral particles containing the PSGR gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether PSGR protein is produced.

The engineered fibroblasts are then transplanted onto the host, either alone or after having been grown to confluence on cytodex 3 microcarrier beads.

EXAMPLE 12
Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) PSGR sequences into an animal to increase or decrease the expression of the PSGR polypeptide. The PSGR polynucleotide may be operatively linked to a promoter or any other genetic elements necessary for the expression of the PSGR polypeptide by the target tissue. Such gene therapy and delivery techniques and methods are known in the art, see, for example, WO90/11092, WO98/11779; U.S. Pat. No. 5,693,622, 5,705,151, 5,580,859; Tabata H. et al., *Cardiovasc. Res*. 35:470–479 (1997); Chao J. et al., *Phannacol. Res*. 35:517–522 (1997); Wolff J. A. *Neuromuscul. Disord*. 7:314–318 (1997); Schwartz B. et al., *Gene Ther*. 3:405–411 (1996); Tsurumi Y. et al., *Circulation* 94:328–3290 (1996) (incorporated herein by reference).

The PSGR polynucleotide constructs may be delivered by any method that delivers injectable materials to the cells of an animal, such as, injection into the interstitial space of tissues (heart, muscle, skin, lung, liver, intestine and the like). The PSGR polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the PSGR polynucleotides may also be delivered in liposome formulations (such as those taught in Felgner P. L., et al. *Ann. NY Acad. Sci.* 772:126–139 (1995), and Abdallah B., et al. *Biol. Cell* 85(1):1–7 (1995)) which can be prepared by methods well known to those skilled in the art.

The PSGR polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The PSGR polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked PSGR polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked PSGR polynucleotide constructs can be delivered to arteries during angioplasty by the catheter used in the procedure.

The dose response effects of injected PSGR polynucleotide in muscle in vivo is determined as follows. Suitable PSGR template DNA for production of mRNA coding for PSGR polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The PSGR template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for PSGR protein expression. A time course for PSGR protein expression may be done in a similar fashion except that quadriceps from different mice are harvested at different times. Persistence of PSGR DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using PSGR naked DNA.

EXAMPLE 13

Gene Therapy using Endogenous PSGR Gene

Another method of gene therapy according to the present invention involves operably associating the endogenous PSGR sequence with a promoter via homologous recombination as described, for example, in U.S. Pat. No. 5,641,670, issued Jun. 24, 1997; nternational Publication Number WO 96/29411; nternational Publication Number WO 94/12650; Koller et al., *Proc. Natl. Acad. Sci. USA* 86:8932–8935 (1989); and Zijlstra et al., *Nature* 342:435–438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous PSGR, flanking the promoter. The targeting sequence will be sufficiently near the 5' end of PSGR so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous PSGR sequence. This results in the expression of PSGR in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the PSGR locus, plasmid pUC18 (MBI Fermentas, Amherst, N.Y.) is digested with HindIII. The CMV promoter is amplified by PCR with an XbaI site on the 5' end and a BamHI site on the 3'end. Two PSGR non-coding sequences are amplified via PCR: one PSGR non-coding sequence (PSGR fragment 1) is amplified with a HindIII site at the 5' end and an Xba site at the 3'end; the other PSGR non-coding sequence (PSGR fragment 2) is amplified with a BamHI site at the Send and a HindIII site at the 3'end. The CMV promoter and PSGR fragments are digested with the appropriate enzymes (CMV promoter—XbaI and BamHI; PSGR fragment 1—XbaI; PSGR fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately $1.5. \times 10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

EXAMPLE 14
Western Blotting, Immunoprecipitation, and Purification of PSGR

Anti-PSGR antibodies of the invention may be screened for the ability to bind plasma membrane preparations from PSGR expressing cells under reducing and non-reducing conditions via western blotting. PSGR is a membrane embedded protein, so in order to perform a western blot on PSGR proteins, cell membranes must first be solubilized. The following protocol was worked out by Mirzabekov et al., J. Biol. Chem. 274:28745 (1999) for western blotting of CCR5 (hereby incorporated in its entirety by reference herein). A single cell suspension of PSGR expressing cells and PSGR non-expressing cells, as a control, are pelleted and resuspended in solubilization buffer composed of 100 mM $(NH_4)_2SO_4$, 20 mM Tris-HCl (pH 7.5) and 1% (w/v) Cymal™-5 (Anatrace Inc., Maumee, Ohio), and protease inhibitor mixture (one tablet of Complete™ (Roche Molecular Biochemicals) per 25 ml). After a 30 minute incubation at 4° C. on a rocking platform, the samples are centrifuged for 30 minutes at 14,000×g to remove cell debris. PSGR may be immunoprecipitaed from the solubilized membrane using a specific anti-PSGR antibody (e.g., a monoclonal anti-PSGR antibody is preferred) conjugated to sepahrose beads. Following immunoprecipitation, the beads are washed extensively with solubilization buffer and resuspended in 2×SDS-sample buffer. Samples are incubated in SDS-sample buffer for 1 hour at 55° C. prior to electrophoresis through an 11% SDS-polyacrylamide gel. Western blotting on the PSGR samples is then carried out according to standard protocols known in the art, using antibodies of the invention as the primary anti-PSGR reagent. The expected molecular weight of PSGR in a Wetern blot is ~35 Kd (ranging from 30–40 kD).

The membrane solubilization protocol described above may also be used to prepare PSGR containing samples for purification.

EXAMPLE 15
PSGR Ligand Binding Assay

Antibodies of the invention may be assayed for their ability to prevent a natural ligand of PSGR from binding to the PSGR receptor. This assay is modified from Lopalco et al., J. Immunol., 164:3426 (2000) and Trkola et al., Nature, 384:184 (1996) which are incorporated in their entirities by reference herein. Briefly, $10^6$ PSGR expressing cells (e.g., PSGR transfected-CHO cells) are incubated on ice with appropriate dilution(s) of antibody of the invention. After 45 minutes of incubation, 0.2 microCuries of radiolabelled ligand is added to a final concentration of of 0.1 nM. After a two hour incubation on ice, unbound radioactivity is removed using a two step gradient, as described in Grassi et al., J Exp Med. 174:53 (1991) which is incorporated in its entirety by reference herein, in which the lower layer consists of fetal calf serum containing 10% sucrose, and the upper layer consists of 80% silicone (Sigma Aldrich) and 20% mineral oil (Sigma Aldrich). Bound radioactivity in cell pellets is measured in a gamma counter.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference.

Further, certain polynucleotides and polypeptides of the present invention, including antibodies, were disclosed in U.S. Provisional Application No. 60/237,275, filed Oct. 3, 2000, U.S. application Ser. No. 09/339,115, filed Jun. 24, 1999, U.S. application Ser. No. 09/053,303, filed Apr. 1, 1998, now U.S. Pat. No. 5,948,890, issued Sep. 7, 1999, and U.S. application Ser. No. 08/465,980, filed Jun. 6, 1995, now U.S. Pat. No. 5,756,309, issued May 26, 1998, as well as in International application number PCT/US95/07093, filed Jun. 5, 1995 (in English). The specifications, tables, figures and sequence listings of each of the above are herein incorporated by reference in their entireties.

Moreover, the Sequence Listing submitted herewith, in both computer and paper forms, is hereby incorporated by reference in its entirety.

---

What is claimed is:

1. An isolated antibody or fragment thereof that specifically binds a Prostate Specific G-Protein Receptor (PSGR) protein expressed on the surface of a cell wherein said PSGR protein is encoded by a polynucleotide encoding amino acids 1 to 320 of SEQ ID NO:2.

2. The antibody or fragment thereof of claim 1 which is a monoclonal antibody.

3. The antibody or fragment thereof of claim 1 which is a human antibody.

4. The antibody or fragment thereof of claim 1 which is selected from the group consisting of:

(a) a chimeric antibody;
(b) a polyclonal antibody;
(c) a humanized antibody;
(d) a single chain antibody; and
(e) a Fab fragment.

5. The antibody or fragment thereof of claim 1 wherein said antibody or fragment thereof specifically binds to said protein in a Western blot.

6. The antibody or fragment thereof of claim 1 wherein said antibody or fragment thereof specifically binds to said protein in an ELISA.

7. The antibody or fragment of claim 1 that is conjugated to a detectable label.

8. The antibody or fragment of claim 7, wherein the detectable label is an enzyme, a fluorescent label, or a radioisotope.

9. The antibody or fragment of claim 1, wherein the polynucleotide is operably associated with a regulatory sequence that controls expression of said polynucleotide.

10. The antibody or fragment of claim 1, wherein the cell is a mammalian cell.

11. The antibody or fragment of claim 1, wherein the mammalian cell is a CHO cell.

12. A method of detecting the protein of SEQ ID NO:2 or the protein of SEQ ID NO:4 in a biological sample comprising:
   (a) contacting a biological sample with the antibody or fragment of claim 1; and
   (b) determining the presence or absence of said protein in said biological sample.

13. A method of diagnosing prostate cancer comprising using the antibody of claim 1 to determine the level of PSGR polypeptide in a biological sample, wherein an increased level of PSGR relative to a control is indicative of prostate cancer.

14. A method of producing the antibody of claim 1 comprising immunizing an animal with a protein and recovering said antibody, wherein said protein is selected from the group consisting of:
   (a) a protein whose amino acid sequence comprises amino acid residues from 1 to 21 of SEQ ID NO:2;
   (b) a protein whose amino acid sequence comprises amino acid residues from about 77 to about 98 of SEQ ID NO:2;
   (c) a protein whose amino acid sequence comprises amino acid residues from about 163 to about 197 of SEQ ID NO:2; and
   (d) a protein whose amino acid sequence comprises amino acid residues from about 262 to about 272 of SEQ ID NO:2.

15. A method of producing the antibody of claim 1 comprising immunizing an animal with a cell expressing a PSGR protein consisting of amino acid 1 to 320 of SEQ ID NO:2 and recovering said antibody.

16. The method of claim 12 wherein said biological sample is obtained from a subject suspected of having prostate cancer.

* * * * *

UNITED STATES PATENT AND TRADEMARK OFFICE
CERTIFICATE OF CORRECTION

PATENT NO. : 6,824,993 B2  
DATED : November 30, 2004  
INVENTOR(S) : Soppet et al.

It is certified that error appears in the above-identified patent and that said Letters Patent is hereby corrected as shown below:

Title page,
Item [56], References Cited, OTHER PUBLICATIONS, delete the "Buck, et al." reference and insert the following references:
-- Buck, et al., "A Novel Multigene Family May Encode Odorant Receptors: A Molecular Basis for Odor Recognition," *Cell*, 65:175-187 (1991).
Hla, et al., "An Abundant Transcript Induced in Differentiating Human Endothelial Cells Encodes a Polypeptide With Structural Similarities," *J. Biol. Chem.*, 265 (16):9308-9313 (1990).
Xu, et al., "PSGR, a Novel Prostate-specific Gene with Homology to a G Protein-coupled Receptor is Overexpressed Prostate Cancer," *Cancer Research*, 60:6568-6572 (2000).
Wilson, et al., "Orphan G-protein-coupled Receptors: The Next Generation of Drug Targets?," *British J. Pharmacol.*, 125:1387-1392 (1998).
Pitcher, et al., "G Protein-coupled Receptor Kinases," *Annu. Rev. Biochem.*, 67:653-692 (1998).
Stadel, et al., "Orphan G Protein-coupled Recptors: A Neglected Opportunity for Pioneer Drug Discovery," *TIPS*, 18:430-437 (1997).
Edwards, et al., "Localization of G-protein-coupled Receptors in Health and Disease," *TIPS*, 21:304-308 (2000).
Ostrom, et al., "Stoichiometry and Compartmentation in G Protein-coupled Receptor Signaling: Implications for Therapeutic Interventions Involving Gsl," *JPET*. 294(2):407-412 (2000). --

Column 179,
Line 3, delete "fragment of claim 1," and insert -- fragment of claim 10, --.

Signed and Sealed this

Seventh Day of June, 2005

JON W. DUDAS  
*Director of the United States Patent and Trademark Office*

SEQUENCE LISTING

<160> NUMBER OF SEQ ID NOS: 12

<210> SEQ ID NO 1
<211> LENGTH: 1474
<212> TYPE: DNA
<213> ORGANISM: Homo sapiens
<220> FEATURE:
<221> NAME/KEY: CDS
<222> LOCATION: (274)..(1282)
<220> FEATURE:
<221> NAME/KEY: misc_feature
<222> LOCATION: (847)..(847)
<223> OTHER INFORMATION: n equals a, t, g, or c

<400> SEQUENCE: 1

```
ccatgctgcc ttccgggcag taccatccat ctccacaccc tggaagacac agtgagttag     60
caccaccacc aggtaattgg ccttatcagc tctgtgcctg tctccagtca ggctggaata    120
agtctcctca tatgtgcaag ctcggccctc ccctggaatc taaagcctcc tcagccttct    180
gagtcagcct gaaaggaaca ggccgaactg ctgtatgggc tctactgcca gtgtgacctc    240
accctctcca gtcacccctc ctcagttcca gct atg agt tcc tgc aac ttc aca    294
                                    Met Ser Ser Cys Asn Phe Thr
                                      1               5 cat gcc acc tgt gtg ctt att ggt atc cca gga tta gag aaa gcc cat    342
His Ala Thr Cys Val Leu Ile Gly Ile Pro Gly Leu Glu Lys Ala His
        10                  15                  20 ttc tgg gtt ggc ttc ccc ctc ctt tcc atg tat gta gtg gca atg tgt    390
Phe Trp Val Gly Phe Pro Leu Leu Ser Met Tyr Val Val Ala Met Cys
    25                  30                  35 gga aac tgc atc gtg gtc ttc atc gta agg acg gaa cgc agc ctg cac    438
Gly Asn Cys Ile Val Val Phe Ile Val Arg Thr Glu Arg Ser Leu His
40                  45                  50                  55 gct ccg atg tac ctc ttt ctc tgc atg ctt gca gcc att gac ctg gcc    486
Ala Pro Met Tyr Leu Phe Leu Cys Met Leu Ala Ala Ile Asp Leu Ala
                60                  65                  70 tta tcc aca tcc acc atg cct aag atc ctt gcc ctt ttc tgg ttt gat    534
Leu Ser Thr Ser Thr Met Pro Lys Ile Leu Ala Leu Phe Trp Phe Asp
            75                  80                  85 tcc cga gag att agc att gag gcc tgt ctt acc cag atg ttc ttt att    582
Ser Arg Glu Ile Ser Ile Glu Ala Cys Leu Thr Gln Met Phe Phe Ile
        90                  95                 100 cat gcc ctc tca gcc att gaa tcc acc atc ctg ctg gcc atg gcc ttt    630
His Ala Leu Ser Ala Ile Glu Ser Thr Ile Leu Leu Ala Met Ala Phe
    105                 110                 115 gac cgt tat gtg gcc atc tgc cac cca ctg cgc cat gct gca gtg ctc    678
Asp Arg Tyr Val Ala Ile Cys His Pro Leu Arg His Ala Ala Val Leu
120                 125                 130                 135 aac aat aca gta aca gcc cag att ggc atc gtg gct gtg gtc cgc gga    726
Asn Asn Thr Val Thr Ala Gln Ile Gly Ile Val Ala Val Val Arg Gly
                140                 145                 150 tcc ctc ttt ttt ttc cca ctg cct ctg ctg atc aag cgg ctg gcc ttc    774
Ser Leu Phe Phe Phe Pro Leu Pro Leu Leu Ile Lys Arg Leu Ala Phe
            155                 160                 165
```

-continued

| | |
|---|---|
| tgc cac tcc aat gtc ctc tcg cac tcc tat tgt gtc cac cag gat gta<br>Cys His Ser Asn Val Leu Ser His Ser Tyr Cys Val His Gln Asp Val<br>170                  175                180 | 822 |
| atg aag ttg gcc tat gca gac act ntg ccc aat gtg gta tat ggt ctt<br>Met Lys Leu Ala Tyr Ala Asp Thr Xaa Pro Asn Val Val Tyr Gly Leu<br>185                  190                195 | 870 |
| act gcc att ctg ctg gtc atg ggc gtg gac gta atg ttc atc tcc ttg<br>Thr Ala Ile Leu Leu Val Met Gly Val Asp Val Met Phe Ile Ser Leu<br>200                  205                210                215 | 918 |
| tcc tat ttt ctg ata ata cga acg gtt ctg caa ctg cct tcc aag tca<br>Ser Tyr Phe Leu Ile Ile Arg Thr Val Leu Gln Leu Pro Ser Lys Ser<br>220                  225                230 | 966 |
| gag cgg gcc aag gcc ttt gga acc tgt gtg tca cac att ggt gtg gta<br>Glu Arg Ala Lys Ala Phe Gly Thr Cys Val Ser His Ile Gly Val Val<br>235                  240                245 | 1014 |
| ctc gcc ttc tat gtg cca ctt att ggc ctc tca gtt gta cac cgc ttt<br>Leu Ala Phe Tyr Val Pro Leu Ile Gly Leu Ser Val Val His Arg Phe<br>250                  255                260 | 1062 |
| gga aac agc ctt cat ccc att gtg cgt gtt gtc atg ggt gac atc tac<br>Gly Asn Ser Leu His Pro Ile Val Arg Val Val Met Gly Asp Ile Tyr<br>265                  270                275 | 1110 |
| ctg ctg ctg cct cct gtc atc aat ccc atc atc tat ggt gcc aaa acc<br>Leu Leu Leu Pro Pro Val Ile Asn Pro Ile Ile Tyr Gly Ala Lys Thr<br>280                  285                290                295 | 1158 |
| aaa cag atc aga aca cgg gtg ctg gct atg ttc aag atc agc tgt gac<br>Lys Gln Ile Arg Thr Arg Val Leu Ala Met Phe Lys Ile Ser Cys Asp<br>300                  305                310 | 1206 |
| aag gac ttg cag gct gtg gga ggc aag tga cccttaacac tacactrctc<br>Lys Asp Leu Gln Ala Val Gly Gly Lys<br>315                  320 | 1256 |
| cttatcttta ttggcttgat aaacataatt atttctaaca ctagcttatt tccagttgcc | 1316 |
| cataagcaca tcagtacttt tctctggctg aatagtaaa ctaaagtatg gtacatctac | 1376 |
| ctaaaggact attatgtgga ataatacata ctaatgaagt attacatgat ttaaagacta | 1436 |
| caataaaacc aaacatgctt ataacattaa aaaaaaa | 1474 |

<210> SEQ ID NO 2
<211> LENGTH: 320
<212> TYPE: PRT
<213> ORGANISM: Homo sapiens
<220> FEATURE:
<221> NAME/KEY: SITE
<222> LOCATION: (192)
<223> OTHER INFORMATION: Xaa equals any amino acid

<400> SEQUENCE: 2

Met Ser Ser Cys Asn Phe Thr His Ala Thr Cys Val Leu Ile Gly Ile
1               5                   10                 15

Pro Gly Leu Glu Lys Ala His Phe Trp Val Gly Phe Pro Leu Leu Ser
               20                   25                   30

Met Tyr Val Val Ala Met Cys Gly Asn Cys Ile Val Val Phe Ile Val
            35                   40                   45

Arg Thr Glu Arg Ser Leu His Ala Pro Met Tyr Leu Phe Leu Cys Met
  50                    55                   60

Leu Ala Ala Ile Asp Leu Ala Leu Ser Thr Ser Thr Met Pro Lys Ile
65               70                   75                   80

Leu Ala Leu Phe Trp Phe Asp Ser Arg Glu Ile Ser Ile Glu Ala Cys
               85                   90                   95

-continued

```
Leu Thr Gln Met Phe Phe Ile His Ala Leu Ser Ala Ile Glu Ser Thr
            100                 105                 110
Ile Leu Leu Ala Met Ala Phe Asp Arg Tyr Val Ala Ile Cys His Pro
        115                 120                 125
Leu Arg His Ala Ala Val Leu Asn Asn Thr Val Thr Ala Gln Ile Gly
    130                 135                 140
Ile Val Ala Val Val Arg Gly Ser Leu Phe Phe Pro Leu Pro Leu
145                 150                 155                 160
Leu Ile Lys Arg Leu Ala Phe Cys His Ser Asn Val Leu Ser His Ser
                165                 170                 175
Tyr Cys Val His Gln Asp Val Met Lys Leu Ala Tyr Ala Asp Thr Xaa
            180                 185                 190
Pro Asn Val Val Tyr Gly Leu Thr Ala Ile Leu Leu Val Met Gly Val
        195                 200                 205
Asp Val Met Phe Ile Ser Leu Ser Tyr Phe Leu Ile Ile Arg Thr Val
    210                 215                 220
Leu Gln Leu Pro Ser Lys Ser Glu Arg Ala Lys Ala Phe Gly Thr Cys
225                 230                 235                 240
Val Ser His Ile Gly Val Val Leu Ala Phe Tyr Val Pro Leu Ile Gly
                245                 250                 255
Leu Ser Val Val His Arg Phe Gly Asn Ser Leu His Pro Ile Val Arg
            260                 265                 270
Val Val Met Gly Asp Ile Tyr Leu Leu Leu Pro Pro Val Ile Asn Pro
        275                 280                 285
Ile Ile Tyr Gly Ala Lys Thr Lys Gln Ile Arg Thr Arg Val Leu Ala
    290                 295                 300
Met Phe Lys Ile Ser Cys Asp Lys Asp Leu Gln Ala Val Gly Gly Lys
305                 310                 315                 320
```

<210> SEQ ID NO 3
<211> LENGTH: 963
<212> TYPE: DNA
<213> ORGANISM: Homo sapiens
<220> FEATURE:
<221> NAME/KEY: CDS
<222> LOCATION: (1)..(960)

<400> SEQUENCE: 3

```
atg agt tcc tgc aac ttc aca cat gcc acc ttt gtg ctt att ggt atc      48
Met Ser Ser Cys Asn Phe Thr His Ala Thr Phe Val Leu Ile Gly Ile
  1               5                  10                  15 cca gga tta gag aaa gcc cat ttc tgg gtt ggc ttc ccc ctc ctt tcc      96
Pro Gly Leu Glu Lys Ala His Phe Trp Val Gly Phe Pro Leu Leu Ser
                 20                  25                  30 atg tat gta gtg gca atg ttt gga aac tgc atc gtg gtc ttc atc gta     144
Met Tyr Val Val Ala Met Phe Gly Asn Cys Ile Val Val Phe Ile Val
             35                  40                  45 agg acg gaa cgc agc ctg cac gct ccg atg tac ctc ttt ctc tgc atg     192
Arg Thr Glu Arg Ser Leu His Ala Pro Met Tyr Leu Phe Leu Cys Met
         50                  55                  60 ctt gca gcc att gac ctg gcc tta tcc aca tcc acc atg cct aag atc     240
Leu Ala Ala Ile Asp Leu Ala Leu Ser Thr Ser Thr Met Pro Lys Ile
 65                  70                  75                  80 ctt gcc ctt ttc tgg ttt gat tcc cga gag att agc ttt gag gcc tgt     288
Leu Ala Leu Phe Trp Phe Asp Ser Arg Glu Ile Ser Phe Glu Ala Cys
                 85                  90                  95 ctt acc cag atg ttc ttt att cat gcc ctc tca gcc att gaa tcc acc     336
Leu Thr Gln Met Phe Phe Ile His Ala Leu Ser Ala Ile Glu Ser Thr
```

|  |  |  |  |  |  |  |  |  |  |  |  |  |  |  |  |
|---|---|---|---|---|---|---|---|---|---|---|---|---|---|---|---|

```
                     100                 105                 110
atc ctg ctg gcc atg gcc ttt gac cgt tat gtg gcc atc tgc cac cca     384
Ile Leu Leu Ala Met Ala Phe Asp Arg Tyr Val Ala Ile Cys His Pro
            115                 120                 125 ctg cgc cat gct gca gtg ctc aac aat aca gta aca gcc cag att ggc     432
Leu Arg His Ala Ala Val Leu Asn Asn Thr Val Thr Ala Gln Ile Gly
    130                 135                 140 atc gtg gct gtg gtc cgc gga tcc ctc ttt ttt ttc cca ctg cct ctg     480
Ile Val Ala Val Val Arg Gly Ser Leu Phe Phe Phe Pro Leu Pro Leu
145                 150                 155                 160 ctg atc aag cgg ctg gcc ttc tgc cac tcc aat gtc ctc tcg cac tcc     528
Leu Ile Lys Arg Leu Ala Phe Cys His Ser Asn Val Leu Ser His Ser
                165                 170                 175 tat tgt gtc cac cag gat gta atg aag ttg gcc tat gca gac act ttg     576
Tyr Cys Val His Gln Asp Val Met Lys Leu Ala Tyr Ala Asp Thr Leu
            180                 185                 190 ccc aat gtg gta tat ggt ctt act gcc att ctg ctg gtc atg ggc gtg     624
Pro Asn Val Val Tyr Gly Leu Thr Ala Ile Leu Leu Val Met Gly Val
    195                 200                 205 gac gta atg ttc atc tcc ttg tcc tat ttt ctg ata ata cga acg gtt     672
Asp Val Met Phe Ile Ser Leu Ser Tyr Phe Leu Ile Ile Arg Thr Val
210                 215                 220 ctg caa ctg cct tcc aag tca gag cgg gcc aag gcc ttt gga acc tgt     720
Leu Gln Leu Pro Ser Lys Ser Glu Arg Ala Lys Ala Phe Gly Thr Cys
225                 230                 235                 240 gtg tca cac att ggt gtg gta ctc gcc ttc tat gtg cca ctt att ggc     768
Val Ser His Ile Gly Val Val Leu Ala Phe Tyr Val Pro Leu Ile Gly
                245                 250                 255 ctc tca gtt gta cac cgc ttt gga aac agc ctt cat ccc att gtg cgt     816
Leu Ser Val Val His Arg Phe Gly Asn Ser Leu His Pro Ile Val Arg
            260                 265                 270 gtt gtc atg ggt gac atc tac ctg ctg ctg cct cct gtc atc aat ccc     864
Val Val Met Gly Asp Ile Tyr Leu Leu Leu Pro Pro Val Ile Asn Pro
    275                 280                 285 atc atc tat ggt gcc aaa acc aaa cag atc aga aca cgg gtg ctg gct     912
Ile Ile Tyr Gly Ala Lys Thr Lys Gln Ile Arg Thr Arg Val Leu Ala
290                 295                 300 atg ttc aag atc agc tgt gac aag gac ttg cag gct gtg gga ggc aag     960
Met Phe Lys Ile Ser Cys Asp Lys Asp Leu Gln Ala Val Gly Gly Lys
305                 310                 315                 320 tga                                                                 963
```

<210> SEQ ID NO 4
<211> LENGTH: 320
<212> TYPE: PRT
<213> ORGANISM: Homo sapiens

<400> SEQUENCE: 4

```
Met Ser Ser Cys Asn Phe Thr His Ala Thr Phe Val Leu Ile Gly Ile
 1               5                  10                  15

Pro Gly Leu Glu Lys Ala His Phe Trp Val Gly Phe Pro Leu Leu Ser
            20                  25                  30

Met Tyr Val Val Ala Met Phe Gly Asn Cys Ile Val Val Phe Ile Val
        35                  40                  45

Arg Thr Glu Arg Ser Leu His Ala Pro Met Tyr Leu Phe Leu Cys Met
    50                  55                  60

Leu Ala Ala Ile Asp Leu Ala Leu Ser Thr Ser Thr Met Pro Lys Ile
65                  70                  75                  80
```

```
Leu Ala Leu Phe Trp Phe Asp Ser Arg Glu Ile Ser Phe Glu Ala Cys
                85                  90                  95

Leu Thr Gln Met Phe Phe Ile His Ala Leu Ser Ala Ile Glu Ser Thr
            100                 105                 110

Ile Leu Leu Ala Met Ala Phe Asp Arg Tyr Val Ala Ile Cys His Pro
        115                 120                 125

Leu Arg His Ala Ala Val Leu Asn Asn Thr Val Thr Ala Gln Ile Gly
    130                 135                 140

Ile Val Ala Val Val Arg Gly Ser Leu Phe Phe Pro Leu Pro Leu
145                 150                 155                 160

Leu Ile Lys Arg Leu Ala Phe Cys His Ser Asn Val Leu Ser His Ser
                165                 170                 175

Tyr Cys Val His Gln Asp Val Met Lys Leu Ala Tyr Ala Asp Thr Leu
            180                 185                 190

Pro Asn Val Val Tyr Gly Leu Thr Ala Ile Leu Leu Val Met Gly Val
        195                 200                 205

Asp Val Met Phe Ile Ser Leu Ser Tyr Phe Leu Ile Ile Arg Thr Val
    210                 215                 220

Leu Gln Leu Pro Ser Lys Ser Glu Arg Ala Lys Ala Phe Gly Thr Cys
225                 230                 235                 240

Val Ser His Ile Gly Val Val Leu Ala Phe Tyr Val Pro Leu Ile Gly
                245                 250                 255

Leu Ser Val Val His Arg Phe Gly Asn Ser Leu His Pro Ile Val Arg
            260                 265                 270

Val Val Met Gly Asp Ile Tyr Leu Leu Pro Pro Val Ile Asn Pro
        275                 280                 285

Ile Ile Tyr Gly Ala Lys Thr Lys Gln Ile Arg Thr Arg Val Leu Ala
    290                 295                 300

Met Phe Lys Ile Ser Cys Asp Lys Asp Leu Gln Ala Val Gly Gly Lys
305                 310                 315                 320

<210> SEQ ID NO 5
<211> LENGTH: 314
<212> TYPE: PRT
<213> ORGANISM: Homo sapiens

<400> SEQUENCE: 5

Met Met Gly Gln Asn Gln Thr Ser Ile Ser Asp Phe Leu Leu Leu Gly
1               5                   10                  15

Leu Pro Ile Gln Pro Glu Gln Gln Asn Leu Cys Tyr Ala Leu Phe Leu
            20                  25                  30

Ala Met Tyr Leu Thr Thr Leu Leu Gly Asn Leu Leu Ile Ile Val Leu
        35                  40                  45

Ile Arg Leu Asp Ser His Leu His Thr Pro Met Tyr Leu Phe Leu Ser
    50                  55                  60

Asn Leu Ser Phe Ser Asp Leu Cys Phe Ser Ser Val Thr Ile Pro Lys
65                  70                  75                  80

Leu Leu Gln Asn Met Gln Asn Gln Asp Pro Ser Ile Pro Tyr Ala Asp
                85                  90                  95

Cys Leu Thr Gln Met Tyr Phe Leu Leu Phe Gly Asp Leu Glu Ser
            100                 105                 110

Phe Leu Leu Val Ala Met Ala Tyr Asp Arg Tyr Val Ala Ile Cys Phe
        115                 120                 125

Pro Leu His Tyr Thr Ala Ile Met Ser Pro Met Leu Cys Leu Ala Leu
    130                 135                 140
```

```
Val Ala Leu Ser Trp Val Leu Thr Thr Phe His Ala Met Leu His Thr
145                 150                 155                 160

Leu Leu Met Ala Arg Leu Cys Phe Cys Ala Asp Asn Val Ile Pro His
            165                 170                 175

Phe Phe Cys Asp Met Ser Ala Leu Leu Lys Leu Ala Phe Ser Asp Thr
        180                 185                 190

Arg Val Asn Glu Trp Val Ile Phe Ile Met Gly Gly Leu Ile Leu Val
    195                 200                 205

Ile Pro Phe Leu Leu Ile Leu Gly Ser Tyr Ala Arg Ile Val Ser Ser
210                 215                 220

Ile Leu Lys Val Pro Ser Ser Lys Gly Ile Cys Lys Ala Phe Ser Thr
225                 230                 235                 240

Cys Gly Ser His Leu Ser Val Val Ser Leu Phe Tyr Gly Thr Val Ile
                245                 250                 255

Gly Leu Tyr Leu Cys Ser Ser Ala Asn Ser Ser Thr Leu Lys Asp Thr
            260                 265                 270

Val Met Ala Met Met Tyr Thr Val Thr Pro Met Leu Asn Pro Phe
275                 280                 285

Ile Tyr Ser Leu Arg Asn Arg Asp Met Lys Gly Ala Leu Ser Arg Val
290                 295                 300

Ile His Gln Lys Lys Thr Phe Phe Ser Leu
305                 310
```

<210> SEQ ID NO 6
<211> LENGTH: 33
<212> TYPE: DNA
<213> ORGANISM: Artificial sequence
<220> FEATURE:
<223> OTHER INFORMATION: Contains the Xba I restriction enzyme site

<400> SEQUENCE: 6
actgccatgg gccgctttgg aaacagcctt cat                                33

<210> SEQ ID NO 7
<211> LENGTH: 28
<212> TYPE: DNA
<213> ORGANISM: Artificial sequence
<220> FEATURE:
<223> OTHER INFORMATION: Contains the Asp 718 restriction site

<400> SEQUENCE: 7
gtacagatct cttgcctccc acagcctg                                      28

<210> SEQ ID NO 8
<211> LENGTH: 38
<212> TYPE: DNA
<213> ORGANISM: Artificial sequence
<220> FEATURE:
<223> OTHER INFORMATION: Contains the BglII site

<400> SEQUENCE: 8
gctagtctag atccgccatc atgagttcct gcaacttc                            38

<210> SEQ ID NO 9
<211> LENGTH: 30
<212> TYPE: DNA
<213> ORGANISM: Artificial sequence
<220> FEATURE:
<223> OTHER INFORMATION: Contains the XbaI site

<400> SEQUENCE: 9

-continued

```
gcagcaggta cctcacttgc ctcccacagc                                        30

<210> SEQ ID NO 10
<211> LENGTH: 64
<212> TYPE: DNA
<213> ORGANISM: Homo sapiens

<400> SEQUENCE: 10
catggaagat ctgccaccat ggactacaaa gacgatgacg acaagagttc ctgcaacttc        60
acac                                                                    64

<210> SEQ ID NO 11
<211> LENGTH: 33
<212> TYPE: DNA
<213> ORGANISM: Homo sapiens

<400> SEQUENCE: 11
cattgctcta gatcacttgc ctcccacagc ctg                                    33

<210> SEQ ID NO 12
<211> LENGTH: 733
<212> TYPE: DNA
<213> ORGANISM: Homo sapiens

<400> SEQUENCE: 12
gggatccgga gcccaaatct tctgacaaaa ctcacacatg cccaccgtgc ccagcacctg        60
aattcgaggg tgcaccgtca gtcttcctct tccccccaaa acccaaggac accctcatga      120
tctcccggac tcctgaggtc acatgcgtgg tggtggacgt aagccacgaa gaccctgagg      180
tcaagttcaa ctggtacgtg gacggcgtgg aggtgcataa tgccaagaca aagccgcggg      240
aggagcagta caacagcacg taccgtgtgg tcagcgtcct caccgtcctg caccaggact      300
ggctgaatgg caaggagtac aagtgcaagg tctccaacaa agccctccca acccccatcg      360
agaaaaccat ctccaaagcc aaagggcagc ccgagaacc acaggtgtac accctgcccc      420
catcccggga tgagctgacc aagaaccagg tcagcctgac ctgcctggtc aaaggcttct      480
atccaagcga catcgccgtg gagtgggaga gcaatgggca gccggagaac aactacaaga      540
ccacgcctcc cgtgctggac tccgacggct ccttcttcct ctacagcaag ctcaccgtgg      600
acaagagcag gtggcagcag gggaacgtct tctcatgctc cgtgatgcat gaggctctgc      660
acaaccacta cacgcagaag agcctctccc tgtctccggg taaatgagtg cgacggccgc      720
gactctagag gat                                                         733
```